United States Patent
Horowitz et al.

(10) Patent No.: US 6,552,177 B2
(45) Date of Patent: Apr. 22, 2003

(54) EH DOMAIN CONTAINING GENES AND PROTEINS

(75) Inventors: Mia Horowitz, Ramat Hasharon (IL); Liat Mintz, Herzlia (IL)

(73) Assignee: Ramot University Authority for Applied Research & Industrial Development Ltd., Tel Aviv (IL)

( * ) Notice: Subject to any disclaimer, the term of this patent is extended or adjusted under 35 U.S.C. 154(b) by 0 days.

(21) Appl. No.: 09/312,762

(22) Filed: May 17, 1999

(65) Prior Publication Data

US 2002/0115069 A1 Aug. 22, 2002

Related U.S. Application Data

(63) Continuation-in-part of application No. 09/026,898, filed on Feb. 20, 1998, now abandoned.

(30) Foreign Application Priority Data

Feb. 21, 1997 (IL) .................................................. 120283

(51) Int. Cl.$^7$ ........................ C07H 21/02; C07H 21/04; C12Q 1/68; C12P 19/37

(52) U.S. Cl. ........................ 536/23.1; 536/24.3; 435/6; 435/91.2

(58) Field of Search ................................ 536/23.1, 24.3; 435/6, 91.2

(56) References Cited

PUBLICATIONS

Marra et al, Genbank Locus W40735 Sep. 1996.*
Fernandez–Trigo et al, "Prognostic implications of chemoresistance–sensitivity assays for colorectal and appendiceal cancer", Am J. Clin. Oncol. 18(5):454–60. Abstract Only 1995.*
Probst et al, "The G–tetrad in antisense targeting", Trends Genetics 12(8):90–91 1996.*
Harris et al, "Strategies for targeted gene therapy" Trends Genetics 12(10):400–405 1996.*
Marshall et al, "Gene Therapy's growing pains", Science 269:1050–1055 Aug. 1995.*
Guru et al, "A transcript map for the 2.8 Mb region containing the multiple endocrine neoplasia type 1 locus", Genome Research 7:725–735 Jul. 1997.*
Mintz et al, "EHD1—an EH–domain protein with a specific expression pattern", Genomics 59:66–76 Jul. 1999.*

* cited by examiner

Primary Examiner—Jeffrey Fredman
(74) Attorney, Agent, or Firm—G.E. Ehrlich Ltd.

(57) ABSTRACT

The present invention teaches novel Eps15 homology (EH) domain containing proteins, polynucleotide sequences encoding the novel EH domain containing proteins, oligonucleotides and oligonucleotide analogs derived from the polynucleotide sequences, a display library displaying short peptides derived from the EH domain containing proteins, antibodies recognizing the EH domain containing proteins, peptides or peptide analogs derived from the EH domain containing proteins, and pharmaceutical compositions and methods of employing the peptides or peptide analogs, the oligonucleotides and oligonucleotide analogs, and/or the polynucleotide sequences to up-regulate or down-regulate clathrin coated pit mediated endocytosis and thereby insulin growth factor 1 receptor (IGF1 receptor) signaling.

4 Claims, 24 Drawing Sheets

(5 of 24 Drawing Sheet(s) Filed in Color)

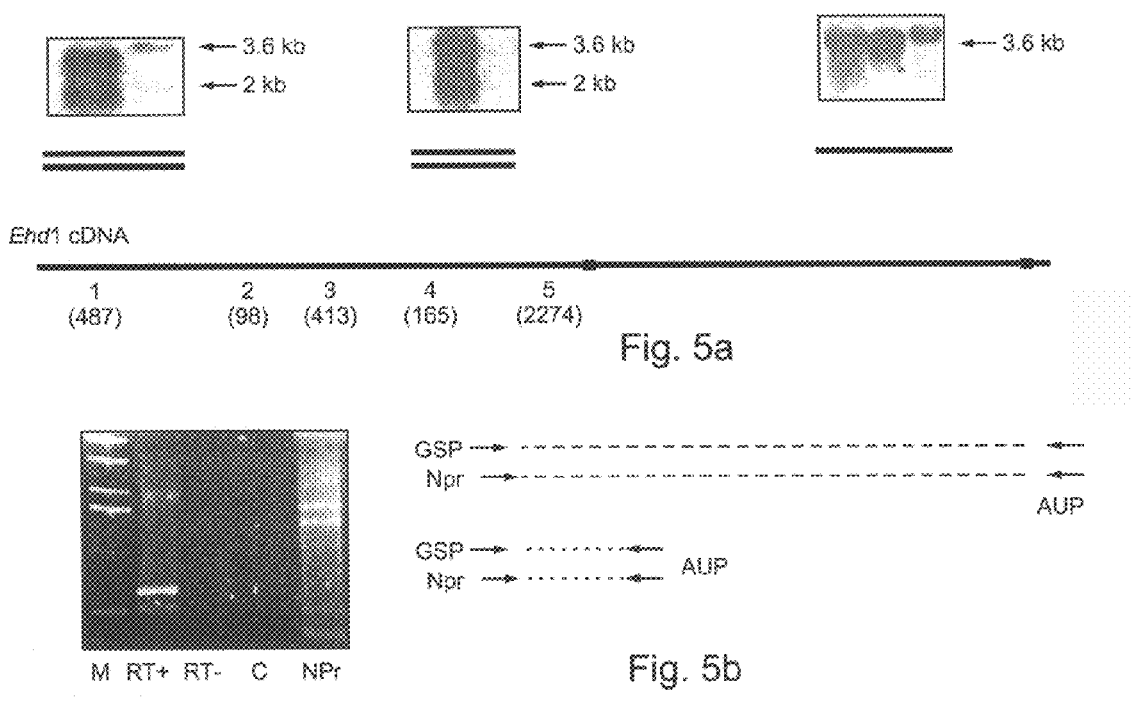

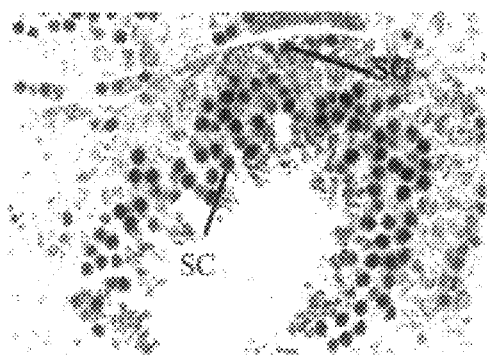
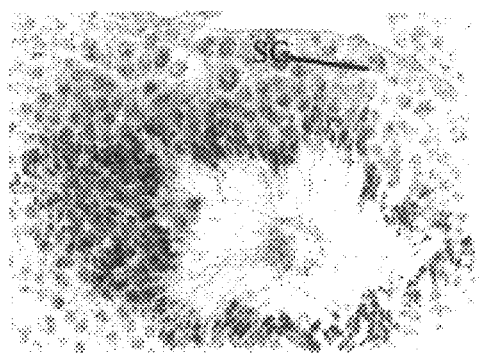
Fig. 7a  Fig. 7b
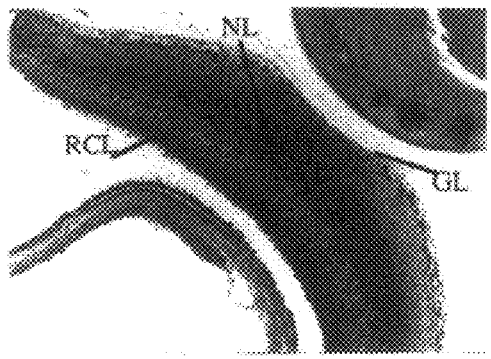
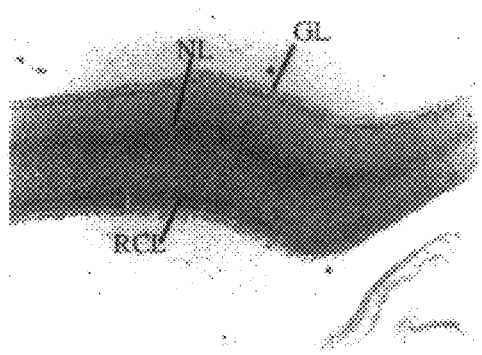
Fig. 7c  Fig. 7d
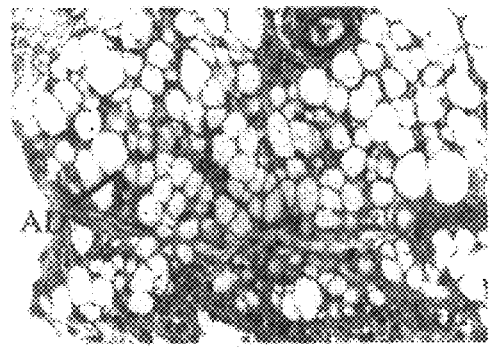
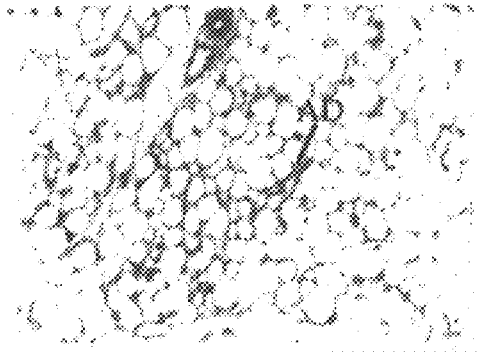
Fig. 7e  Fig. 7f

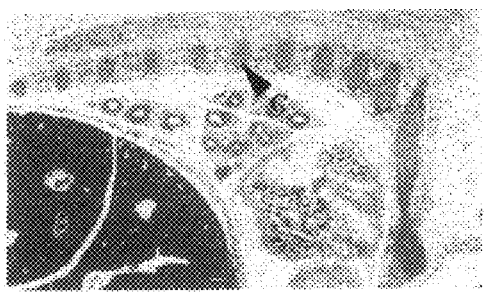
Fig. 8a
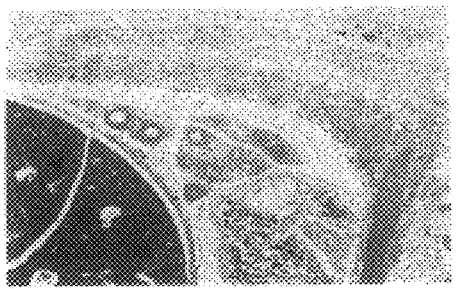
Fig. 8b
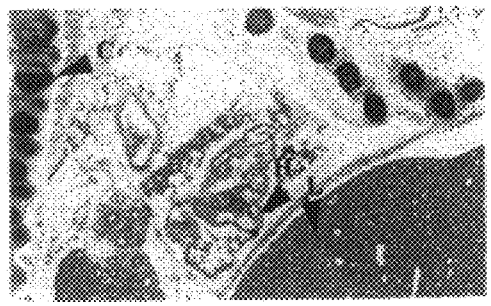
Fig. 8c
Fig. 8d
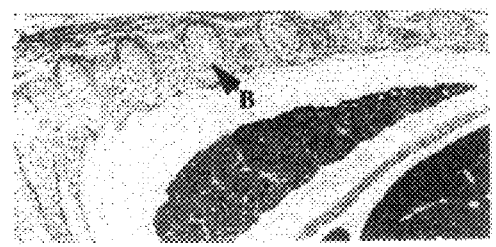
Fig. 8e
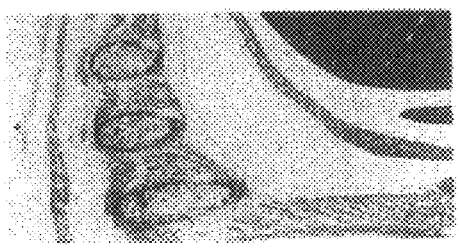
Fig. 8f
Fig. 8g
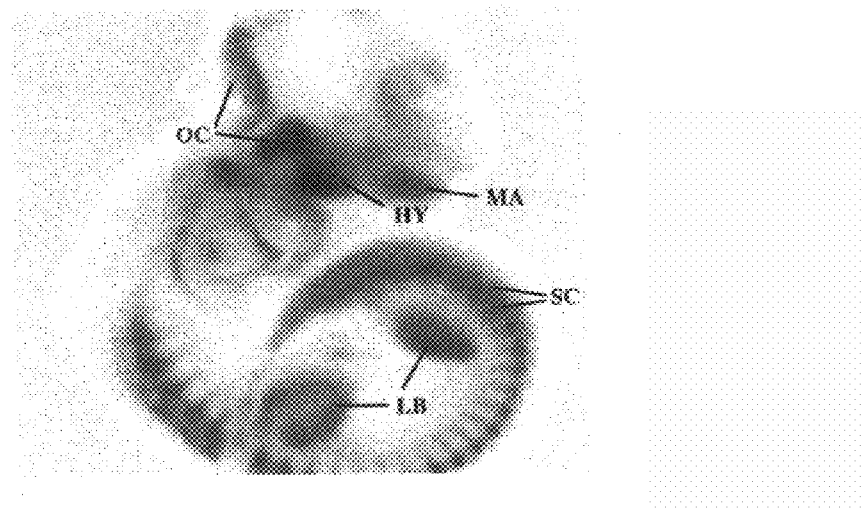

```
OCD   1 CGTGTCCGGCAGTATGTTCAGCTGGGTCAGCAAGGATGCCCGCCGCAAGA  50 (SEQ ID NO:13)
          ||| ||||||||| |||||||||||||| |||||||||||||||||||||
C3H  70 CGTCTCCGGCATCATGTTCAGCTGGGTGAGCAAGGATGCCCGCCGCAAGA 119 (SEQ ID NO:2)

OCD  51 AGGAGCCGGAGCTCTTCCAGACGGTGGCTGAGGGGCTGCGGCAGCTGTAC 100
        |||||||||||||||||||||||||||||| |||||||||||| |||||
C3H 120 AGGAGCCGGAGCTCTTCCAGACGGTGGCCGAGGGGCTGCGGCACGTGTAC 169

OCD 101 GCGCAGAAGCTGCTACCCCTGGAGGAGCACTACCGCTTCCACGAGTTCCA 150
        ||||||||||||||  |||||||||||||||| |||||||||||||||||
C3H 170 GCGCAGAAGCTGCTGCCGCTGGAGGAGCACTATCGCTTCCACGAGTTCCA 219

OCD 151 CTCGCCCGCGCTGGAGGACGCTGACTTCGACAACAAGCCTATGGTGCTCC 200
        |||||||||||||||||||||||||||||||||||||||| |||||||||
C3H 220 CTCGCCCGCGCTGGAGGACGCTGACTTCGACAACAAGCCGATGGTGCTCC 269

OCD 201 TCGTGGGGCAGTACAGCACGGGCAAGACCACCTTCATCCGACACCTGATC 250
        | || || |||||||||||| |||||||||||||||||||| | ||||||
C3H 270 TGGTCGGCCAGTACAGCACCGGCAAGACCACCTTCATCCGCCACCTGATC 319

OCD 251 GAGCAGGACTTCCCGGGGATGCGCATCGGGCCCGAGCCCACCACCGACTC 300
        |||||||||||||||||||||||||||||||| |||||||||||||||||
C3H 320 GAGCAGGACTTCCCGGGGATGCGCATCGGGCCGGAGCCCACCACCGACTC 369

OCD 301 CTTCATCGCCGTCATGCACGGCCCCACTGAGGGCGTGGTGCCGGGCAACG 350
        |||||||| |||||||||||||||| |||||||||||||||| ||||||
C3H 370 CTTCATCGCGGTCATGCACGGCCCCACCGAGGGCGTGGTGCCCGGCAACG 419

OCD 351 CGCTCGTGGTGGACCCGCGGCGCCCCCTTCCGCAAGCTCAACGCGTTTGGC 400
        |||||| |||||||||||||||||||||||||||||||||||| || |||
C3H 420 CGCTCGTCGTGGACCCGCGGCGCCCCCTTCCGCAAGCTCAACGCCTTCGGC 469

OCD 401 AACGCTTTCCTCAACAGGTTCATGTGGCCCCA 432
        ||||| ||||||||||||||||||||| | ||
C3H 470 AACGCCTTCCTCAACAGGTTCATGTGTGCACA 501
```

Fig. 14

```
EHD2  251 TCCAGCAGCTGGGGCAGCCCGGGCCATGGTGCGTCTGAGCCCCGAGCTCT 300  (SEQ ID NO:6)
                                                    ||
EHD1    1 .............................................ATTCG   5  (SEQ ID NO:2)

301 GGTAAGGCAGTAGTGGCGGCGTTGTTCGAGCTAGGCGGGTGCCACTCCCG 350
          |   ||      |   ||       || |||  ||     || | ||
        6 GCACGGGGTCGGCCGCGCGCCCCAGTCCCGCTCAGCCACCGCTCCGTCCT  55

351 GGAGCTTCCTCCC....AGCTGTCACAATGTTCAGTTGGCTGGGTAACGA 396
          | |||  ||  ||    |  ||  |||||||||| ||| || | || ||
       56 GTAGCAGCCAGCCCCGTCTCCGGCATCATGTTCAGCTGGGTGAGCAAGGA 105

397 TGATCGCCGCAAGAAGGACCCTGAGGTCTTCCAGACGGTGAGCGATGGAC 446
          ||  |||||||||||||||| || ||| |||||||||||| ||| || |
      106 TGCCCGCCGCAAGAAGGAGCCGGAGCTCTTCCAGACGGTGGCCGAGGGGC 155

447 TCAAAAAACTCTACAAGACCAAGCTGCTGCCTCTGGAAGAGTATTACCGC 496
          |     |  | |||  |   ||||||||||| ||||||||| |||||||
      156 TGCGGCACGTGTACGCGCAGAAGCTGCTGCCGCTGGAGGAGCACTATCGC 205

497 TTCCACGAGTTCCACTCGCCCGCCCTGGAAGATGCTGATTTCGACAACAA 546
          ||||||||||||||||||||||||| ||||| ||||||  ||||||||||
      206 TTCCACGAGTTCCACTCGCCCGCGCTGGAGGACGCTGACTTCGACAACAA 255

547 GCCCATGGTCCTGTTGGTGGGCCAGTACTCTACCGGCAAGACCACCTTCA 596
          |||  ||||| ||   ||||  ||||||||||    ||||||||||||||
      256 GCCGATGGTGCTCCTGGTCGGCCAGTACAGCACCGGCAAGACCACCTTCA 305

597 TCAGGTACCTGCTGGAACAGGATTTTCCAGGCATGAGGATTGGGCCTGAG 646
          || |  |||||   ||   |||| || || || || |  || ||||| ||
      306 TCCGCCACCTGATCGAGCAGGACTTCCCGGGGATGCGCATCGGGCCGGAG 355

647 CCGACCACTGATTCCTTCATAGCAGTGATGCAGGGAGATGTGGAGGGGAT 696
          || ||||| || |||||||| || || ||||| ||         ||||| |
      356 CCCACCACCGACTCCTTCATCGCGGTCATGCACGGCCCCACCGAGGGCGT 405

697 CATTCCCGGGAATGCCTTGGTGGTGGATCCAAAGAAACCCTTCAGAAAGC 746
          |  |||||| ||  || |  | ||  |||| ||  |  ||||||  ||||
      406 GGTGCCCGGCAACGCGCTCGTCGTGGACCCGCGGCGCCCCCTTCCGCAAGC 455

747 TCAACGCCTTTGGCAACGCCTTCCTGAACAGGTTTGTGTGTGCCCAGCTG 796
          ||||||||||  |||||||||||||| ||||||| ||||||| ||||| |
      456 TCAACGCCTTCGGCAACGCCTTCCTCAACAGGTTCATGTGTGCACAGCTG 505

797 CCCAACGCCGTGCTTGAAAGTATCAGTGTGATCGACACACCGGGGATCCT 846
          ||||| | ||| || || || |||||   ||| ||||| || |||||||
      506 CCCAACCCAGTACTGGACAGCATCAGCATCATTGACACTCCTGGGATCCT 555

847 CTCTGGGGAGAAGCAGAGGATCAGCCGAGGGTATGATTTTGCTGCGGTCC 896
          ||||||||||||||  | | ||||||||||| ||| |  |||| | ||||
      556 GTCTGGGGAGAAGCAGCGCATCAGCCGAGGTTATGACTTTGCGGCTGTCC 605

897 TCGAATGGTTTGCTGAGCGGGTGGACCGAATTATCCTACTCTTCGACGCC 946
          | || |||| || |||| || |||||||| ||  |  | |  ||||||||
      606 TTGAGTGGTTCGCAGAGCGTGTGGACCGCATCATCTTGTTGTTCGACGCC 655

947 CACAAGCTGGACATCTCCGATGAGTTCTCAGAAGTCATCAAGGCTCTCAA 996
          ||||||||||||||||| || |||||||||||||||||||||||| ||||
      656 CACAAGCTGGACATCTCAGACGAGTTCTCAGAAGTCATCAAGGCCCTCAA 705

997 GAACCATGAGGACAAGATGCGCGTAGTGTTGAACAAGGCTGACCAGATCG 1046
          | | ||||||||||||| |  | ||| |||||||||||||| |||||||
      706 AAATCACGAGGACAAGATCCGTGTGGTGCTGAACAAGGCTGATCAGATCG 755

1047 AGACCCAGCAGCTGATGCGAGTATACGGAGCCCTCATGTGGTCCCTGGGG 1096
          |||| ||||||||||||||||||||||| ||||||||||||||||||||
      756 AGACGCAGCAGCTGATGCGAGTATACGGGGCCCTCATGTGGTCCCTGGGG 805

1097 AAGATCGTGAACACCCCCGAGGTGATCCGGGTCTACATTGGCTCCTTCTG 1146
          ||||| |  ||||||||||||||| |||| |||||||| |||||||||||
      806 AAGATCATCAACACCCCCGAGGTGGTCAGAGTCTACATCGGCTCCTTCTG 855

1147 GTCCCACCCCACTCCTCATTCCCGACAACCGGAAGCTCTTTGAAGCTGAAG 1196
          |||  ||||||||| ||||||||||||||||||| |||||||| || | |
      856 GTCACACCCACTGCTCATCCCTGACAACCGGAAGTTCTTTGAGGCGGAGG 905

1197 AGCAAGACTTGTTCAGAGACATTCAGAGTCTACCCCGTAATGCTGCTCTT 1246
          ||||  |||| |||| |||||||||| |||| ||  || || || ||
```

Fig. 18

```
 906 AGCAGGACTTTTTCAAAGACATCCAGTTTCTGCCGAGAAACGCCGCCCTC  955

1247 CGAAAGCTCAACGATCTCATCAAGAGAGCCCGGCTGGCCAAGGTCCACGC 1296
     | ||| |||| || |||||||||| | ||| |||||||||||||||| ||
 956 AGGAAGTTCAATGACCTCATCAAGCGGGCCAGGCTGGCCAAGGTCCATGC 1005

1297 CTACATCATCAGCTCCTTGAAGAAGGAGATGCCCTCAGTGTTTGGGAAGG 1346
     ||||||||||||| ||| | |||||||||||||||   || || ||||| |
1006 CTACATCATCAGTTCCCTCAAGAAGGAGATGCCCAATGTTTTCGGGAAAG 1055

1347 ACACCAAAAAGAAAGAACTGGTGAACAACCTGGCTGAGATCTATGGCCGG 1396
     | | ||| ||||||||| |||||||||||||||  ||||||||       |
1056 AGAGCAAGAAGAAAGAGCTGGTGAACAACCTGGGAGAGATCTACCAGAAG 1105

1397 ATTGAGCGAGAACACCAGATCTCCCCTGGAGACTTCCCCAACCTGAAGAA 1446
     || |||||  || ||||||||||| ||  ||||||||  | ||||    ||
1106 ATCGAGCGGGAGCACCAGATCTCCTCCGGCGACTTCCCAAGCCTGCGTAA 1155

1447 GATGCAGGACCAGCTGCAGGCCCAGGACTTCAGCAAATTCCAGCCACTGA 1496
     |||||||||  |  |||||| ||||||||||||||| || ||||| |  |||
1156 GATGCAGGAACTCCTGCAGACCCAGGACTTCAGCAAGTTCCAGGCCTTGA 1205

1497 AGAGCAAGCTGCTGGAAGTGGTTGATGATATGCTGGCTCATGACATTGCC 1546
     ||  |||||||||||||   ||  ||||||||||||||| || || || ||
1206 AGCCCAAGCTGCTGGATACAGTGGATGATATGCTGGCCAACGATATAGCT 1255

1547 CAGCTCATGGTGCTGGTGCGCCAGGAAGAGACCCAACGGCCTGTCCAGAT 1596
     | ||| |||||| |||||||||||||||   ||| |||    ||    ||
1256 CGGCTGATGGTGATGGTGCGCCAGGAGGAGTCCCTGATGCCCTCACAGGC 1305

1597 GGTGAAGGGCGGAGCATTTGAGGGAACCTTACAAGGCCCCTTCGGGCACG 1646
     ||||||| || || ||||| || ||| | | || |||||  |||||||||  |
1306 TGTGAAGGGTGGTGCTTTTGATGGCACCATGAATGGGCCCTTTGGGCATG 1355

1647 GCTATGGAGAGGGAGCTGGGGAGGGCATCGATGATGCCGAGTGGGTGGTG 1696
     |||| || ||||| ||||| ||||||||| ||||||| |||||||| || ||
1356 GCTACGGCGAGGGGGCTGGCGAGGGCATTGATGATGTTGAGTGGGTAGTT 1405

1697 GCGCGGGACAAGCCTATGTATGATGAGATCTTCTACACCTTATCCCCAGT 1746
     |    |||||||||| | ||||||||||||||||||||  || || || ||
1406 GGCAAGGACAAGCCCACCTATGATGAGATCTTCTACACACTGTCTCCTGT 1455

1747 GGATGGCAAGATCACAGGTGCCAACGCCAAGAAGGAGATGGTGCGCTCCA 1796
     | |||||||||||||||||||| || ||||||||||||||||||  ||||| | | ||
1456 CAACGGCAAGATCACAGGTGCTAATGCCAAGAAGGAGATGGTGAAGTCCA 1505

1797 AGTTGCCCAACAGCGTGCTGGGCAAGATCTGGAAGCTAGCCGACATTGAC 1846
     || |||||||||  ||||||  |||||||||||||| || || || |  ||
1506 AGCTGCCCAACACAGTGCTGGGGAAGATCTGGAAGTTGGCAGATGTGGAC 1555

1847 AAGGATGGCATGTTGGATGACGAGGAGTTTGCCCTGGCCAACCACCTTAT 1896
     |||||||||| || |||||||||||||||||||||||||||||||||||||||
1556 AAGGATGGCCTGCTGGATGACGAGGAGTTTGCCCTGGCCAACCACCTTAT 1605

1897 CAAAGTCAAGCTAGAGGGGCATGAGCTGCCCAGTGAGCTACCTGCCCACC 1946
     ||| || ||||||||||| || ||||||||||| ||| || ||| || |
1606 CAAGGTGAAGCTAGAGGGCCACAGAGCTGCCCGCTGACCTTCCTCCACATC 1655

1947 TCCTCCCTCCATATAAGAGGAAAGTATCAGAATGAGAGAGCCAGGTAACC 1996
     || | || || || ||       | ||| || |          ||
1656 TCATTCCACCCTCCAAACGGA.......GGCACGAGTGA.CTTCCATGCC 1697

1997 TCAGACAGACAGTATCAAAAGAGAGGATAGACATGTAGACCACACACACA 2046
     | ||| |   |  | | |  |    || |   ||||| |
1698 TGAGATACCTACAACCCCAGGGCTGCTGCCACTTTCTACCCACAGCTCCT 1747

2047 CACACACACACACACACACACACACACACACACAACTTGACAGTCACACT 2096
     | ||            | || || |||   |   |
1748 TGTCTGCCCAGGTGGCTGGGGCTGGAGGGGCAGAAATTG..GGGGAGGGA 1795

2097 ATAAATGAGAAGGGTTCACCTTTGTCTGAGCACCTCTCCAAGTTCC.CAG 2145
     |  |  |  ||||   |     |  || |        |||| |||
1796 AAGGGTCACCATTTTTCAAGGTCCATAAAGACCTGACGGTGTTTCCTCAG 1845

2146 GGTTGGTAGAAGGGCAGCTTTCCCTCCTCTGTCTTAGGATATAGGCCTGT 2195
     | | | |   |     | | ||  | |   |     | | || |
1846 CTCTTGAATAGGAAAACACCATCTTTCTTTTAAAGCTGTTCCGGGGTTCA 1895

2196 GTCCAAACATTCCCTCCATCTTCCATTCCCCCACAGACATGAGGCAGTTA 2245
     |   |   | |   |||  ||  ||   |  ||     |
1896 GCGGGAGGCATGGGTGATGCTTGGATATGAACAGTGGGATTTTGTGCACA 1945
```

Fig. 18 (Cont.)

```
2246 ACACAGATGGCCCACCCACTCTACCCCCAGTGCCTCCACATCTAG..... 2290
       |  |||      |  |  ||      |    |   |  |  ||  |
1946 GGAACCATGATATTTTTAATATATAACATTAGAGGCAGCTGCTGGTTTGC 1995

2291 .GCTCCGAGCAGATGGAAAAGGCTTTTTCATGGAATAGAAAATTTGCTTT 2339
      |||    |  ||  |   :  |  ||  |   ||                |    |
1996 ATCTCTTGTCTGACAGCCCNAGGATTGTTCTGGGCCCTGCTGAGGGTGAT 2045

2340 ATTTTCTATGCTTTTATTTTTTTCCCTCTGGGGCTTCCTAAGTAGAAAT 2389
      :  |  |  |  |||    ||| |        |   |||     |  |  |
2046 GCNAACCTTCTTGTTACCCTTTCTTAGCCCTCATCTTTGGCTGAGGTAGA 2095

2390 TGACTCAGGGCCTGGGAGCTGTGAGGGAAAGGAGAAGCTGAAAGAGGAGG 2439
      ||   |       |  |||   |  |      |  |  |||     |          ||
2096 AGATGTATCCTACGTGAGAGGAGTGCCGATGAAGATTGTCCTGATTAAGA 2145

2440 ACCAATCTGAGAAACCTCCATAGGGCACTGCACCCCACACTTGAAAAGAC 2489
      |||           |||        ||   |          |  |||    ||
2146 GTTAATTGTCAAAAAAAAAAAAAACTGCGCGGACGTATCCTTAGTGAGGT 2195

2490 ACTGGCCTATGTTCTCTGTGTTTTTCTCAACCCAAGACTCTCTGTCTTCC 2539
      |  |     ||     ||        |    |||    ||          |  ||
2196 ATTACGTGCTGCCGTGTTAAACGGTATGGACCTGGGTCGAATAATGTTTG 2245

2540 TCAGTAAACATGGACCTTGAATTCTGCCTGCCACTTTGGGTCAAAGACTC 2589
        |    |  |  |||  ||   |    |  |           |   ||  |
2246 GACTCTTTCGGAGTGATAGAAAACTCGCGATCGCCAAAATCCGGTGAATT 2295

2590 ACAAACAGGAAAAGAAAAAAGAAAAAATTTGGTAGGAAAGCAACAAGGAA 2639
         |                 |  |   |||  |  |     |        |
2296 GGAGTGGCCCCTTATGCGATGCGGGTGTTTCGAGGTTCATGTTGCGGTTG 2345

2640 GATAACCCTGTGTTTTTTTTCAACAGGACATTGGATTGGTGGTTCATGG 2689
            |||  |  |||    |  |      |  ||||  |  |   |||
2346 TGGTTTGTGGTGCGTGTTGTGTTATTGTGGGTGTGTTTAGGTGCGCATCT 2395

2690 GTTTGTCCCCCA..CCCCCAGCGTGGTATCTCTGGATACTCAGTTTCTTT 2737
      ||      |          |   |  |  |  |      |  |  ||   |||
2396 AGTTCACAATGATGTCGTGACTTTTGCGTTATTTAACACATTGTTGTGTG 2445

2738 ATACATACCAAGCCATTCCTGTGTGGCAAGAGCAGGGTTAGGCACTTTCT 2787
      ||  |  ||  ||||          |||||  |  ||     |
2446 GTAAAAAACAGTCCATGAACGTCTAGGAAAATGCATAAGCTACTTAGTGT 2495

2788 ATGTATTAGTCCCTGTGGCCTTCATGAATGCCCTAGGCAAGTTTGNTTCC 2837
       |  |    |    |  |||     |  ||  :||   |   |  ||  |  ||
2496 TCTGTAGTGACACTTGATACTTGACCAAGACTTTGAGTAACTTACATCAC 2545

2838 CTCCTGTTA...CTGCATTTTTCAGGTGAAGAGCCAAAGACTCAGAGTAG 2884
      ||  |       ||||||          ||      ||   |||  |
2546 TTCGTTCAAAACTGTGATTTTTGTCTCCTCTTTCCTATACTCCACCGTTG 2595

2885 TTTAGGGTACCTTCCCAAACTCCGGGAAGTCCCAAGA...........A 2922
       |  |    |||||  |     |   |  ||      |  |
2596 GACGATTTCCACCCCCAGAGCCTCGATAGAGCTGACATCCTAGGGCTTGA 2645

2923 GAGAAGATTCAAATCCAGAACTTGAGACACCCCTCTGTCCCAATTCTGTG 2972
        |       |||           ||      |  |  |        ||
2646 GTTTGCTTTCTGGCTGAGGGGAGGTCATCCCAGCTTCTGCTCAGAGGGTC 2695

2973 ATGGATGAAAGATCCCAGTGTTGCTACGTGGTGACAAAGCACAGGACAGT 3022
       |||       ||||         ||  |   ||| |     |       |
2696 TGAAATGTAGCCCCCCACCCCCGCCCCAAGGTCAACCTTTATGGTAGCTT 2745

3023 CTGAACACACAGCCCCTCACACAGCCTTCCAAAGCATCC...AGGCAAGG 3069
        |  |||||       |  |  |  ||  ||     ||    |  |  ||
2746 TCCTGGAGCCCCTCTCTGCCTTGGACAGGCAGTAGGCCCCTGTGACCTGG 2795

3070 GAGGGAGGGAGGTTCACCAGCCTTTGATGGGCCAACAATCTGACCATCTG 3119
       |  ||    |||   ||     |       |         |       |
2796 GGTGGTCTGGGGCTGGTAAGAGGAAGCCTGTGGCTCTGGCCTGGGTGTAG 2845

3120 TCACCTTGTAGAAGCAAACTGTGCCTTCTGGCC...TGCGCCTCGTGTTC 3166
       |  || || ||   |  |         |  |||   |  |  |      ||
2846 TGTCCATGCAGGACGACAGGGGAAAACCCAGCCCCTTCCCTCGCCCTGTC 2895

3167 ACAACATCACAGAAGACCAGCCAAGCCATCAGGAGAGTGGGCTGGACTGC 3216
        | ||   |        ||       |      |||||   || ||   |||
2896 ATTTCCTTCCTCTCCTCCTCTGCTGAGCCAAGGAGGTCTGGGTGTCCTGA 2945
```

Fig. 18 (Cont.)

```
3217 TAGATGTTGTCTGTGCCTATTCCTGCTCAGCCTCCCGTTCATTAGCCTAA 3266
     ||    | ||| ||       ||    ||  |       | | |
2946 GAGCCCCAGACTGAGCAGTAAGAAGCCTGAGCTAGCAAATGACCACTTTA 2995

3267 AGCATCCCAGCTCAAATTCAGCCCCAGGCTTTTACAAAGCAGGACTTCAT 3316
     || ||||     |  |  || ||     |            | |    |
2996 GTCACCCCACTGTAGCCTGGGGACCCGGACACATCCTGTGGCCAGTGGTT 3045

3317 GCTAATTCACAGAAGGCCATC..TTGAAAGGACTGGGACCTTGTTCTCTA 3364
         |||  |  |||  ||   |||    |  || | |||     ||
3046 TGGCTGTCAGGGTGGGCTTTCCACTGAGCTGGGTAGGGCATTGCAGCCTG 3095

3365 GAGTTCCAAGGACTCTGGTGTCCTTGGCAAAATTTCCATCATTCTCAGTG 3414
        ||  |    |||| |||      |  |   |    |      |  ||
3096 CTCCTCTGACACTGTAGGTGGGCTTCAGGGAGCTGGC....CTGCCAACC 3141

3415 CCCTCTATCTCCTCTGTGGTCTCCCCCTGGCTTGCCCTATGC.CCACTGT 3463
     | | |    ||  |||| |  |||      ||   || | |      ||||
3142 CCCCAGCACTGTTCTGGGCCCTCGTGAGGGTGAGCTCCAGCCTGGCCTGT 3191

3464 TGCAGTAGCTCTCTGCTACACTCCTACTGTGATGGAAAACAAAGCAAGTA 3513
     | |        |    |  ||  || |   ||     |  |  | ||  |
3192 TACCTCCCTGCCTCAGCCCTCCACTCCTTGGCTGAGGGTGAGAGAGATGT 3241

3514 TAACTTATTTTGTATCTATGTTCAGACTATATCGACTGTTCTGTGTATCT 3563
      | |    ||||     |    |   |  ||   |    | |  | |
3242 CATCCTCAGCTGTAGAGGGAGTGGCCCCCGAATGAAGACTGGTTCTCGCA 3291

3564 TCAATGTGCTTATAACTGCAGTGTGTTTGTCATTAGGATTCATGTTAATA 3613
     | |||   |   |    | ||  |  |  |  | |     | |  || | |
3292 TTAAAGGAAGTTTAATTGTGCCAAAGCCAAAAAAAAAAAAAAAAAAAAAA 3341

3614 CAACATATTTACCCTCGTGCCG 3635
     || | |
3342 AAAAAAA............... 3348
```

Fig. 18 (Cont.)

```
EHD2 370 CACAATGTTCAGTTGGCTGGGTAACGATGATCGCCGCAAGAAGGACCCTG 419  (FROM SEQ ID NO:6)
         |  ||||||||  ||| || |  ||  ||||   |||||||||||||| || |
EHD1  80 .ATCATGTTCAGCTGGGTGAGCAAGGATGCCCGCCGCAAGAAGGAGCCGG 128  (FROM SEQ ID NO:2)

420 AGGTCTTCCAGACGGTGAGCGATGGACTCAAAAAACTCTACAAGACCAAG 469
         || |||||||||||||||  ||| || ||     |  ||| |    |||
     129 AGCTCTTCCAGACGGTGGCCGAGGGGCTGCGGCACGTGTACGCGCAGAAG 178

470 CTGCTGCCTCTGGAAGAGTATTACCGCTTCCACGAGTTCCACTCGCCCGC 519
         |||||||  |||||  || ||||||||||||||||||||||||||||||
     179 CTGCTGCCGCTGGAGGAGCACTATCGCTTCCACGAGTTCCACTCGCCCGC 228

520 CCTGGAAGATGCTGATTTCGACAACAAGCCCATGGTCCTGTTGGTGGGCC 569
         |||||  || |||||| ||||||||||||| ||||| || |||| ||||
     229 GCTGGAGGACGCTGACTTCGACAACAAGCCGATGGTGCTCCTGGTCGGCC 278

570 AGTACTCTACCGGCAAGACCACCTTCATCAGGTACCTGCTGGAACAGGAT 619
         |||||   |||||||||||||||||||| |   ||||| |  || || |
     279 AGTACAGCACCGGCAAGACCACCTTCATCCGCCACCTGATCGAGCAGGAC 328

620 TTTCCAGGCATGAGGATTGGGCCTGAGCCGACCACTGATTCCTTCATAGC 669
         || || || ||| | || ||||| |||| || || |||||||||| ||
     329 TTCCCGGGGATGCGCATCGGGCCGGAGCCCACCACCGACTCCTTCATCGC 378

670 AGTGATGCAGGGAGATGTGGAGGGGATCATTCCCGGGAATGCCTTGGTGG 719
         |  |||||| ||       |||||  |  ||||| || ||  ||  | |
     379 GGTCATGCACGGCCCCACCGAGGGCGTGGTGCCCGGCAACGCGCTCGTCG 428

720 TGGATCCAAAGAAACCCTTCAGAAAGCTCAACGCCTTTGGCAACGCCTTC 769
         ||||  ||   |    ||||||  | |||||||||||||| ||||||||
     429 TGGACCCGCGGCGCCCCTTCCGCAAGCTCAACGCCTTCGGCAACGCCTTC 478

770 CTGAACAGGTTTGTGTGTGCCCAGCTGCCCAACGCCGTGCTTGAAAGTAT 819
         || |||||||| ||||||||  ||||||| ||  || || ||  || ||
     479 CTCAACAGGTTCATGTGTGCACAGCTGCCCAACCCAGTACTGGACAGCAT 528

820 CAGTGTGATCGACACACCGGGGATCCTCTCTGGGGAGAAGCAGAGGATCA 869
         ||| |  || |||||  || ||||||| |||||||||||||| | ||||
     529 CAGCATCATTGACACTCCTGGGATCCTGTCTGGGGAGAAGCAGCGCATCA 578

870 GCCGAGGGTATGATTTTGCTGCGGTCCTCGAATGGTTTGCTGAGCGGGTG 919
         ||||||| ||||| ||||| || || || ||||| ||||| ||||| ||
     579 GCCGAGGTTATGACTTTGCGGCTGTCCTTGAGTGGTTCGCAGAGCGTGTG 628

920 GACCGAATTATCCTACTCTTCGACGCCCACAAGCTGGACATCTCCGATGA 969
         ||||| | |||  |  | |||||||||||||||||||||||||  || ||
     629 GACCGCATCATCTTGTTGTTCGACGCCCACAAGCTGGACATCTCAGACGA 678

970 GTTCTCAGAAGTCATCAAGGCTCTCAAGAACCATGAGGACAAGATGCGCG 1019
         ||||||||||||||||||||| | ||||  || |  || ||||||| ||
     679 GTTCTCAGAAGTCATCAAGGCCCTCAAAAATCACGAGGACAAGATCCGTG 728

1020 TAGTGTTGAACAAGGCTGACCAGATCGAGACCCAGCAGCTGATGCGAGTA 1069
         | ||| ||||||||||||||||||||||||||| |||||||||||||||
     729 TGGTGCTGAACAAGGCTGATCAGATCGAGACGCAGCAGCTGATGCGAGTA 778

1070 TACGGAGCCCTCATGTGGTCCCTGGGGAAGATCGTGAACACCCCCGAGGT 1119
         |||||  ||||||||||||||||||||||||| | |||||||||||||||
     779 TACGGGGCCCTCATGTGGTCCCTGGGGAAGATCATCAACACCCCCGAGGT 828

1120 GATCCGGGTCTACATTGGCTCCTTCTGGTCCCACCCACTCCTCATTCCCG 1169
         | || | ||||||||  |||||||||||||  ||||||  |  |   ||
     829 GGTCAGAGTCTACATCGGCTCCTTCTGGTCACACCCACTGCTCATCCCTG 878

1170 ACAACCGGAAGCTCTTTGAAGCTGAAGAGCAAGACTTGTTCAGAGACATT 1219
         ||||||||||| ||||| |||| || || ||| ||||  |||||||||
     879 ACAACCGGAAGTTCTTTGAGGCGGAGGAGCAGGACTTTTTCAAAGACATC 928

1220 CAGAGTCTACCCCGTAATGCTGCTCTTCGAAAGCTCAACGATCTCATCAA 1269
         |||    ||   | || ||  || || || |||||| | |||||||||||
     929 CAGTTTCTGCCGAGAAACGCCGCCCTCAGGAAGTTCAATGACCTCATCAA 978

1270 GAGAGCCCGGCTGGCCAAGGTCCACGCCTACATCATCAGCTCCTTGAAGA 1319
         |   | |||||||||||||||||| |||||||||||||| |||| ||||
     979 GCGGGCCAGGCTGGCCAAGGTCCATGCCTACATCATCAGTTCCCTCAAGA 1028

1320 AGGAGATGCCCTCAGTGTTTGGGAAGGACACCAAAAAGAAAGAACTGGTG 1369
         |||||||||||   || ||  |||| || | ||| ||| |||||||||
```

Fig. 19

```
1029 AGGAGATGCCCAATGTTTTCGGGAAAGAGAGCAAGAAGAAAGAGCTGGTG 1078

1370 AACAACCTGGCTGAGATCTATGGCCGGATTGAGCGAGAACACCAGATCTC 1419
     ||||||||||  |||||||||     ||| ||||| || ||||||||||
1079 AACAACCTGGGAGAGATCTACCAGAAGATCGAGCGGGAGCACCAGATCTC 1128

1420 CCCTGGAGACTTCCCCAACCTGAAGAAGATGCAGGACCAGCTGCAGGCCC 1469
     |  | || ||||||||  | ||||    |||||||||||| ||||||  |||||||
1129 CTCCGGCGACTTCCCAAGCCTGCGTAAGATGCAGGAACTCCTGCAGACCC 1178

1470 AGGACTTCAGCAAATTCCAGCCACTGAAGAGCAAGCTGCTGGAAGTGGTT 1519
     |||||||||||| ||||||  |    |||||   |||||||||||    ||
1179 AGGACTTCAGCAAGTTCCAGGCCTTGAAGCCCAAGCTGCTGGATACAGTG 1228

1520 GATGATATGCTGGCTCATGACATTGCCCAGCTCATGGTGCTGGTGCGCCA 1569
     |||||||||||||  | ||  || |  ||| |||||| ||||||||||||
1229 GATGATATGCTGGCCAACGATATAGCTCGGCTGATGGTGATGGTGCGCCA 1278

1570 GGAAGAGACCCAACGGCCTGTCCAGATGGTGAAGGGCGGAGCATTTGAGG 1619
     ||| ||| |||    |||     |||  ||||||||| || || ||||| |
1279 GGAGGAGTCCCTGATGCCCTCACAGGCTGTGAAGGGTGGTGCTTTTGATG 1328

1620 GAACCTTACAAGGCCCCTTCGGGCACGGCTATGGAGAGGGAGCTGGGGAG 1669
     | ||| | | || ||||| ||||| |||||  ||||| ||||| |||
1329 GCACCATGAATGGGCCCTTTGGGCATGGCTACGGCGAGGGGCTGGCGAG 1378

1670 GGCATCGATGATGCCGAGTGGGTGGTGGCGCGGGACAAGCCTATGTATGA 1719
     |||| |||||||   ||||||||  ||| |       |||||||| | |||||
1379 GGCATTGATGATGTTGAGTGGGTAGTTGGCAAGGACAAGCCCACCTATGA 1428

1720 TGAGATCTTCTACACCTTATCCCCAGTGGATGGCAAGATCACAGGTGCCA 1769
     ||||||||||||||| | || || ||  |  ||||||||||||||||| |
1429 TGAGATCTTCTACACACTGTCTCCTGTCAACGGCAAGATCACAGGTGCTA 1478

1770 ACGCCAAGAAGGAGATGGTGCGCTCCAAGTTGCCCAACAGCGTGCTGGGC 1819
     | ||||||||||||||||||| |||||| ||||||||||| |||||||||
1479 ATGCCAAGAAGGAGATGGTGAAGTCCAAGCTGCCCAACACAGTGCTGGGG 1528

1820 AAGATCTGGAAGCTAGCCGACATTGACAAGGATGGCATGTTGGATGACGA 1869
     ||||||||||||  | || ||  | |  |||||||||| ||||||||||
1529 AAGATCTGGAAGTTGGCAGATGTGGACAAGGATGGCCTGCTGGATGACGA 1578

1870 GGAGTTTGCCCTGGCCAACCACCTTATCAAAGTCAAGCTAGAGGGGCATG 1919
     ||||||||||||||||||||||||||||||| ||||||||||||||  | |
1579 GGAGTTTGCCCTGGCCAACCACCTTATCAAGGTGAAGCTAGAGGGCCACG 1628

1920 AGCTGCCCAGTGAGCTACCTGCCCACCTCCTCCCTCCATATAAGAGGAAA 1969
     |||||||| |  |||  ||  ||| |  ||  || |
1629 AGCTGCCCGCTGACCTTCCTCCACATCTCATT.................  1660
```

Fig. 19 (Cont.)

```
EHD2    1 MFSWVSKDARRKKEPELFQTVAEGLRHVYAQKLLPLEEHYRFHEFHSPAL  50 (SEQ ID NO:10)
          ||||. | ||||:||.||||.:||: .| |||||||:|||||||||||
EHD1    1 MFSWLGNDDRRKKDPEVFQTVSDGLKKLYKTKLLPLEEYYRFHEFHSPAL  50 (SEQ ID NO:5)

51 EDADFDNKPMVLLVGQYSTGKTTFIRHLIEQDFPGMRIGPEPTTDSFIAV 100
          ||||||||||||||||||||||||||:|:|||||||||||||||||||
       51 EDADFDNKPMVLLVGQYSTGKTTFIRYLLEQDFPGMRIGPEPTTDSFIAV 100

101 MHGPTEGVVPGNALVVDPRRPFRKLNAFGNAFLNRFMCAQLPNPVLDSIS 150
          | |  ||::|||||||||::|||||||||||||||.|||||| ||:|||
      101 MQGDVEGIIPGNALVVDPKKPFRKLNAFGNAFLNRFVCAQLPNAVLESIS 150

151 IIDTPGILSGEKQRISRGYDFAAVLEWFAERVDRIILLFDAHKLDISDEF 200
          :|||||||||||||||||||||||||||||||||||||||||||||||
      151 VIDTPGILSGEKQRISRGYDFAAVLEWFAERVDRIILLFDAHKLDISDEF 200

201 SEVIKALKNHEDKIRVVLNKADQIETQQLMRVYGALMWSLGKIINTPEVV 250
          ||||||||||||.||||||||||||||||||||||||||||:|||||:
      201 SEVIKALKNHEDKMRVVLNKADQIETQQLMRVYGALMWSLGKIVNTPEVI 250

251 RVYIGSFWSHPLLIPDNRKFFEAEEQDFFKDIQFLPRNAALRKFNDLIKR 300
          |||||||||||||||||||| ||||||| |:||| |||||||| |||||
      251 RVYIGSFWSHPLLIPDNRKLFEAEEQDLFRDIQSLPRNAALRKLNDLIKR 300

301 ARLAKVHAYIISSLKKEMPNVFGKESKKKELVNNLGEIYQKIEREHQISS 350
          ||||||||||||||||||.||||:.||||||||||| ||| :|||||||
      301 ARLAKVHAYIISSLKKEMPSVFGKDTKKKELVNNLAEIYGRIEREHQISP 350

351 GDFPSLRKMQELLQTQDFSKFQALKPKLLDTVDDMLANDIARLMVMVRQE 400
          ||||.|:|||: || ||||||| || ||| |||||.|||.|||:|||||
      351 GDFPNLKKMQDQLQAQDFSKFQPLKSKLLEVVDDMLAHDIAQLMVLVRQE 400

401 ESLMPSQAVKGGAFDGTMNGPFGHGYGEGAGEGIDDVEWVVGKDKPTYDE 450
          |. | | ||||||:|| :|| ||||||||||||||| |||| :||| |||
      401 ETQRPVQMVKGGAFEGTLQGPFGHGYGEGAGEGIDDAEWVVARDKPMYDE 450

451 IFYTLSPVNGKITGANAKKEMVKSKLPNTVLGKIWKLADVDKDGLLDDEE 500
          ||||||||.||||||||||||||:|||||.|||||||||:|||||:||||
      451 IFYTLSPVDGKITGANAKKEMVRSKLPNSVLGKIWKLADIDKDGMLDDEE 500

501 FALANHLIKVKLEGHELPADLPPHLIPPSKRRHE..        534
          ||||||||||||||||||.:|| ||:|| ||:
      501 FALANHLIKVKLEGHELPSELPAHLLPPYKRRKVSE        535
```

EH DOMAIN CONTAINING GENES AND PROTEINS

This is a continuation-in-part of U.S. application Ser. No. 09/026,898, filed Feb. 20, 1998 now abandoned.

FIELD AND BACKGROUND OF THE INVENTION

The present invention relates to eps15 homology (EH) domain containing proteins, to polynucleotide sequences encoding said EH domain containing proteins, to oligonucleotides and oligonucleotide analogs derived from said polynucleotide sequences, to a display library displaying short peptides derived from said EH domain containing proteins, to antibodies recognizing said EH domain containing proteins, to peptides or peptide analogs derived from said EH domain containing proteins, and to pharmaceutical compositions and methods of employing said peptides or peptide analogs, said oligonucleotides and oligonucleotide analogs, and/or said polynucleotide sequences to up-regulate or down-regulate clathrin coated pit mediated endocytosis and thereby insulin growth factor 1 receptor (IGF1 receptor) signaling.

Citation or identification of any reference in this section or in any other section of this application shall not be construed as an admission that such reference is available as prior art to the present invention.

Abbreviations used herein include AP—adaptor protein complex; BBS—Bardet-Biedl Syndrome; ECL—enhanced chemiluminescence; EGFR—epidermal growth factor receptor; EH—eps15 homology; Eps—epidermal growth factor receptor-pathway-substrate; EST—expressed sequence tag; GFP—green fluorescent protein; HRP—horseradish peroxidase; IGF1—insulin-like growth factor 1; ocd—osteochondrodystrophy; ORF—open reading frame; PBS—phosphate buffered saline.

The diverse effects growth factors have on cell proliferation, differentiation and metabolism are mediated by interaction with cell surface receptors. There are several receptor families which convey their ligand-induced signals through different intracellular mechanisms. One family of receptors posses tyrosine kinase activity (Darnell et al., 1995) and includes the EGF receptor, insulin receptor and the IGF1 receptor. Binding of these receptors to their ligands induces cascade of events, leading to sequestration of the ligand bound receptor in endocytic vesicles (Kirchhausen et al., 1997; Mukherjee et al., 1997; Warren et al., 1998). This process depends on the specific interaction of clathrin and the clathrin adaptor protein complex, AP-2, with specific accessory factors. It has been shown that the EGFR phosphorylates at least two proteins, eps15 and eps15R, after which each one of them may interact, through accessory proteins, with AP-2.(Benmerah et al., 1998; Coda et al., 1998). This interaction leads to endocytosis of the ligand bound EGFR. Pan1p, the yeast homologue of eps15, was also shown to function as a multivalent adaptor that coordinates protein—protein interactions essential for endocytosis (Wendland and Emr, 1998).

Ligand induced endocytosis is a regulated process, leading to the formation of clathrin coated pits containing the ligand bound receptor. The spontaneous polymerization of clathrin triskelions is thought to cause the pits to expand and eventually to form the clathrin coated vesicle. These vesicles loose their coat after endocytosis, forming the early endosome. Endocytosed receptors, after their dissociation from the ligand due to the low pH in the early endosome, are usually recycled to the plasma membrane or are destined to the lysosomes, were they are degraded. For EGF receptor, the phosphorylation of eps15 leads, most probably, to binding of at least another specific protein, epsin,(Chen et al., 1998) and this protein complex seems to recruit AP-2. (Iannolo et al., 1997)., which then binds to clathrin.

Eps15 and eps15R contain three domains: One is an N-terminal domain containing three repeats of the EH motif, directing protein—protein interactions through the amino acids NPF (asparagine-proline-phenylalanine, SEQ ID NO: 11) of target proteins. The EH domain spans about 100 amino acids, about 50% of which are conserved between different proteins containing this domain. EH domains are frequently present in multiple copies and might also include EF-hand calcium binding motifs. It has been shown that the second EH domain consists of a pair of EF hand motifs, the second of which binds tightly to $Ca^{2+}$. The NPF containing motif binds in a hydrophobic pocket of the EH domain, between two alpha helices, and the binding is mediated by a critical aromatic interaction (Benmerah et al., 1998; de Beer et al., 1998; Di Fiore et al., 1997; Fazioli et al., 1993; Schumacher et al., 1995; Tebar et al., 1997). A second domain contains heptad repeats, characteristic of coiled-coil structure, which directs dimerization (and most probably oligomerization). The third domain is C-terminal region and has a proline-rich region and a repeated DPF (aspartic acid-proline-phenylalanine, SEQ ID NO:12) motif. (Benmerah et al., 1998; Di Fiore et al., 1997; Fazioli et al., 1993; Schumacher et al., 1995; Tebar et al., 1997).

There is a growing number of EH-containing proteins, like intersectin .(Yamabhai et al., 1998) Ese1 and Ese2 (Sengar et al., 1999) and they all seem to be associated with the intracellular routing machinery (Di Fiore et al., 1997). Another EH containing protein is the Drosophila Dap160, a neural specific protein that anchors proteins required for endocytosis. (Roos and Kelly, 1998). It has been suggested that endocytosis is only one of several intracellular activities in which EH containing proteins participate and may also regulate (Coda et al., 1998).

Several proteins, containing NPF motifs, have been identified as interacting with eps15 and participating in clathrin coated pit mediated endocytosis, like: epsin (Chen et al., 1998) and dynamin,(Roos and Kelly, 1998).

While reducing the present invention to practice, two new and highly homologous genes isolated from both human and mouse, named EHD 1 (which is referred to in U.S. Pat. No. 09/026,898 as testiline and has the yet unpublished accession Nos. AF099011 for the human cDNA and AF099186 for the mouse cDNA) and EHD2 were cloned, sequenced, mapped, their expression characterized and function analyzed. The proteins encoded by the isolated genes contain an EH domain which, as described above, is known to modulate interactions with endocytic vesicles. Based on the pattern of the EHD1 and EHD2 genes expression and on their interaction with other cellular proteins it is concluded that the protein products of these genes participate in clathrin coated pit mediated endocytosis of IGF1 receptor, following its binding to its ligand.

SUMMARY OF THE INVENTION

According to one aspect of the present invention there is provided an isolated nucleic acid comprising a genomic, complementary or composite polynucleotide sequence encoding a polypeptide having an N-terminal region containing a nucleotide binding consensus site, a central coiled-coil structure and a C-terminal region including an eps15 homology (EH) domain. According to a preferred embodiment the polypeptide encoded by the polynucleotide participates in endocytosis processes.

The polynucleotide according to this aspect of the present invention preferably encodes a polypeptide which is at least 75% homologous to SEQ ID NOs:4, 5, 9 or 10 as determined using the BestFit software of the Wisconsin sequence analysis package, utilizing the Smith and Waterman algorithm, where gap creation penalty equals 8 and gap extension penalty equals 2.

According to preferred embodiments, the polynucleotide according to this aspect of the present invention encodes a polypeptide as set forth in SEQ ID NOs:4, 5, 9 or 10 or a portion thereof, preferably a portion which retains EHD1 or 2 activity.

Alternatively or additionally, the polynucleotide according to this aspect of the present invention is preferably hybridizable with SEQ ID NOs:1, 2, 3, 6, 7 or 8.

Hybridization for long nucleic acids (e.g., above 200 bp in length) is effected according to preferred embodiments of the present invention by stringent or moderate hybridization, wherein stringent hybridization is effected by a hybridization solution containing 10% dextrane sulfate, 1 M NaCl, 1% SDS and 5×10$^6$ cpm $^{32}$p labeled probe, at 65° C., with a final wash solution of 0.2×SSC and 0.1% SDS and final wash at 65° C.; whereas moderate hybridization is effected by a hybridization solution containing 10% dextrane sulfate, 1 M NaCl, 1% SDS and 5×10$^6$ cpm $^{32}$p labeled probe, at 65° C., with a final wash solution of 1×SSC and 0.1% SDS and final wash at 50° C.

Yet alternatively or additionally, the polynucleotide according to this aspect of the present invention is preferably at least 70% identical with SEQ ID NOs: 1, 2, 3, 6, 7 or 8 as determined using the BestFit software of the Wisconsin sequence analysis package, utilizing the Smith and Waterman algorithm, where gap weight equals 50, length weight equals 3, average match equals 10 and average mismatch equals −9. According to preferred embodiments the polynucleotide according to this aspect of the present invention is as set forth in SEQ ID NOs:1, 2, 3, 6, 7 or 8 or a portion thereof, said portion preferably encodes a polypeptide retaining EHD1 or 2 activity.

According to another aspect of the present invention there is provided a nucleic acid construct comprising the isolated nucleic acid described herein. According to a preferred embodiment the nucleic acid construct according to this aspect of the present invention further comprising a promoter for regulating expression of the isolated nucleic acid in a sense or antisense orientation.

Alternatively, the nucleic acid construct according to this aspect of the present invention further comprising a positive and a negative selection markers and may therefore be employed for selecting homologous recombination events, including, but not limited to, homologous recombination employed in knock-in and knock-out procedures.

Consequently, according to yet another aspect of the present invention there is provided a host cell or animal comprising a nucleic acid construct as described herein.

According to still another aspect of the present invention there is provided an oligonucleotide of at least 17 bases specifically hybridizable with the isolated nucleic acid described herein. Hybridization of shorter nucleic acids (below 200 bp in length, e.g. 17–40 bp in length) is effected by stringent, moderate or mild hybridization, wherein stringent hybridization is effected by a hybridization solution of 6×SSC and 1% SDS or 3 M TMACl, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 1–1.5° C. below the $T_m$, final wash solution of 3 M TMACl, 0.01 M sodium phosphate (pH 6.8), 1 mM EDTA (pH 7.6), 0.5% SDS at 1–1.5° C. below the $T_m$; moderate hybridization is effected by a hybridization solution of 6×SSC and 0.1% SDS or 3 M TMACl, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 2–2.5° C. below the $T_m$, final wash solution of 3 M TMACl, 0.01 M sodium phosphate (pH 6.8), 1 mM EDTA (pH 7.6), 0.5% SDS at 1–1.5° C. below the $T_m$, final wash solution of 6×SSC, and final wash at 22° C.; whereas mild hybridization is effected by a hybridization solution of a hybridization solution of 6×SSC and 1% SDS or 3 M TMACl, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 37° C., final wash solution of 6×SSC and final wash at 22° C.

According to an additional aspect of the present invention there is provided a pair of oligonucleotides each of at least 17 bases specifically hybridizable with the isolated nucleic acid described herein in an opposite orientation so as to direct exponential amplification of a portion thereof in a nucleic acid amplification reaction.

According to yet an additional aspect of the present invention there is provided a nucleic acid amplification product obtained using the pair of primers described herein.

According to still an additional aspect of the present invention there is provided an antisense oligonucleotide comprising a polynucleotide or a polynucleotide analog of at least 10 bases being hybridizable in vivo, under physiological conditions, with a portion of a polynucleotide strand encoding a polypeptide at least 75% homologous to SEQ ID NOs:4, 5, 9 or 10 as determined using the BestFit software of the Wisconsin sequence analysis package, utilizing the Smith and Waterman algorithm, where gap creation penalty equals 8 and gap extension penalty equals 2.

According to a further aspect of the present invention there is provided a pharmaceutical composition comprising the antisense oligonucleotide described herein and a pharmaceutically acceptable carrier.

According to still a further aspect of the present invention there is provided a ribozyme comprising the antisense oligonucleotide described herein and a ribozyme sequence fused thereto.

According to yet a further aspect of the present invention there is provided a recombinant protein comprising a polypeptide having an N-terminal region containing a nucleotide binding consensus site, a central coiled-coil structure and a C-terminal region including an eps15 homology (EH) domain, the polypeptide participates in endocytosis. Preferably, the polypeptide is at least 75% homologous to SEQ ID NOs:4, 5, 9 or 10 as determined using the BestFit software of the Wisconsin sequence analysis package, utilizing the Smith and Waterman algorithm, where gap creation penalty equals 8 and gap extension penalty equals 2. Most preferably the polypeptide includes at least a portion of SEQ ID NOs:4, 5, 9 or 10. Additionally or alternatively, the polypeptide according to this aspect of the present invention is preferably encoded by a polynucleotide hybridizable with SEQ ID NOs: 1, 2, 3, 6, 7 or 8 or a portion thereof under the any of the stringent or moderate hybridization conditions described above for long nucleic acids. Still additionally or alternatively, the polypeptide according to this aspect of the present invention is preferably encoded by a polynucleotide at least 70% identical with SEQ ID NOs: 1, 2, 3, 6, 7 or 8 or portions thereof as determined using the BestFit software of the Wisconsin sequence analysis package, utilizing the Smith and Waterman algorithm, where gap weight equals 50, length weight equals 3, average match equals 10 and average mismatch equals −9.

According to still a further aspect of the present invention there is provided a pharmaceutical composition comprising, as an active ingredient, the recombinant protein described herein and a pharmaceutical acceptable carrier.

According to another aspect of the present invention there is provided a peptide or a peptide analog comprising a stretch of at least 6 consecutive amino acids or analogs thereof derived from a polypeptide at least 75% homologous to SEQ ID NOs:4, 5, 9 or 10 as determined using the BestFit software of the Wisconsin sequence analysis package, utilizing the Smith and Waterman algorithm, where gap creation penalty equals 8 and gap extension penalty equals 2. Preferably, the peptide or a peptide analog according to this aspect of the present invention comprises a stretch of at least 6 consecutive amino acids or analogs thereof derived from SEQ ID NOs:4, 5, 9 or 10.

According to still another aspect of the present invention there is provided a display library comprising a plurality of display vehicles (such as phages, viruses or bacteria) each displaying at least 6 consecutive amino acids derived from a polypeptide at least 75% homologous to SEQ ID NOs:4, 5, 9 or 10 as determined using the BestFit software of the Wisconsin sequence analysis package, utilizing the Smith and Waterman algorithm, where gap creation penalty equals 8 and gap extension penalty equals 2. According to a preferred embodiment of this aspect of the present invention substantially every 6 consecutive amino acids derived from the polypeptide are displayed by at least one of the plurality of display vehicles, so as to provide a highly representative library. Preferably, the consecutive amino acids or amino acid analogs of the peptide or peptide analog according to this aspect of the present invention are derived from SEQ ID NOs:4, 5, 9 or 10.

According to still another aspect of the present invention there is provided an antibody comprising an immunoglobulin specifically recognizing a polypeptide at least 75% homologous to SEQ ID NOs:4, 5, 9 or 10 as determined using the BestFit software of the Wisconsin sequence analysis package, utilizing the Smith and Waterman algorithm, where gap creation penalty equals 8 and gap extension penalty equals 2. According to a preferred embodiment of this aspect of the present invention the antibody specifically recognizing the polypeptides set forth in SEQ ID NOs:4, 5, 9 or 10. The antibody according to this aspect of the present invention can be, for example, a polyclonal antibody, a monoclonal antibody, a humanized antibody, a single chain antibody or an immunoreactive derivative (e.g., portion) of an antibody.

According to yet another aspect of the present invention there is provided a pharmaceutical composition comprising, as an active ingredient, an agent for regulating an endogenous protein activity in vivo, the endogenous protein being at least 75% homologous to SEQ ID NOs:4, 5, 9 or 10 as determined using the BestFit software of the Wisconsin sequence analysis package, utilizing the Smith and Waterman algorithm, where gap creation penalty equals 8 and gap extension penalty equals 2.

According to yet another aspect of the present invention there is provided a method of regulating an endogenous protein activity in vivo the method comprising the steps of administering an agent for regulating the endogenous protein activity in vivo, the endogenous protein being at least 75% homologous to SEQ ID NOs:4, 5, 9 or 10 as determined using the BestFit software of the Wisconsin sequence analysis package, utilizing the Smith and Waterman algorithm, where gap creation penalty equals 8 and gap extension penalty equals 2.

According to further features in preferred embodiments of the invention described below, the agent indirectly serves for regulating. IGF1 receptor cell signaling via altered clathrin coated pit mediated endocytosis.

According to still further features in the described preferred embodiments the agent serves for upregulating the activity.

According to still further features in the described preferred embodiments the agent indirectly serves for downregulating IGF1 receptor cell signaling via upregulated clathrin coated pit mediated endocytosis.

According to still further features in the described preferred embodiments the agent serves for upregulating clathrin coated pit mediated endocytosis.

According to still further features in the described preferred embodiments the agent includes an expressible sense polynucleotide at least 70% identical with SEQ ID NOs: 1, 2, 3, 6, 7 or 8 as determined using the BestFit software of the Wisconsin sequence analysis package, utilizing the Smith and Waterman algorithm, where gap weight equals 50, length weight equals 3, average match equals 10 and average mismatch equals −9.

According to still further features in the described preferred embodiments the agent includes a polypeptide at least 75% homologous to SEQ ID NOs:4, 5, 9 or 10 as determined using the BestFit software of the Wisconsin sequence analysis package, utilizing the Smith and Waterman algorithm, where gap creation penalty equals 8 and gap extension penalty equals 2.

According to still further features in the described preferred embodiments the agent serves for downregulating the activity.

According to still further features in the described preferred embodiments the agent indirectly serves for upregulating IGF1 receptor cell signaling via downregulated clathrin coated pit mediated endocytosis.

According to still further features in the described preferred embodiments the agent includes an expressible antisense polynucleotide at least 70% identical with SEQ ID NOs: 1, 2, 3, 6, 7 or 8 as determined using the BestFit software of the Wisconsin sequence analysis package, utilizing the Smith and Waterman algorithm, where gap weight equals 50, length weight equals 3, average match equals 10 and average mismatch equals −9.

According to still further features in the described preferred embodiments the agent includes an antisense oligonucleotide which includes a polynucleotide or a polynucleotide analog of at least 10 bases which is hybridizable in vivo, under physiological conditions, with a portion of a polynucleotide strand encoding a polypeptide at least 75% homologous to SEQ ID NOs:4, 5, 9 or 10 as determined using the BestFit software of the Wisconsin sequence analysis package, utilizing the Smith and Waterman algorithm, where gap creation penalty equals 8 and gap extension penalty equals 2.

According to still further features in the described preferred embodiments the agent includes a peptide or a peptide analog representing a stretch of at least 6 consecutive amino acids or analogs thereof derived from a polypeptide at least 75% homologous to SEQ ID NOs:4, 5, 9 or 10 as determined using the BestFit software of the Wisconsin sequence analysis package, utilizing the Smith and Waterman algorithm, where gap creation penalty equals 8 and gap extension penalty equals 2.

The present invention successfully addresses the shortcomings of the presently known configurations by providing new means to treat diseases or conditions associated with too high or alternatively too low IGF1 receptor signaling.

BRIEF DESCRIPTION OF THE DRAWINGS

The file of this patent contains at least one drawing(s) executed in color photograph. Copies of this patent with color photograph(s) will be provided by the Patent and Trademark Office upon request and payment of necessary fee.

FIGS. 5a–b demonstrates analysis of EHD1 RNA. (5a)—RNA was extracted from a mouse cell line (CLL-226), electrophoresed through a formaldehyde-agarose gel, blotted and hybridized with different $^{32}$P-labeled human EHD1 cDNA fragments, depicted under the hybridization results. Each fragment represents its actual size relative to the EHD1 cDNA size, shown below. The number of RNA species a fragment identifies is described by the number of fragments. (5b)—RNA extracted as above was subjected to RT-PCR using the 3'-RACE kit, as recommended by the supplier (RI+) with the commercial primer AUP and the EHD1 specific primer GSP. The reaction mix was subjected to a second round of PCR with the 3' primer supplied with the kit (AUP) and a 5' nested primer (Npr). M—DNA markers. (RI–)—no RT control. C—no RNA control.

FIGS. 7a–f demonstrate immunohistochemical staining of mouse organs. Several mouse organs were fixed, embedded in paraffin and sections were prepared. The sections were reacted with the anti human EHD1 antibodies prepared against the bacterial expressed sequences (7a, 7c, 7e) or with preimmune serum (7b, 7d, 7f), as described in the Materials and Experimental Methods section. After washing, the slides were reacted with horseradish peroxidase conjugated goat anti-rabbit antibodies. The slides were then stained with methylene blue to visualize cells. Magnification:×400. 7a–b—testis; 7c–d-retina; 7e–f—-adipocytes. SG—spermatogonia; SC—spermatocytes; RCL—outer layer of rods and cones; NL—internal nuclear layer; GL—ganglion layer; AD—adipocytes.

FIGS. 8a–g demonstrate EHD1 expression in mouse embryo. a 15.5 days post conception (dpc) mouse embryo was fixed, embedded in paraffin and sagital sections were prepared. The sections were reacted with the anti human EHD1 antibodies prepared against the bacterial expressed sequence (8a, 8c, 8e) or with preimmune serum (8b, 8d, 8f), as described in the Materials and Experimental Methods section. After washing the slides were reacted with horseradish peroxidase conjugated goat anti-rabbit antibodies. The slides were then stained with methylene blue to visualize cells. Magnification:×400. C—spine structure containing chondrocytes; H—heart; L—liver; B-bone. (8g)—10.5 dpc mouse embryo was fixed in 4% paraformaldehyde, treated with proteinase K, and following prehybridization, it was hybridized with a dig-labeled mouse EHD1 RNA probe. The embryo was washed, blocked and reacted with anti alkaline phosphatase conjugated dig antibodies, after which it was reacted with BM purple as a substrate. LB—limb bud; MA—mandible; SC—condensation of sclerotomic material; HY—hyoid; OC—occipital.

FIG. 14 demonstrates partial DNA sequence of ocd and C3H derived EHD1 cDNAs (SEQ ID NOs. 13 and 2, respectively). Sequence around the initiator methionine (underlined) is depicted. Sequence alterations are shown in bold letters.

FIG. 18 demonstrates sequence homology between mouse EHD1 and mouse EHD2. The mouse EHD1 and EHD2 cDNA sequences were compared using the GCG package, version 9.0, bestfit program, as further described herein. The initiator methionine (ATG) and the terminator are underlined.

FIG. 19 demonstrates sequence homology between mouse EHD1 and mouse EHD2 coding regions. The mouse EHD1 and EHD2 coding regions were compared using the GCG package, version 9.0, bestfit program. The initiator methionine (ATG) and the terminator are underlined.

FIG. 20 demonstrates sequence homology between the mouse EHD1 and EHD2 proteins. The mouse EHD1 and EHD2 proteins were compared using the GCG package, version 9.0, bestfit program, after their translation.

Figure 21:
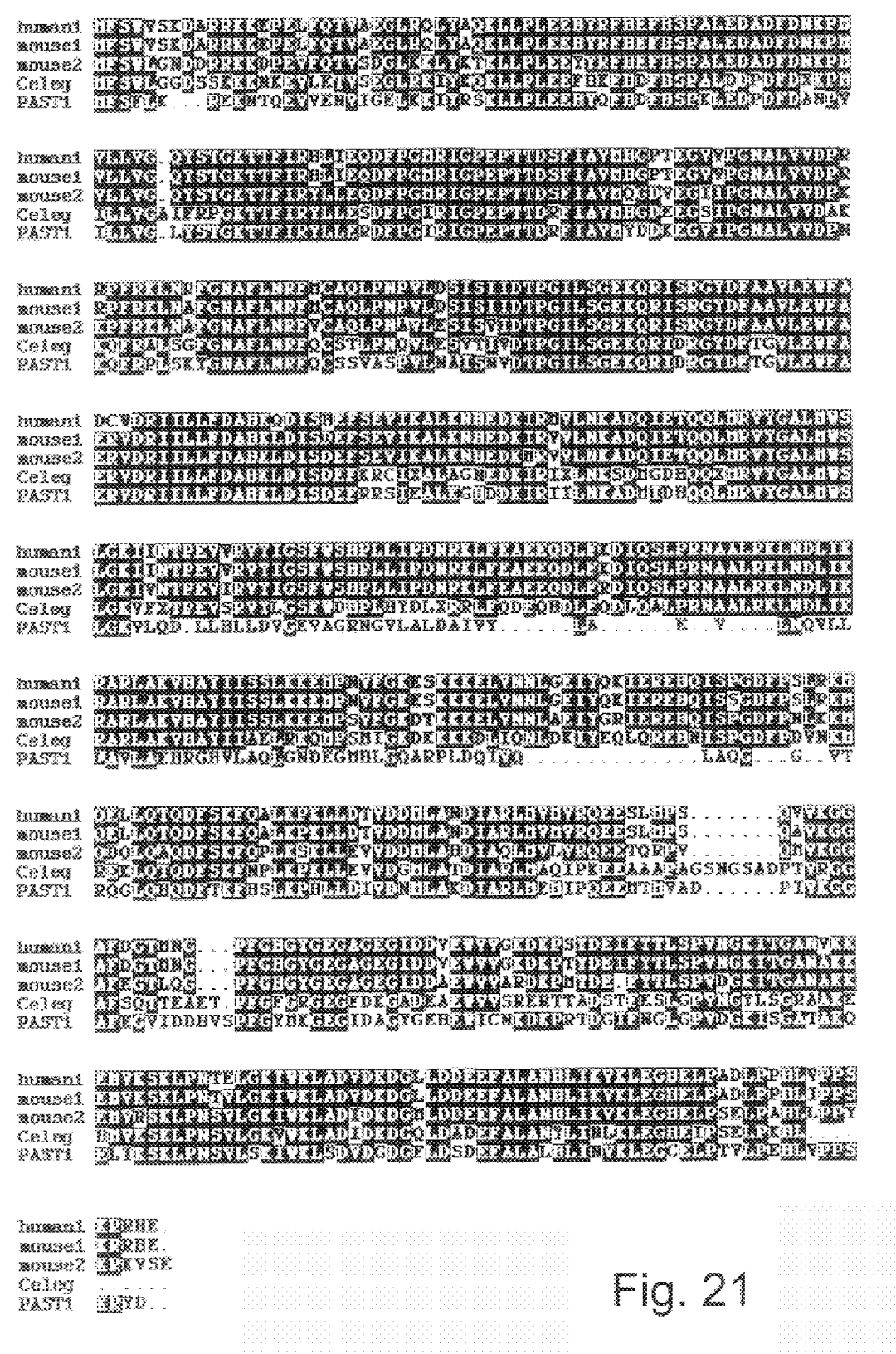

FIG. 21 demonstrate multiple alignment of several EHD proteins. Identical amino acids are shaded with black, similar—with gray. Accession numbers are as follows: human EHD1 (human1, SEQ ID NO:4): AF09901 1; mouse EHD1 (mouse1, SEQ ID NO:5): AF099186; mouse EHD2 (mouse2, SEQ ID NO:10), C. elegans (celeg, SEQ ID NO:14) ESTs—D69920, yK540g1.5, D69237, C69242, C60364, C47739; Drosophila PAST-1 (SEQ ID NO:15)—U70135.

DESCRIPTION OF THE PREFERRED EMBODIMENTS

Figure 1:
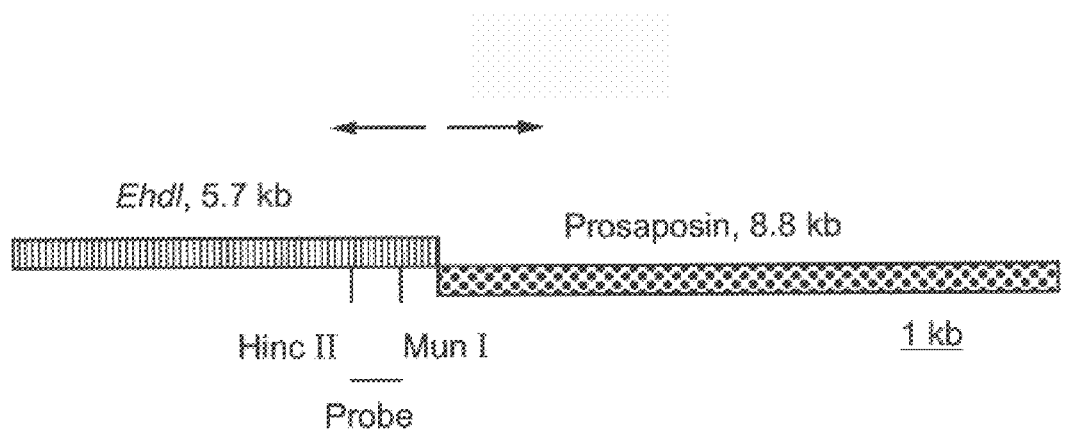
FIG. 1. illustrates a mouse genomic fragment isolated from a ICR/SWISS mouse genomic library (liver genomic DNA in EMBL3, Promega, USA) with a mouse prosaposin cDNA probe.

The present invention is of (i) eps15 homology (EH) domain containing proteins; (ii) polynucleotide sequences encoding said EH domain containing proteins; (iii) oligonucleotides and oligonucleotide analogs derived from said polynucleotide sequences; (iv) a display library displaying short peptides derived from said EH domain containing proteins; (v) antibodies recognizing said EH domain containing proteins; (vi) peptides or peptide analogs derived from said EH domain containing proteins; and (vii) pharmaceutical compositions; and (viii) methods of employing said peptides or peptide analogs, said oligonucleotides and oligonucleotide analogs, and/or said polynucleotide sequences to up-regulate or down-regulate clathrin coated pit mediated endocytosis and thereby insulin growth factor 1 receptor (IGF1 receptor) signaling.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The isolation and characterization of a new gene family is described herein. One of these genes, which is highly expressed in testis, was designated EHD1 and its closely related gene designated EHD2.

EHD1 is identical to h-PAST (GeneBank accession No. AF001434). Both EHD1 and EHD2 are homologous to the Drosophila PAST-1 (putative acheate scute target, GeneBank accession No. U70135) and several ESTs derived from C. briggsie, C. elegans, mouse and rice. The predicted evolutionary structural conservation of EHD1 and EHD2 is remarkable and likely points to their general biological importance.

Northern blot analysis indicated the existence of two EHD 1 RNA species in mouse and three RNA species in humans. It was demonstrated that in the mouse there are also three species that were not resolved under the conditions used for the RNA gel electrophoresis. 3'-RACE results indicated that the two mouse EHD 1 RNA species result from use of two polyadenylation signals, which are 1600 nucleotides apart. RT-PCR experiments indicated the existence of a third mRNA species, which results from exon 3 skipping.

Results of in vitro transcription-translation experiments, as well as transfection of COS cells with vectors expressing the entire open reading frame indicated that the human EHD1 protein is 62 kDa. Sub cellular localization experiments have indicated that EHD1, as a GFP-EHD1 fusion protein, co-localized with transferrin containing endocytic vesicles. EHD1 was present in other cellular structures, like the Golgi apparatus, as well.

Immunohistochemical analyses showed EHD1 expression in the male germ cells, in adipocytes and in several retinal layers and to a lesser extent, in the uterus, in skeletal muscle and kidney. During embryogenesis, EHD1 expression was already detectable at day 9.5 in the limb buds and at day 10.5 it was very clear in the limb buds, sklerotomes, at various elements of the branchial apparatus (mandible and hyoid) and in the occipital region. At day 15.5, EHD1 expression peaked in cartilage, preceding hypertrophy and ossification. Apparently, EHD1 is highly and specifically expressed in either mesenchymal derived cells or germ cells, known to be induced by IGF1 (Dealy and Kosher, 1996; Frade et al., 1996; Groigno et al., 1996; Lok et al., 1996; Lorenzo et al., 1995; Tardif et al., 1996; Villalpando et al., 1996; Yamamura et al., 1996).

IGF1 has been shown to be an important anabolic modulator of cartilage metabolism. Its autocrine/paracrine interaction with other growth factors regulate the rate of chondrocyte proliferation, matrix protein synthesis and terminal differentiation and mineralization.(Di Battista et al., 1997; Hill and Logan, 1992). IGF1 induces an increase in intracellular calcium concentration in cultured chondrocytes. (Poiraudeau et al., 1997). Adult mice homozygous for a targeted mutation of the IGF1 gene are infertile dwarfs. The testes of such mice are somewhat reduced in size with spermatogenesis only at 18% of normal levels (Baker et al., 1996). It has been directly shown that IGF1 induces type A spermatogonia differentiation in mouse testicular fragments. (Tajima et al., 1995).

EHD1 has an EH (eps15 homology) domain shown to be an important motif in proteins involved in protein—protein interactions and in intracellular sorting.(Di Fiore et al., 1997). Eps15 was characterized as a protein associated with the plasma membrane adaptor complex, AP-2, and it plays a role in endocytosis.(Benmerah et al., 1998). Several proteins with an NPF containing motif, through which they interact with the EH domain of eps15 like proteins, have been identified. They include, for example, dynamin (Roos and Kelly, 1998) and epsin (Chen et al., 1998). There are three rat dynamin genes, with each gene expressing at least four different alternatively spliced forms. It seems that the different dynamin forms are localized to distinct cytoplasmic or membrane compartments. (Cao et al., 1998).

It is worth noting that there are at least two human EHD1 genes (EHD1 and is nearly identical sequence EHD2), each expressing several mRNAs. Some of these mRNA forms may encode different EHD1 isoforms, which may be distributed differently in the cells.

Taking the results presented herein together with the published data on EH-containing proteins, it is believed that the 62 kDa EHD 1 isoform is an IGFIRS (insulin-like growth factor 1 receptor substrate), which mediates IGF1 receptor endocytosis through interaction with an adaptor protein complex.

Since EHD1 seems to be localize in other cellular structures beside the endocytic vesicles, like Golgi derived vesicles, another isoform may be involved in other cellular processes as well. It is believed that the protein—protein interaction mediated by EHD1 is regulated via $Ca^{2+}$ dependent nucleotide binding. Thus, EHD1, like eps15. (Carbone et al., 1997), is believed to be a multifunctional binding protein that serves pleiotropic functions within the cell.

EHD1 was mapped to the centromeric end of mouse chromosome 19. An STS (GeneBank accession No. 629339) which represents the 3' untranslated region of EHD 1 was mapped by the Stanford Radiation Hybrid Center to human 11q13, which shows conserved synteny with proximal mouse Chromosome 19. On the basis of its expression pattern and chromosomal localization, human diseases linked to human chromosome 11q13, that are associated with gonad abnormalities, bone abnormalities and obesity were searched for. One such candidate was the Bardet-Biedl syndrome, type 1. Bardet-Biedl is an autosomal recessive genetic disease characterized by mental retardation, pigmentary retinopathy, polydactily, obesity and hypogonadism. The disease has been linked to five different loci on: chromosome 11 (BBS1) (Leppert et al., 1994), chromosome 16 (BBS2), (Kwitek-Black et al., 1993), chromosome 3 (BBS3) (Sheffield et al., 1994), chromosome 15 (Carmi et al., 1995) and chromosome 2 (Young et al., 1998). However, sequencing the ORF and all the exon-intron boundaries from BBS1 patients did not reveal any mutation in their EHD1 gene.

In the mouse, EHD1 may be associated with osteochondrodystrophy, ocd (Sweet and Bronson, 1991). Ocd is an autosomal recessive mouse mutation. The mutant homozygotes suffer from reduced body size, a short, slightly domed head, supination of the forefeet, disproportionately shortened long bones of the limbs and a short thickened tail. Homozygous females are fertile while homozygous males have never sired litters, but their testes appear histologically normal and contain sperm. Histological studies of the bones of mutants showed that the epiphyses were thinner than in normal littermates and the columnar organization of the proliferative zone of the cartilage was disorganized.

As mentioned, a mouse EHD1 homologue, termed EHD2 (EH containing domain 2) have also been isolated and characterized. There is 56.9% nucleotides identity between the EHD1 and the EHD2 cDNAs, 80.1% nucleotides identity between their coding regions and 84.6% homology between the two predicted proteins. Like EHD1, EHD2 protein has a central coiled-coil motif and a C-terminal region with an EH module, which participates in protein—protein interactions. Whereas the EHD1 transcripts are highly expressed in testes and found in other tissues as well, the EHD2 transcript was so far detected only in brain and kidney. EHD2 contains a polymorphic CA repeat in its 3' untranslated region (UTR), which was used to map the EHD2 gene to mouse chromosome 17q41.49–43.60. This places the human gene, by synteny, to human chromosome 2p. A partial sequence of the human EHD2 cDNA, which also contains a polymorphic CA repeat at its 3' UTR was also isolated.

Table 1 below summarizes the sequences so far isolated and correlates these sequences with the Sequence Listing that follows:

TABLE 1

| Gene | Type | Source | SEQ ID NO: | Remarks |
|---|---|---|---|---|
| EHD1 | cDNA | human | 1 | |
| EHD1 | cDNA | mouse | 2 | |
| EHD1 | genomic DNA | mouse | 3 | |
| EHD1 | protein | human | 4 | |
| EHD1 | protein | mouse | 5 | |
| EHD2 | cDNA | mouse | 6 | |
| EHD2 | cDNA | human | 7 | 5'sequence missing |
| EHD2 | genomic DNA | mouse | 8 | exons 1-2 sequence missing |
| EHD2 | protein | human | 9 | N terminus sequence missing |
| EHD2 | protein | mouse | 10 | |

Based on the homology between the two proteins and their mode of expression, it is argued that both EHDs fulfill the same function in different cells and/or at different developmental stages.

It is interesting to note that transgenic mice overexpressing IGF1 resulted in an increase in body weight (Mathews et al., 1988; Mathews et al., 1988), while animals lacking IGF1 have a growth retardation (Liu et al., 1993), resembling the body weight defect present in BBS type 1 and osteochondrodystrophy, respectively.

As mentioned above, it seems that all the cells expressing EHD1 respond to IGF1 (Dealy and Kosher, 1996; Frade et al., 1996; Groigno et al., 1996; Lok et al., 1996; Lorenzo et al., 1995; Tardif et al., 1996; Yoshimura et al., 1996; Yoshinaga, 1994). Insulin like growth factor 1 (IGF1) is a hormone that evokes signal cascade involving activation of phospholipase C. It is structurally and functionally a hormone related to insulin. They both produce similar biological activities such as metabolic and growth promoting action (Kadowaki et al., 1996). They do so by binding to their receptors which also share similarities in both structure and function such as tyrosine specific protein kinase. EHD1 expressing cells, beside the germ cells which are unique in origin (Yoshinaga, 1994) are mesodermal in origin (Caplan, 1994). They seem to fall into two categories: cells in which IGF1 has a mitogenic effect like cartilage cells or germ cells and cells in which IGF1 has a metabolic action like: adipocytes, retinal cells or the granulosa cells of the ovaries.

Since the IGF1 receptor is responsible for mediating IGF1 induced mitogenic effects and transforming potential of many cells, the overexpression of the IGF1 receptor in a large array of cancers and cancer derived cell lines was predicted. A large, and a growing number, of tumors overexpress IGF1 receptor including: lung, breast, thymoma, gastric, colon, thyroid, hepatoma, pancreas, endometrial, neural, choriocarcinoma, Ewing, leukemias, erythroleukemia and osteosarcoma (LeRoith et al., 1995; Werner, 1998).

Overexpression of insulin-like growth factor-1 receptor (IGF1 receptor) correlates with poor prognosis and local recurrence (Dunn et al., 1998; Mandel et al., 1995; Parisot et al., 1999; Strohm et al., 1998). The 5-year survival rate for women with metastatic breast cancer and high IGF1 receptor levels is only 25–30 %. Thus, the need to improve treatment is apparent.

Dunn et al., (1998) addressed whether functional impairment of IGF1 receptor affects adhesion, invasion, and metastasis of breast cancer. Impairment of IGF1 receptor function was achieved by transfecting a dominant negative form of the receptor, termed 486stop, into MDA-MB-435 metastatic breast cancer cells. The protein product of 486stop was secreted extracellularly, resulting in a bystander effect. Cellular adhesion to laminin and collagen was inhibited by more than 80%. Furthermore, 486stop inhibited insulin-like growth factor-I-stimulated invasion through collagen IV by 75%. It also inhibited the invasion of MDA-MB-231 cells across collagen IV by 80%. Finally, MDA-MB-231 cells grown in the presence of the dominant negative IGF1 receptor were 30% more sensitive to Taxol-induced cell death. Growth in soft agar was suppressed by 486stop, but growth in monolayer was unaffected. When injected into the mammary fat pad, 486stop did not significantly suppress growth of the primary tumor, but metastasis to the lungs, livers, lymph nodes, and lymph vessels was significantly decreased compared to the vector control.

In conclusion, inhibition of IGF1 receptor resulted in suppression of adhesion, invasion, and metastasis, providing a mechanistic rationale for targeting IGF1 receptor in the treatment of metastatic breast cancer.

In the case of cancers, EHD1 overexpression and thus endocytosis should lower the rate of IGF1 signaling and suppress adhesion, invasion, and metastasis.

It has been shown recently that several human genes encoding endocytosis-related proteins are involved in chromosomal translocations in hematopoietic malignancies (Floyd and de Camilli, 1998). The human eps15, designated AF-1p was found to induce transformation when overexpressed in NIH3T3 cells. It was also found as a fusion protein with the ALL1/HRX gene product in two human myeloid leukemias. As a result of a t(11;19)(q23;p13) translocation, the N terminal domain of ALL1/HRX was fused to the C terminal domain of AF-1p. The fused protein did not contain an EH domain (all three EH domains of AF-1p are contained in the N-terminal domain) but could probably compete with the normal AF-1p on binding to AP-2, thus lowering endocytosis efficiency and allowing longer signaling intervals. The EEN gene, which encodes human SH3p8, was identified at the t(11;19)(q23;p13) translocation in a case of acute myeloid leukemia. This translocation resulted in a fusion protein that contained the N-terminus of ALL1/HRX and the C terminal domain of SH3p8. The SH3p8 has been shown to bind to dynamin and synaptojanin through their SH3 domains. The CALM gene, which encodes a non-neuronal form of AP180 protein that binds to AP-2 clathrin is the target of the t(10,11)(p13;q14) translocation in the U937 human cell line. As a result a fusion protein was formed containing almost the full-length CALM protein with the last four amino acids replaced with amino acids 81–1027 of the AF-10. In all theses fusion proteins the normal function in endocytosis could be abrogated. Therefore, mutated or altered expression of proteins participating in endocytosis could affect the control of cell proliferation, thus leading to malignancy. Since EHD1 was mapped to human 11q13, finding translocations in this region, associated with malignancies (most probably hematopoietic) will be pursued. Thus far, searches in the available human gene maps failed to identify translocations and other chromosomal changes associated with human 11q13.

In addition, abnormal expression or mutations of some endocytosis related proteins have been reported in human cancers (Floyd and DeCamilli, 1998).

The known endocytosis proteins and their involvement in cancer are summarized in Table 2 below:

TABLE 2

| ENDOCYTOS IS PROTEIN | KNOWN INTERACTIONS | CONNECTION TO CANCER |
| --- | --- | --- |
| Eps15 (AF-1p) | Target of EGF receptor phosphorylation; binds to AP-2 and synaptojanin. | Translocated in leukemia. |
| Endophilin I, II, III EEN-human SH3p8 | SH3 containing proteins; bind to dynamin and synaptojanin. | EEN translocation in leukemia |
| Amphiphysin | SH3 containing proteins, bind to dynamin and synaptojanin; bind to clathrin and AP-2. | Overexpressed in a subset of breast cancers; auto- antigen; reduced or absent in several solid tumors. |
| AP180 | Binds to clathrin, AP-2, inositol polyphosphates and phosphoinositides. | Translocated in lymphoma and several forms of leukemia. |
| HIV-1 Nef gene product | Binds to AP-2, and CD4 to mediate endocytosis. | Involved in the pathogenesis of AIDS |

IGF1 and IGF-2 are factors regulating metabolism, mitogenesis, differentiation and apoptosis. The IGF1 receptor activates divergent signaling pathways in different cells and tissues by phosphorylating multiple cellular proteins including receptor cellular substrate 1 and 2 (IRS 1, IRS2) as a first step in initiating the cascade of signal transduction (the On pathway). Other proteins like EHD1 may modulate this activity by ligand induced endocytosis (the OFF pathway).

IGF1 promotes the propagation of cancer cells through autocrine and paracrine mechanisms. Excessive activity of the IGF ligands and IGF1 receptor has been suggested as factors in tumorigenesis. In breast cancer cells, lung carcinoma and prostate cancer, levels of IGF1, IGF1 binding proteins and IGF1 receptors serve as prognostic markers. Recently, IGFs were demonstrated as potent mitogens for a variety of cancer cells in vitro, including breast cancer cells (Lee et al., 1997; Gebauer et al., 1998; Jackson et al., 1998; Torrisi et al., 1998; Stoll, 1997), prostate cancer cells, colon cancer cells, bladder carcinoma cells, osteosarcoma cells and lung carcinoma cells (Li et al., 1998; Chan et al., 1998; Long et al., 1998; Haltia et al., 1997; Takigawa 1997).

In obese children growth hormone secretion is impaired (Radetti et al., 1998). In these subjects, therefore, nutritional factors and insulin may contribute to sustain normal growth also by modulating several components of the IGF1 GFBP system. One of the genes impaired in obese mice is leptin. Leptin is a peptide hormone secreted by fat cells that acts in the brain to suppress feeding (nutrient uptake) and stimulate metabolism (energy expenditure) (Erickson et al., 1996). There is a complex association between leptin and IGF1 serum levels. In rat ovary cells it was shown that increasing serum leptin concentrations inhibit IGF1 induced FSH-stimulated E2 production by granulosa cells (Zachow and Magoffin, 1997). In human, serum leptin levels were shown to decrease as a result of elevation in IGF1 levels (Fouque et al., 1998). Since leptin levels, and therefore food uptake, is influenced by IGF1, most probably through induction of the signaling cascade, abrogation of this cascade, by enhanced endocytosis, for example, should change leptin levels and may influence body weight. These data suggest that excess GH/insulin-like growth factor I reduces serum leptin levels by reducing body fat mass and/or by unknown mechanisms. Thus in the case of obesity endocytosis of IGF1 receptor should be enhanced to decrease IGF1 levels in the serum and to elevate leptin levels.

Osteoporosis, increasingly recognized disease, both in women and men, is associated with low bone mass. Bone mass is largely genetically determined, but environmental factors also contribute. Greater muscle strength and physical activity are associated with higher bone mass, while radial bone loss is greater in cigarette smokers or those with a moderate alcohol intake. Sex hormones have important effects on bone physiology. In men, there is no abrupt cessation of testicular function or 'andropause' comparable with the menopause in women; however, both total and free testosterone levels decline with age. A common secondary cause of osteoporosis in men is hypogonadism. There is increasing evidence that estrogens are important in skeletal maintenance in men as well as women. Gastrointestinal disease predisposes patients to bone disease as a result of intestinal malabsorption of calcium and colecalciferol (vitamin D). Hypercalciuria and nephrolithiasis, anticonvulsant drug use, thyrotoxicosis, immobilization, liver and renal disease, multiple myeloma and systemic mastocytosis have all been associated with osteoporosis. It is possible that low-dose estrogen therapy or specific estrogen receptor-modulating drugs might increase BMD.

Men with idiopathic osteoporosis have low circulating insulin-like growth factor-1 (IGF1; somatomedin-1) concentrations, and IGF1 administration to these men increases bone formation markers more than resorption markers. Studies of changes in BMD with IGF1 treatment in osteoporotic men and women are underway. Osteoporosis in men will become an increasing worldwide public health problem over the next 20 years, so it is vital that safe and effective therapies for this disabling condition become available. Effective public health measures also need to be established and targeted to men at risk of developing the disease (Ebeling, 1998).

Since IGF1 administration to men with osteoporosis increases bone formation markers more than resorption markers, lowering the expression of components participating in IGF1 receptor should be considered as well. In this case, decreasing the EHD1 levels will elongate IGF1 effects and will increase bone formation.

Thus, according to one aspect of the present invention there is provided an isolated nucleic acid comprising a genomic, complementary or composite polynucleotide sequence encoding a polypeptide having an N-terminal region containing a nucleotide binding consensus site, a central coiled-coil structure and a C-terminal region including an eps15 homology (EH) domain.

As used herein in the specification and in the claims section that follows, the phrase "complementary polynucleotide sequence" includes sequences which originally result from reverse transcription of messenger RNA using a reverse transcriptase or any other RNA dependent DNA polymerase. Such sequences can be subsequently amplified in vivo or in vitro using a DNA dependent DNA polymerase.

As used herein in the specification and in the claims section that follows, the phrase "genomic polynucleotide sequence" includes sequences which originally derive from a chromosome and reflect a contiguous portion of a chromosome.

As used herein in the specification and in the claims section that follows, the phrase "composite polynucleotide sequence" includes sequences which are at least partially complementary and at least partially genomic. A composite sequence can include some exonal sequences required to encode the polypeptide having the N-terminal region containing a nucleotide binding consensus site, the central coiled-coil structure and the C-terminal region including an eps15 homology (EH) domain, as well as some intronic sequences interposing therebetween. The intronic sequences can be of any source, including of other genes, and typically will include conserved splicing signal sequences. Such intronic sequences may further include cis acting expression regulatory elements.

As used herein in the specification and in the claims section that follows, the phrase "N-terminal region containing a nucleotide binding consensus site" refers to a stretch of contiguous amino acids present at the amino terminal portion of a polypeptide which include ATP/GTP binding domain (GxxxxGKTxxxxxxV, SEQ ID NO:16).

As used herein in the specification and in the claims section that follows, the phrase "central coiled-coil structure" includes, as well known in the art, polypeptide sequences which direct dimerization and/or oligomerization and are present in a central portion of a polypeptide. Examples for dimerization via parallel and antiparallel interactions through coiled-coil domains of proteins have been shown in many systems, including both cellular and viral proteins (see, Callaghan et al., 1999, Wendland and Emr, 1998 and Skehel and Wiley 1998). Mutations within such domains affect protein self dimerization as was shown by crosslinking experiments in vitro. Coiled-coil domains are found in other proteins in context with other protein domains such as for example zinc finger domains, calmodulin binding motifs and others. In all cases, the coiled-coil domain is associated with protein—protein interaction and is involved in membrane trafficking (Corvera and Czech 1998).

As used herein in the specification and in the claims section that follows, the phrase "C-terminal region including an eps15 homology (EH) domain" includes a stretch of contiguous amino acids present at the carboxy terminal portion of a polypeptide which include an epidermal growth factor receptor-pathway-substrate homology domain which coordinates protein—protein interactions essential for endocytosis through, for example, the amino acids NPF (asparagine-proline-phenylalanine, SEQ ID NO:11) of target proteins. EH binding domains are implicated in clathrin mediated endocytosis (Chen et al., 1998; McPherson et al., 1998). It is known that a fusion protein: glutathione-S-transferase (GST)—EH domain interacts in vitro with several proteins including epsin and P-2 clathrin adaptor protein that contain NPF motifs. Phage displayed nonapeptide library with 13 different EH domains derived from yeast and mammal genes identified different NPF motifs (Paoluzi et al., 1998).

According to a preferred embodiment of the present invention the polypeptide encoded by the polynucleotide according to this aspect of the present invention participates in endocytosis processes.

As used herein in the specification and in the claims section that follows, the phrase "participates in endocytosis processes" includes an ability to bind to proteins known to participate in clathrin coated pit mediated endocytosis.

The polynucleotide according to this aspect of the present invention preferably encodes a polypeptide which is at least 75%, at least 80%, at least 85 %, at least 90%, at least 95% or more, say 95%–100% homologous to SEQ ID NOs:4, 5, 9 or 10 as determined using the BestFit software of the Wisconsin sequence analysis package, utilizing the Smith and Waterman algorithm, where gap creation penalty equals 8 and gap extension penalty equals 2.

According to preferred embodiments, the polynucleotide according to this aspect of the present invention encodes a polypeptide as set forth in SEQ ID NOs:4, 5, 9 or 10 or a portion thereof, preferably a portion which retains EHD1 or 2 activity, e.g., participates in endocytosis processes.

Alternatively or additionally, the polynucleotide according to this aspect of the present invention is preferably hybridizable with SEQ ID NOs: 1, 2, 3, 6, 7 or 8.

Hybridization for long nucleic acids (e.g., above 200 bp in length) is effected according to preferred embodiments of the present invention by stringent or moderate hybridization, wherein stringent hybridization is effected by a hybridization solution containing 10% dextrane sulfate, 1 M NaCl, 1% SDS and $5 \times 10^6$ cpm $^{32}$p labeled probe, at 65° C., with a final wash solution of 0.2×SSC and 0.1% SDS and final wash at 65° C.; whereas moderate hybridization is effected by a hybridization solution containing 10% dextrane sulfate, 1 M NaCl, 1% SDS and $5 \times 10^6$ cpm $^{32}$p labeled probe, at 65° C., with a final wash solution of 1×SSC and 0.1% SDS and final wash at 50° C.

Yet alternatively or additionally, the polynucleotide according to this aspect of the present invention is preferably at least 70%, at least 75%, at least 80%, at least 85%, at least 90%, at least 95% or more, say 95%–100%, identical with SEQ ID NOs: 1, 2, 3, 6, 7 or 8 as determined using the BestFit software of the Wisconsin sequence analysis package, utilizing the Smith and Waterman algorithm, where gap weight equals 50, length weight equals 3, average match equals 10 and average mismatch equals −9.

According to preferred embodiments the polynucleotide according to this aspect of the present invention is as set forth in SEQ ID NOs:1, 2, 3, 6, 7 or 8 or a portion thereof, said portion preferably encodes a polypeptide retaining EHD1 or 2 activity, e.g., participates in endocytosis processes.

Thus, this aspect of the present invention encompasses (i) polynucleotides as set forth in SEQ ID NOs:1, 2, 3, 6, 7 or 8; (ii) fragments thereof; (iii) sequences hybridizable therewith; (iv) sequences homologous thereto; (v) sequences encoding similar polypeptides with different codon usage; (vi) altered sequences characterized by mutations, such as deletion, insertion or substitution of one or more nucleotides, either naturally occurring or man induced, either randomly or in a targeted fashion.

According to another aspect of the present invention there is provided a nucleic acid construct comprising the isolated nucleic acid described herein.

According to a preferred embodiment the nucleic acid construct according to this aspect of the present invention further comprising a promoter for regulating the expression of the isolated nucleic acid in a sense or antisense orientation. Such promoters are known to be cis-acting sequence elements required for transcription as they serve to bind DNA dependent RNA polymerase which transcribes sequences present downstream thereof. Such down stream sequences can be in either one of two possible orientations to result in the transcription of sense RNA which is translatable by the ribozyme machinery or antisense RNA which typically does not contain translatable sequences, yet can duplex or triplex with endogenous sequences, either mRNA or chromosomal DNA and hamper gene expression, all as further detailed hereinunder.

While the isolated nucleic acid described herein is an essential element of the invention, it is modular and can be used in different contexts. The promoter of choice that is used in conjunction with this invention is of secondary importance, and will comprise any suitable promoter. It will be appreciated by one skilled in the art, however, that it is necessary to make sure that the transcription start site(s) will be located upstream of an open reading frame. In a preferred embodiment of the present invention, the promoter that is selected comprises an element that is active in the particular host cells of interest. These elements may be selected from transcriptional regulators that activate the transcription of genes essential for the survival of these cells in conditions of stress or starvation, including the heat shock proteins.

A construct according to the present invention preferably further includes an appropriate selectable marker. In a more preferred embodiment according to the present invention the construct further includes an origin of replication. In another most preferred embodiment according to the present invention the construct is a shuttle vector, which can propagate both in *E. coli* (wherein the construct comprises an appropriate selectable marker and origin of replication) and be compatible for propagation in cells, or integration in the genome, of an organism of choice. The construct according to this aspect of the present invention can be, for example, a plasmid, a bacmid, a phagemid, a cosmid, a phage, a virus or an artificial chromosome.

Alternatively, the nucleic acid construct according to this aspect of the present invention further includes a positive and a negative selection markers and may therefore be employed for selecting for homologous recombination events, including, but not limited to, homologous recombination employed in knock-in and knock-out procedures. One ordinarily skilled in the art can readily design a knock-out or knock-in constructs including both positive and negative selection genes for efficiently selecting transfected embryonic stem cells that underwent a homologous recombination event with the construct. Such cells can be introduced into developing embryos to generate chimeras, the offspring thereof can be tested for carrying the knock-out or knock-in constructs. Knock-out and/or knock-in constructs according to the present invention can be used to further investigate the functionality of EHD1 and 2. Such constructs can also be used in somatic and/or germ cells gene therapy to destroy activity of a defective, gain of function, e.g., dominant, EHD allele or to replace the lack of activity of a silent EHD allele in an organism, thereby to down or upregulate EHD activity, as required. Further detail relating to the construction and use of knock-out and knock-in constructs is provided in the Examples section that follows. Additional detail can be found in Fuktshige, S. and Ikeda, J. E.: Trapping of mammalian promoters by Cre-lox site-specific recombination. DNA Res 3 (1996) 73–80; Bedell, M. A., Jenkins, N. A. and Copeland, N. G.: Mouse models of human disease. Part I: Techniques and resources for genetic analysis in mice. Genes and Development 11 (1997) 1–11; Bermingham, J. J., Scherer, S. S., O'Connell, S., Arroyo, E., Kalla, K. A., Powell, F. L. and Rosenfeld, M. G.: Tst-1/Oct-6/SCIP regulates a unique step in peripheral myelination and is required for normal respiration. Genes Dev 10 (1996) 1751–62, which are incorporated herein by reference.

According to yet another aspect of the present invention there is provided a host cell or animal comprising a nucleic acid construct as described herein.

According to still another aspect of the present invention there is provided an oligonucleotide of at least 17, at least 18, at least 19, at least 20, at least 22, at least 25, at least 30 or at least 40, bases specifically hybridizable with the isolated nucleic acid described herein.

Hybridization of shorter nucleic acids (below 200 bp in length, e.g. 17–40 bp in length) is effected by stringent, moderate or mild hybridization, wherein stringent hybridization is effected by a hybridization solution of 6×SSC and 1% SDS or 3 M TMACl, 0.01 M sodium phosphate (pH 6.8), 1 mM EDTA (pH 7.6), 0.5% SDS, 100 $\mu$g/ml denatured salmon sperm DNA and 0.1% nonfat dried milk, hybridization temperature of 1–1.5° C. below the $T_m$, final wash solution of 3 M TMACl, 0.01 M sodium phosphate (pH 6.8), 1 mM EDTA (pH 7.6), 0.5 % SDS at 1–1.5° C. below the $T_m$; moderate hybridization is effected by a hybridization solution of 6×SSC and 0.1% SDS or 3 M TMACl, 0.01 M sodium phosphate (pH 6.8), 1 mM EDTA (pH 7.6), 0.5% SDS, 100 $\mu$g/ml denatured salmon sperm DNA and 0.1% nonfat dried milk, hybridization temperature of 2–2.5° C. below the $T_m$, final wash solution of 3 M TMACl, 0.01 M sodium phosphate (pH 6.8), 1 mM EDTA (pH 7.6), 0.5% SDS at 1–1.5° C. below the $T_m$, final wash solution of 6×SSC, and final wash at 22° C.; whereas mild hybridization is effected by a hybridization solution of 6×SSC and 1% SDS or 3 M TMACl, 0.01 M sodium phosphate (pH 6.8), 1 mM EDTA (pH 7.6), 0.5% SDS, 100 $\mu$g/ml denatured salmon sperm DNA and 0.1% nonfat dried milk, hybridization temperature of 37° C., final wash solution of. 6×SSC and final wash at 22° C.

According to an additional aspect of the present invention there is provided a pair of oligonucleotides each independently of at least 17, at least 18, at least 19, at least 20, at least 22, at least 25, at least 30 or at least 40 bases specifically hybridizable with the isolated nucleic acid described herein in an opposite orientation so as to direct exponential amplification of a portion thereof in a nucleic acid amplification reaction, such as a polymerase chain reaction. The polymerase chain reaction and other nucleic acid amplification reactions are well known in the art and require no further description herein. The pair of oligonucleotides according to this aspect of the present invention are preferably selected to have compatible melting temperatures (Tm), e.g., melting temperatures which differ by less than that 7° C., preferably less than 5° C., more preferably less than 4° C., most preferably less than 3° C., ideally between 3° C. and zero ° C. Consequently, according to yet an additional aspect of the present invention there is provided a nucleic acid amplification product obtained using the pair of primers described herein. Such a nucleic acid amplification product can be isolated by gel electrophoresis or any other size based separation technique. Alternatively, such a nucleic acid amplification product can be isolated by affinity separation, either stranded affinity or sequence affinity. In addition, once isolated, such a product can be further genetically manipulated by restriction, ligation and the like, to serve any one of a plurality of applications associated with up and/or down regulation of EHD activity as further detailed hereinunder.

According to still an additional aspect of the present invention there is provided an antisense oligonucleotide comprising a polynucleotide or a polynucleotide analog of at least 10 bases, preferably between 10 and 15, more preferably between 50 and 20 bases, most preferably, at least 17, at least 18, at least 19, at least 20, at least 22, at least 25, at least 30 or at least 40 bases being hybridizable in vivo, under physiological conditions, with a portion of a polynucleotide strand encoding a polypeptide at least 75% homologous to SEQ ID NOs:4, 5, 9 or 10 as determined using the BestFit software of the Wisconsin sequence analysis package, utilizing the Smith and Waterman algorithm, where gap creation penalty equals 8 and gap extension penalty equals 2. Such antisense oligonucleotides can be used to downregulate EHD expression as further detailed hereinunder. Such an antisense oligonucleotide is readily synthesizable using solid phase oligonucleotide synthesis.

The ability of chemically synthesizing oligonucleotides and analogs thereof having a selected predetermined sequence offers means for downmodulating gene expression. Three types of gene expression modulation strategies may be considered.

At the transcription level, antisense or sense oligonucleotides or analogs that bind to the genomic DNA by strand displacement or the formation of a triple helix, may prevent transcription. At the transcript level, antisense oligoucleotides or analogs that bind target mRNA molecules lead to the enzymatic cleavage of the hybrid by intracellular RNase H. In this case, by hybridizing to the targeted mRNA, the oligonucleotides or oligonucleotide analogs provide a duplex hybrid recognized and destroyed by the RNase H enzyme. Alternatively, such hybrid formation may lead to interference with correct splicing. As a result, in both cases, the number of the target mRNA intact transcripts ready for translation is reduced or eliminated. At the translation level, antisense oligonucleotides or analogs that bind target mRNA molecules prevent, by steric hindrance, binding of essential translation factors (ribosomes), to the target MRNA, a phenomenon known in the art as hybridization arrest, disabling the translation of such mRNAs.

Thus, antisense sequences, which as described hereinabove may arrest the expression of any endogenous and/or exogenous gene depending on their specific sequence, attracted much attention by scientists and pharmacologists who were devoted at developing the antisense approach into a new pharmacological tool.

For example, several antisense oligonucleotides have been shown to arrest hematopoietic cell proliferation (Szczylik et al., 1991), growth (Calabretta et al., 1991), entry into the S phase of the cell cycle (Heikhila et al., 1987), reduced survival (Reed et al., 1990) and prevent receptor mediated responses (Burch and Mahan, 1991).

For efficient in vivo inhibition of gene expression using antisense oligonucleotides or analogs, the oligonucleotides or analogs must fulfill the following requirements (i) sufficient specificity in binding to the target sequence; (ii) solubility in water; (iii) stability against intra- and extracellular nucleases; (iv) capability of penetration through the cell membrane; and (v) when used to treat an organism, low toxicity.

Unmodified oligonucleotides are typically impractical for use as antisense sequences since they have short in vivo half-lives, during which they are degraded rapidly by nucleases. Furthermore, they are difficult to prepare in more than milligram quantities. In addition, such oligonucleotides are poor cell membrane penetraters.

Thus it is apparent that in order to meet all the above listed requirements, oligonucleotide analogs need to be devised in a suitable manner. Therefore, an extensive search for modified oligonucleotides has been initiated.

For example, problems arising in connection with double-stranded DNA (dsDNA) recognition through triple helix formation have been diminished by a clever "switch back" chemical linking, whereby a sequence of polypurine on one strand is recognized, and by "switching back", a homopurine sequence on the other strand can be recognized. Also, good helix formation has been obtained by using artificial bases, thereby improving binding conditions with regard to ionic strength and pH.

In addition, in order to improve half-life as well as membrane penetration, a large number of variations in polynucleotide backbones have been done, nevertheless with little success.

Oligonucleotides can be modified either in the base, the sugar or the phosphate moiety. These modifications include, for example, the use of methylphosphonates, monothiophosphates, dithiophosphates, phosphoramidates, phosphate esters, bridged phosphorothioates, bridged phosphoramidates, bridged methylenephosphonates, dephospho internucleotide analogs with siloxane bridges, carbonate bridges, carboxymethyl ester bridges, carbonate bridges, carboxymethyl ester bridges, acetamide bridges, carbamate bridges, thioether bridges, sulfoxy bridges, sulfono bridges, various "plastic" DNAs,α-anomeric bridges and borane derivatives. For further details the reader is referred to Cook (1991).

International patent application WO 89/12060 discloses various building blocks for synthesizing oligonucleotide analogs, as well as oligonucleotide analogs formed by joining such building blocks in a defined sequence. The building blocks may be either "rigid" (i.e., containing a ring structure) or "flexible" (i.e., lacking a ring structure). In both cases, the building blocks contain a hydroxy group and a mercapto group, through which the building blocks are said to join to form oligonucleotide analogs. The linking moiety in the oligonucleotide analogs is selected from the group consisting of sulfide (—S—), sulfoxide (—SO—), and sulfone (—SO$_2$—).

International patent application WO 92/20702 describe an acyclic oligonucleotide which includes a peptide backbone on which any selected chemical nucleobases or analogs are stringed and serve as coding characters as they do in natural DNA or RNA. These new compounds, known as peptide nucleic acids (PNAs), are not only more stable in cells than their natural counterparts, but also bind natural DNA and RNA 50 to 100 times more tightly than the natural nucleic acids cling to each other. PNA oligomers can be synthesized from the four protected monomers containing thymine, cytosine, adenine and guanine by Merrifield solid-phase peptide synthesis. In order to increase solubility in water and to prevent aggregation, a lysine amide group is placed at the C-terminal region.

Thus, antisense technology requires pairing of messenger RNA with an oligonucleotide to form a double helix that inhibits translation. The concept of antisense-mediated gene therapy was already introduced in 1978 for cancer therapy. This approach was based on certain genes that are crucial in cell division and growth of cancer cells. Synthetic fragments of genetic substance DNA can achieve this goal. Such molecules bind to the targeted gene molecules in RNA of tumor cells, thereby inhibiting the translation of the genes and resulting in dysfunctional growth of these cells. Other mechanisms has also been proposed. These strategies have been used, with some success in treatment of cancers, as well as other illnesses, including viral and other infectious diseases.

Antisense oligonucleotides are typically synthesized in lengths of 13–30 nucleotides. The life span of oligonucleotide molecules in blood is rather short. Thus, they have to be chemically modified to prevent destruction by ubiquitous nucleases present in the body. Phosphorothioates are very widely used modification in antisense oligonucleotide ongoing clinical trials. A new generation of antisense molecules consist of hybrid antisense oligonucleotide with a central portion of synthetic DNA while four bases on each end have been modified with 2'O-methyl ribose to resemble RNA. In preclinical studies in laboratory animals, such compounds have demonstrated greater stability to metabolism in body tissues and an improved safety profile when compared with the first-generation unmodified phosphorothioate (Hybridon Inc. news). Dosens of other nucleotide analogs have also been tested in antisense technology.

RNA oligonucleotides may also be used for antisense inhibition as they form a stable RNA—RNA duplex with the target, suggesting efficient inhibition. However, due to their low stability RNA oligonucleotides are typically expressed inside the cells using vectors designed for this purpose. This approach is favored when attempting to target a MRNA that encodes an abundant and long-lived protein.

Recent scientific publications have validated the efficacy of antisense compounds in animal models of hepatitis, cancers, coronary artery restenosis and other diseases. The first antisense drug was recently approved by the FDA. This drug Fomivirsen, developed by Isis, is indicated for local treatment of cytomegalovirus in patients with AIDS who are intolerant of or have a contraindication to other treatments for CMV retinitis or who were insufficiently responsive to previous treatments for CMV retinitis (Pharmacotherapy News Network).

Several antisense compounds are now in clinical trials in the United States. These include locally administered antivirals, systemic cancer therapeutics. Antisense therapeutics has the potential to treat many life-threatening diseases with a number of advantages over traditional drugs. Traditional drugs intervene after a disease-causing protein is formed. Antisense therapeutics, however, block mRNA transcription/translation and intervene before a protein is formed, and since antisense therapeutics target only one specific mRNA, they should be more effective with fewer side effects than current protein-inhibiting therapy.

A second option for disrupting gene expression at the level of transcription uses synthetic oligonucleotides capable of hybridizing with double stranded DNA. A triple helix is formed. Such oligonucleotides may prevent binding of transcription factors to the gene's promoter and therefore inhibit transcription. Alternatively, they may prevent duplex unwinding and, therefore, transcription of genes within the triple helical structure.

Thus, according to a further aspect of the present invention there is provided a pharmaceutical composition comprising the antisense oligonucleotide described herein and a pharmaceutically acceptable carrier. The pharmaceutically acceptable carrier can be, for example, a liposome loaded with the antisense oligonucleotide. Formulations for topical administration may include, but are not limited to, lotions, ointments, gels, creams, suppositories, drops, liquids, sprays and powders. Conventional pharmaceutical carriers, aqueous, powder or oily bases, thickeners and the like may be necessary or desirable. Compositions for oral administration include powders or granules, suspensions or solutions in water or non-aqueous media, sachets, capsules or tablets. Thickeners, diluents, flavorings, dispersing aids, emulsifiers or binders may be desirable. Formulations for parenteral administration may include, but are not limited to, sterile aqueous solutions which may also contain buffers, diluents and other suitable additives.

According to still a further aspect of the present invention there is provided a ribozyme comprising the antisense oligonucleotide described herein and a ribozyme sequence fused thereto. Such a ribozyme is readily synthesizable using solid phase oligonucleotide synthesis.

Ribozymes are being increasingly used for the sequence-specific inhibition of gene expression by the cleavage of mRNAs encoding proteins of interest. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders. Most notably, several ribozyme gene therapy protocols for HIV patients are already in Phase 1 trials (Welch et al., 1998). More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

According to yet a further aspect of the present invention there is provided a recombinant protein comprising a polypeptide having an N-terminal region containing a nucleotide binding consensus site, a central coiled-coil structure and a C-terminal region including an eps15 homology (EH) domain, the polypeptide participates in endocytosis.

Preferably, the polypeptide according to this aspect of the present invention is at least 75%, at least 80%, at least 85%, at least 90%, at least 95% or more, say 95%–100%, identical or homologous (identical+similar) to SEQ ID NOs:4, 5, 9 or 10 as determined using the BestFit software of the Wisconsin sequence analysis package, utilizing the Smith and Waterman algorithm, where gap creation penalty equals 8 and gap extension penalty equals 2.

Most preferably the polypeptide includes at least a portion of SEQ ID NOs:4, 5, 9 or 10.

Additionally or alternatively, the polypeptide according to this aspect of the present invention is preferably encoded by a polynucleotide hybridizable with SEQ ID NOs: 1, 2, 3, 6, 7 or 8 or a portion thereof under any of the stringent or moderate hybridization conditions described above for long nucleic acids. Still additionally or alternatively, the polypeptide according to this aspect of the present invention is preferably encoded by a polynucleotide at least 70%, at least 75%, at least 80%, at least 85%, at least 90%, at least 95% or more, say 95%–100%, identical with SEQ ID NOs: 1, 2, 3, 6, 7 or 8 or portions thereof as determined using the BestFit software of the Wisconsin sequence analysis package, utilizing the Smith and Waterman algorithm, where gap weight equals 50, length weight equals 3, average match equals 10 and average mismatch equals −9.

Thus, this aspect of the present invention encompasses (i) polypeptides as set forth in SEQ ID NOs:4, 5, 9 or 10; (ii) fragments thereof; (iii) polypeptides homologous thereto; and (iv) altered polypeptides characterized by mutations, such as deletion, insertion or substitution of one or more amino acids, either naturally occurring or man induced, either randomly or in a targeted fashion.

According to still a further aspect of the present invention there is provided a pharmaceutical composition comprising, as an active ingredient, the recombinant protein described herein and a pharmaceutical acceptable carrier which is further described above.

According to another aspect of the present invention there is provided a peptide or a peptide analog comprising a stretch of at least 6, at least 7, at least 8, at least 9, at least 10, 10–15, 12–17, or 15–20 consecutive amino acids or analogs thereof derived from a polypeptide at least 75%, at least 80%, at least 85%, at least 90%, at least 95% or more, say 95%–100% identical or homologous (identical+similar) to SEQ ID NOs:4, 5, 9 or 10 as determined using the BestFit software of the Wisconsin sequence analysis package, utilizing the Smith and Waterman algorithm, where gap creation penalty equals 8 and gap extension penalty equals 2. Preferably, the peptide or a peptide analog according to this aspect of the present invention comprises a stretch of at least 6, at least 7, at least 8, at least 9, at least 10, 10–15, 12–17, or 15–20 consecutive amino acids or analogs thereof derived from SEQ ID NOs:4, 5, 9 or 10.

As used herein in the specification and in the claims section below the phrase "derived from a polypeptide" refers to peptides derived from the specified protein or proteins and further to homologous peptides derived from equivalent regions of proteins homologous to the specified proteins of the same or other species. The term further relates to permissible amino acid alterations and peptidomimetics designed based on the amino acid sequence of the specified proteins or their homologous proteins.

As used herein in the specification and in the claims section below the term "amino acid" is understood to include the 20 naturally occurring amino acids; those amino acids often modified post-translationally in vivo, including for example hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids. Further elaboration of the possible amino acids usable according to the present invention and examples of non-natural amino acids useful in MHC-1 recognizable peptide antigens are given hereinunder.

Hydrophilic aliphatic natural amino acids can be substituted by synthetic amino acids, preferably Nleu, Nval and/or α-aminobutyric acid or by aliphatic amino acids of the general formula —HN(CH$_2$)$_n$COOH, wherein n=3–5, as well as by branched derivatives thereof, such as, but not limited to:

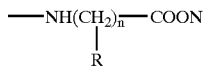

wherein R is, for example, methyl, ethyl or propyl, located at any one or more of the n carbons.

Each one, or more, of the amino acids can include a D-isomer thereof. Positively charged aliphatic carboxylic acids, such as, but not limited to, H$_2$N(CH$_2$)$_n$ COOH, wherein n=2–4 and H$_2$N—C(NH)—NH(CH$_2$)$_n$COOH, wherein n=2–3, as well as by hydroxy Lysine, N-methyl Lysine or ornithine (Orn) can also be employed. Additionally, enlarged aromatic residues, such as, but not limited to, H$_2$N—(C$_6$H$_6$)—CH$_2$—COOH, p-aminophenyl alanine, H$_2$N—F(NH)—NH—(C$_6$H$_6$)—CH$_2$—COOH, p-guanidinophenyl alanine or pyridinoalanine (Pal) can also be employed. Side chains of amino acid derivatives (if these are Ser, Tyr, Lys, Cys or Orn) can be protected-attached to alkyl, aryl, alkyloyl or aryloyl moieties. Cyclic derivatives of amino acids can also be used. Cyclization can be obtained through amide bond formation, e.g., by incorporating Glu, Asp, Lys, Orn, di-amino butyric (Dab) acid, di-aminopropionic (Dap) acid at various positions in the chain (—CO—NH or —NH—CO bonds). Backbone to backbone cyclization can also be obtained through incorporation of modified amino acids of the formulas H—N((CH$_2$)$_n$—COOH)—C(R)H—COOH or H—N((CH$_2$)$_n$—COOH)—C(R)H—NH$_2$, wherein n=1–4, and further wherein R is any natural or non-natural side chain of an amino acid. Cyclization via formation of S—S bonds through incorporation of two Cys residues is also possible. Additional side-chain to side chain cyclization can be obtained via formation of an interaction bond of the formula —(—CH$_2$—)$_n$—S—CH$_2$—C—, wherein n=1 or 2, which is possible, for example, through incorporation of Cys or homocys and reaction of its free SH group with, e.g., bromoacetylated Lys, Orn, Dab or Dap. Peptide bonds (—CO—NH—) within the peptide may be substituted by N-methylated bonds (—N(CH$_3$)—CO—), ester bonds (—C(R)H—C—O—O—C(R)—N—), ketomethylen bonds (—CO—CH$_2$—), α-aza bonds —NH—N(R)—CO—), wherein R is any alkyl, e.g., methyl, carba bonds (—CH$_2$—NH—), hydroxyethylene bonds (—CH(OH)—CH$_2$—), thioamide bonds (—CS—NH—), olefinic double bonds (—CH=CH—), retro amide bonds (—NH—CO—), peptide derivatives (—N(R)—CH$_2$—CO—), wherein R is the "normal" side chain, naturally presented on the carbon atom. These modifications can occur at any of the bonds along the peptide chain and even at several (2–3) at the same time. Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

According to still another aspect of the present invention there is provided a display library comprising a plurality of display vehicles (such as phages, viruses or bacteria) each displaying at least 6, at least 7, at least 8, at least 9, at least 10, 10–15, 12–17, or 15–20 consecutive amino acids derived from a polypeptide at least 75%, at least 80%, at least 85%, at least 90%, at least 95% or more, say 95%–100% identical or homologous (identical+similar) to SEQ ID NOs:4, 5, 9 or 10 as determined using the BestFit software of the Wisconsin sequence analysis package, utilizing the Smith and Waterman algorithm, where gap creation penalty equals 8 and gap extension penalty equals 2. According to a preferred embodiment of this aspect of the present invention substantially every 6, 7, 8, 9, 10, 10–15, 12–17 or 15–20 consecutive amino acids derived from the polypeptide which is at least 75%, at least 80%, at least 85%, at least 90%, at least 95% or more, say 95%–100% identical or homologous (identical+similar) to SEQ ID NOs:4, 5, 9 or 10 are displayed by at least one of the plurality of display vehicles, so as to provide a highly representative library. Preferably, the consecutive amino acids or amino acid analogs of the peptide or peptide analog according to this aspect of the present invention are derived from SEQ ID NOs:4, 5, 9 or 10. Methods of constructing display libraries are well known in the art. such methods are described, for example, in Young AC, et al., "The three-dimensional structures of a polysaccharide binding antibody to Cryptococcus neoformans and its complex with a peptide from a phage display library: implications for the identification of peptide mimotopes" J Mol Biol 1997 Dec. 12;274(4):622–34; Giebel L B et al. "Screening of cyclic peptide phage libraries identifies ligands that bind streptavidin with high affinities" Biochemistry 1995 Nov. 28;34(47):15430–5; Davies EL et al., "Selection of specific phage-display antibodies using libraries derived from chicken immunoglobulin genes" J Immunol Methods 1995 Oct. 12;186(l):125–35; Jones C rt al. "Current trends in molecular recognition and bioseparation" J Chromatogr A 1995 Jul. 14;707(1):3–22; Deng S J et al. "Basis for selection of improved carbohydrate-binding single-chain antibodies from synthetic gene libraries" Proc Natl Acad Sci U S A 1995 May 23;92(11):4992–6; and Deng S J et al. "Selection of antibody single-chain variable fragments with improved carbohydrate binding by phage display" J Biol Chem 1994 Apr. 1;269(13):9533–8, which are incorporated herein by reference. Display libraries according to this aspect of the present invention can be used to identify and isolate polypeptides which are capable of regulating EHD activity.

According to still another aspect of the present invention there is provided an antibody comprising an immunoglobulin specifically recognizing and binding a polypeptide at least 75%, at least 80%, at least 85%, at least 90%, at least 95 % or more, say 95%–100% identical or homologous (identical+similar) to SEQ ID NOs:4, 5, 9 or 10 as determined using the BestFit software of the Wisconsin sequence analysis package, utilizing the Smith and Waterman algorithm, where gap creation penalty equals 8 and gap extension penalty equals 2. According to a preferred embodiment of this aspect of the present invention the antibody specifically recognizing and binding the polypeptides set forth in SEQ ID NOs:4, 5, 9 or 10.

The present invention can utilize serum immunoglobulins, polyclonal antibodies or fragments thereof, (i.e., immunoreactive derivative of an antibody), or monoclonal antibodies or fragments thereof. Monoclonal antibodies or purified fragments of the monoclonal antibodies having at least a portion of an antigen binding region, including such as Fv, F(abl)2, Fab fragments (Harlow and Lane, 1988 Antibody, Cold Spring Harbor), single chain antibodies (U.S. Patent 4,946,778), chimeric or humanized antibodies and complementarily determining regions (CDR) may be prepared by conventional procedures. Purification of these serum immunoglobulins antibodies or fragments can be accomplished by a variety of methods known to those of skill including, precipitation by ammonium sulfate or sodium sulfate followed by dialysis against saline, ion exchange chromatography, affinity or immunoaffinity chromatography as well as gel filtration, zone electrophoresis, etc. (see Goding in, Monoclonal Antibodies: Principles and Practice, 2nd ed., pp. 104–126, 1986, Orlando, Fla., Academic Press). Under normal physiological conditions antibodies are found in plasma and other body fluids and in the membrane of certain cells and are produced by lymphocytes of the type denoted B cells or their functional equivalent. Antibodies of the IgG class are made up of four polypeptide chains linked together by disulfide bonds. The four chains of intact IgG molecules are two identical heavy chains referred to as H-chains and two identical light chains referred to as L-chains. Additional classes includes IgD, IgE, IgA, IgM and related proteins.

Methods for the generation and selection of monoclonal antibodies are well known in the art, as summarized for example in reviews such as Tramontano and Schloeder, Methods in Enzymology 178, 551–568, 1989. A recombinant EHD of the present invention may be used to generate antibodies in vitro. More preferably, the recombinant EHD of the present invention is used to elicit antibodies in vivo. In general, a suitable host animal is immunized with the recombinant EHD of the present invention. Advantageously, the animal host used is a mouse of an inbred strain. Animals are typically immunized with a mixture comprising a solution of the recombinant EHD of the present invention in a physiologically acceptable vehicle, and any suitable adjuvant, which achieves an enhanced immune response to the immunogen. By way of example, the primary immunization conveniently may be accomplished with a mixture of a solution of the recombinant EHD of the present invention and Freund's complete adjuvant, said mixture being prepared in the form of a water in oil emulsion. Typically the immunization may be administered to the animals intramuscularly, intradermally, subcutaneously, intraperitoneally, into the footpads, or by any appropriate route of administration. The immunization schedule of the immunogen may be adapted as required, but customarily involves several subsequent or secondary immunizations using a milder adjuvant such as Freund's incomplete adjuvant. Antibody titers and specificity of binding to the EHD can be determined during the immunization schedule by any convenient method including by way of example radioimmunoassay, or enzyme linked immunosorbant assay, which is known as the ELISA assay. When suitable antibody titers are achieved, antibody producing lymphocytes from the immunized animals are obtained, and these are cultured, selected and cloned, as is known in the art. Typically, lymphocytes may be obtained in large numbers from the spleens of immunized animals, but they may also be retrieved from the circulation, the lymph nodes or other lymphoid organs. Lymphocytes are then fused with any suitable myeloma cell line, to yield hybridomas, as is well known in the art. Alternatively, lymphocytes may also be stimulated to grow in culture, and may be immortalized by methods known in the art including the exposure of these lymphocytes to a virus, a chemical or a nucleic acid such as an oncogene, according to established protocols. After fusion, the hybridomas are cultured under suitable culture conditions, for example in multiwell plates, and the culture supernatants are screened to identify cultures containing antibodies that recognize the hapten of choice. Hybridomas that secrete antibodies that recognize the recombinant EHD of the present invention are cloned by limiting dilution and expanded, under appropriate culture conditions. Monoclonal antibodies are purified and characterized in terms of immunoglobulin type and binding affinity.

The predicted protein structure of EHD1, its expression pattern and its subcellular localization, point to the possibility that EHD1 is an IGF1 receptor substrate that participates in regulated endocytosis, following modification by the ligand bound receptor.

EHD1 and 2 are novel gene members of the EH containing protein family. Experiments indicated that these proteins participate in clathrin coated pit mediated endocytosis of IGF1 receptor, following its binding to its ligand. The central role IGFs and IGF1 receptor play in different biological processes, as further detailed hereinabove, make IGF signaling pathways important targets for drug development aiming at interfering with their normal and/or abnormal expression and function. The following embodiments of the present invention are therefore directed at intervention with EHD activity and therefore with IGF1 receptor signaling.

Thus, according to yet another aspect of the present invention there is provided a pharmaceutical composition comprising, as an active ingredient, an agent for regulating an endogenous protein activity in vivo, the endogenous protein being at least 75%, at least 80%, at least 85%, at least 90%, at least 95 % or more, say 95%–100% identical or homologous (identical+similar) to SEQ ID NOs:4, 5, 9 or 10 as determined using the BestFit software of the Wisconsin sequence analysis package, utilizing the Smith and Waterman algorithm, where gap creation penalty equals 8 and gap extension penalty equals 2.

According to yet another aspect of the present invention there is provided a method of regulating an endogenous protein activity in vivo. The method according to this aspect of the present invention is effected by administering an agent for regulating the endogenous protein activity in vivo, the endogenous protein being at least 75%, at least 80%, at least 85%, at least 90%, at least 95 % or more, say 95%–100% identical or homologous (identical+similar) to SEQ ID NOs:4, 5, 9 or 10 as determined using the BestFit software of the Wisconsin sequence analysis package, utilizing the Smith and Waterman s algorithm, where gap creation penalty equals 8 and gap extension penalty equals 2.

As further explained above, an agent used in the pharmaceutical composition or method herein described can indirectly serve to regulate IGF1 receptor cell signaling via altered clathrin coated pit mediated endocytosis. Such an agent can be used for upregulating, or alternatively downregulating the activity of the endogenous protein and as a result to indirectly downregulate or alternatively upregulate IGF1 receptor cell signaling via altered clathrin coated pit mediated endocytosis.

An agent which can be used according to the present invention to upregulate the activity of the endogenous protein and as a result to downregulate IGF1 receptor cell signaling via altered clathrin coated pit mediated endocytosis can include, for example, an expressible sense polynucleotide at least 70%, at least 75%, at least 80%, at least 85%, at least 90%, at least 95% or more, say 95%–100%, identical with SEQ ID NOs: 1, 2, 3, 6, 7 or 8 as determined using the BestFit software of the Wisconsin sequence analysis package, utilizing the Smith and Waterman algorithm, where gap weight equals 50, length weight equals 3, average match equals 10 and average mismatch equals −9.

Alternatively, an agent which can be used according to the present invention to upregulate the activity of the endogenous protein and as a result to downregulate IGF1 receptor cell signaling via altered clathrin coated pit mediated endocytosis can include, for example, at least 75%, at least 80%, at least 85%, at least 90%, at least 95% or more, say 95%–100% identical or homologous (identical+similar) to SEQ ID NOs:4, 5, 9 or 10 as determined using the BestFit software of the Wisconsin sequence analysis package, utilizing the Smith and Waterman algorithm, where gap creation penalty equals 8 and gap extension penalty equals 2.

An agent which can be used according to the present invention to downregulate the activity of the endogenous protein and as a result to upregulate IGF1 receptor cell signaling via altered clathrin coated pit mediated endocytosis can include, for example, an expressible antisense polynucleotide at least 70%, at least 75%, at least 80%, at least 85%, at least 90%, at least 95% or more, say 95%–100%, identical with SEQ ID NOs:1, 2, 3, 6, 7 or 8 as determined using the BestFit software of the Wisconsin sequence analysis package, utilizing the Smith and Waterman algorithm, where gap weight equals 50, length weight equals 3, average match equals 10 and average mismatch equals −9.

Alternatively, an agent which can be used according to the present invention to downregulate the activity of the endogenous protein and as a result to upregulate IGF1 receptor cell signaling via altered clathrin coated pit mediated endocytosis can include, for example, an antisense oligonucleotide or ribozyme which includes a polynucleotide or a polynucleotide analog of at least 10 bases, preferably between 10 and 15, more preferably between 50 and 20 bases, most preferably, at least 17, at least 18, at least 19, at least 20, at least 22, at least 25, at least 30 or at least 40 bases which is hybridizable in vivo, under physiological conditions, with a portion of a polynucleotide strand encoding a polypeptide at least 75%, at least 80%, at least 85%, at least 90%, at least 95% or more, say 95%–100% identical or homologous (identical+similar) to SEQ ID NOs:4, 5, 9 or 10 as determined using the BestFit software of the Wisconsin sequence analysis package, utilizing the Smith and Waterman algorithm, where gap creation penalty equals 8 and gap extension penalty equals 2.

Still alternatively, an agent which can be used according to the present invention to downregulate the activity of the endogenous protein and as a result to upregulate IGF1 receptor cell signaling via altered clathrin coated pit mediated endocytosis can include, for example, a peptide or a peptide analog representing a stretch of at least 6, at least 7, at least 8, at least 9, at least 10, 10–15, 12–17, or 15–20 consecutive amino acids or analogs thereof derived from a polypeptide at least 75%, at least 80%, at least 85%, at least 90%, at least 95% or more, say 95%–100% identical or homologous (identical+similar) to SEQ ID NOs:4, 5, 9 or 10 as determined using the BestFit software of the Wisconsin sequence analysis package, utilizing the Smith and Waterman algorithm, where gap creation penalty equals 8 and gap extension penalty equals 2.

Peptides or peptide analogs containing the interacting sites of the EH, coiled-coil and the nucleotide binding domains of the new EHD genes according to the present invention will compete by protein interactions to form protein complexes with either EHD or proteins interacting with EHD, inhibiting or accelerating the pathways in which EHD is involved. Thus, peptides or peptide analogs can compete for substrate enzymatic activities, including, but not limited to, phosphorylation sites, protease sites, phosphatase sites and glycosylation sites. Peptides or peptide analogs containing the enzymatic sites will compete with the original substrates, inhibiting the protein function.

The following biochemical and molecular systems are known for the characterization and identification of protein—protein interaction and peptides as substrates, through peptide analysis, which systems can be used to identify inhibitory peptide sequences. One such system employs introduction of a genetic material encoding a functional protein or a mutated form of the protein, including amino acid deletions and substitutions, into cells. This system, can be used, as further exemplified in the Examples section that follows, to identify functional domains of the protein by the analysis of its activity and the activity of its derived mutants in the cells. Another such system employs the introduction of small encoding fragments of a gene into cells, e.g., by means of a display library or a directional randomly primed cDNA library comprising fragments of the gene, and analyzing the activity of the endogenous protein in their presence (see, for example, Gudkov et al., 1993 and Pestov et al., 1999). Yet an additional system is realized by screening expression libraries with peptide domains, as exemplified, for example, by Yamabhai et al., 1998. In yet another such system overlapping synthetic peptides derived from specific gene products are used to study and affect in vivo and in vitro protein—protein interactions. For example, synthetic overlapping peptides derived from the HIV-1 vif gene (20–30 amino acids) were assayed for different viral activities (Baraz et al., 1998) and were found to inhibit purified viral protease activity; bind to the viral protease; inhibit the Gag-Pol polyprotein cleavage; and inhibit mature virus production in human cells.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturers' specifications. These techniques and various other techniques are generally performed according to Sambrook et al., molecular Cloning—A Laboratory Manual, Cold Spring Harbor Laboratory, Cold Spring Harbor, N.Y. (1989). The manual is hereinafter referred to as "Sambrook". Other general references are provided throughout this document. The procedures therein are believed to be well known in the art and are provided for the convenience of the reader. All the information contained therein is incorporated herein by reference.

ISOLATION AND CHARACTERIZATION OF EHD1 MATERIALS AND EXPERIMENTAL METHODS

Libraries and Screening Procedures:

ICR/SWISS mouse genomic library (liver genomic DNA in EMBL3, Promega, USA) was screened with a mouse prosaposin cDNA as a probe. Positive plaques were grown and DNA was prepared according to described methods. (Maniatis et al., 1982).

A human cerebellar cDNA library in Lambda Zap II vector (Stratagene, USA) was screened with a 500 bp fragment obtained from a mouse genomic clone by cleavage with the restriction enzymes MunI and HincII (FIG. 1; see the "Results" section for details).

A mouse brain cDNA library in Lambda Zap II vector (Stratagene, USA) was screened with a 1 kb human cDNA fragment as a probe. Plasmids containing the corresponding cDNAs were excised from the phages following the manufacturer's recommendations.

A 129/SVev mouse genomic library in lambda FIXII (a gift from Dr. Alexandra Joyner, NYUMC, New York, N.Y., 10062, USA) was screened with a 800 bp EcoRI-HincII fragment and a 1100 bp HincII—HincII fragment obtained from the mouse EHD1 cDNA clone.

Sequencing was according to Sanger (Sanger, 1981), using double stranded plasmid DNA.

Southern (Zoo) Blot:

10 μg of Genomic DNA samples from different organisms, digested overnight with the restriction enzyme EcoRI, were electrophoresed through a 0.7% agarose gel and blotted onto a nylon filter. Prehybridization was for 2 hours in a buffer containing 10% dextrane sulfate, 1 M NaCl and 1% SDS at 65° C. Hybridization was in the same buffer with $5\times10^6$ cpm of EHD1 cDNA probe at 65° C. for 18 hours. Following one wash in 2×SSC, 0.1% SDS for 15 minutes at 65° C. and several washes in 0.2×SSC, 0.1% SDS at 65° C. the filter was exposed to an X-ray film.

RNA Extraction:

RNA was prepared from mouse organs using the TRIREAGENT kit (MRC, USA) according to the manufacturer's recommendations. RNA samples were electrophoresed through a 1% agarose gel containing formaldehyde and were transferred onto a nylon membrane.(Thomas, 1980). Prehybridization was for 0.5 hour in 0.5 M Na-phosphate buffer pH 7.4, 7% SDS and 1 mM EDTA at 65° C. Hybridization was in the same buffer with $1\times10^7$ cpm of the appropriate probe at 65° C. for 18 hours. After one wash in 2×SSC, 0.1% SDS for 15 minutes at 65° C. and several washes in 0.2×SSC, 0.1% SDS at 65° C. the filter was exposed to an X-ray film. Phosphor-imaging analysis was performed as well.

Probe Preparation:

Probes were prepared by the random priming technique using different commercial kits according to the manufacturers'recommendations.

Coupled in vitro Transcription-Translation:

A 2 kb human EHD1 cDNA fragment containing the entire ORF, cloned in the pBluescript vector, was expressed using the Coupled Transcription/Translation Reticulocyte Lysate System according to the manufacturer's recommendations (Promega, USA). The protein product was then analyzed directly on a 10% SDS-PAGE or following immunoprecipitation with anti-human EHD1 antibodies as described.(Pasmanik-Chor et al., 1997). The gel was dried and exposed to an X-ray film.

Transfection:

A 2 kb human EHD1 cDNA fragment containing the entire ORF was cloned in pcDNA1 or pcDNA3 (Invitrogen, USA) between the EcoRI and XhoI restriction sites. DNA of the appropriate plasmid was introduced into cells using the Transfection Reagent (FuGENE 6, Boehringer-Mannheim), according to the manufacturer's recommendations.

$Ca^{2+}$ Binding to EHD1:

1 μg of recombinant EHD1 or calmodulin (a gift from Dr. Robert Flor, the Weizmann Institute of Science, Rehovot, Israel) was resolved through a 6% SDS-PAGE. The gel was electroblotted and incubated for 2 hours with 25 mg/liter ruthenium red in 50 mM Tris-HCl pH 8.0 at 22° C.

Antibody preparation:

A 2 kb human EHD1 cDNA fragment containing the entire ORF was subcloned into the pET-28b (Novagen, USA). DNA was prepared from positive clones and introduced into the E. coli strain DE3 according to the manufacturer's recommendations. After IPTG induction, extracts were electrophoresed through a 10% SDS-PAGE. Extracts were prepared from positive clones and EHD1 was purified using the QIAexpress Ni-NTA Protein Purification System according to the manufacturer's recommendations (Qiagen Inc, USA). Polyclonal antibodies against human EHD1 were prepared by immunizing rabbits with 3–4 injections of 0.5 mg of the purified protein at 1–2 weeks intervals. Animals were bled 10 days after the final booster. Serum was separated from the blood and stored at –80° C.

Immunohistochemical Staining:

Mouse organs were fixed in Bouins and embedded in paraffin. 8 micron sections were prepared and fixed on slides pretreated with 2% TESPA (Sigma, USA). Following deparaffinization (30 minutes at 80° C.) and rehydration, the slide were treated with 50 μl/slide of 1.5 mg/ml hyaluronidase in PBS pH 6.5 for 1 hour at 37° C. and then washed in PBS pH 7.4 (10 minutes). 50 ml/slide of 0.3 % $H_2O_2$ in PBS pH 7.4 were added for 10 minutes after which they were washed in PBS pH 7.4 (10 minutes). Blocking was performed by addition of 50 μl/slide of normal goat serum containing 5% trasylol (Bayer) at 37° C. for 30 minutes. Rabbit anti-EHD1 antibodies (1:50 in PBS containing 10% normal goat serum and 5% trasylol) were incubated with the slides for 18 hours at 4° C. after which they were washed 3 times in PBS pH 7.4 and immersed for 10 minutes in the same solution. HRP conjugated goat anti-rabbit antibodies (Sigma, USA, 1:40) in PBS pH 7.4 containing 5% trasylol were added for 30 minutes at room temperature, in the dark, following a wash in PBS pH 7.4 for 10 minutes.

For HRP reaction 0.4 mg/ml of the substrate (3'3' diaminbenzoidin) in PBS pH 7.4 containing 3% $H_2O_2$ was added in the dark for 10 minutes. Following 3 washes in PBS pH 7.4 and immersion for 10 minutes in PBS pH 7.4, staining of the slides was performed with 1% methylene blue in PBS pH 7.4 for 5 minutes. Following two washes in water, dehydration was performed. Mounting was with mercoglass (Merck, USA).

Protein Analyses:

Western blot analysis: Proteins were separated through a 10% SDS-PAGE and the gels were blotted onto a Protran BA85 cellulose nitrate filters (Schleicher&Schull). After blocking, the filters were reacted with rabbit anti human EHD1 antibodies for 2 hours at room temperature, in PBS containing 10 % milk powder and 0.05% TWEEN-20. Following washes, the filters were reacted with goat anti-rabbit HRP conjugated antibodies for 2 hours at room temperature. After washes, an ECL reaction was applied. Equal volumes of solution I (2.5 mM Luminol, 400 μM paracumaric acid in 100 mM Tris-HCl, pH 8.5) and solution II (5.4 mM $H_2O_2$ in 100 mM Tris-HCl, pH 8.5) were mixed and incubated 1 minute with the filters, which were then exposed to an X-ray film and developed.

Immunoprecipitation: $5 \times 10^6$ cpm were immunopercipitated with 50 μl of anti human EHD1 antibodies essentially as described elsewhere (Pasmanik-Chor et al., 1997). Immunopercipitates were resolved on a 10% SDS-PAGE, which was dried and exposed to an X-ray film.

Protein overlay assays: Protein samples were resolved through a 8% SDS-PAGE and transferred to nitrocellulose membranes (Schleicher & Schuell) in 10 mM Tris, 0.2 M glycine overnight at 10 mA. Nonspecific binding sites were blocked by incubation in 50 mM Tris-HCl pH 7.6, 150 mM NaCl containing 5% non-fat milk and 0.1% TWEEN 20 (Sigma) for 1 hour at room temperature.

The blots were thereafter incubated for two hours at room temperature in the presence of 3 mg/ml of purified EHD1 in 50 mM Tris-HCl pH 7.6, 150 mM NaCl containing 2% non-fat milk and 0.1% TWEEN (Sigma). The blots were then incubated for 1 hour with rabbit polyclonal sera raised against the human EHD 1 protein, followed by peroxidase-labeled goat anti rabbit secondary antibodies (Jackson Laboratories, USA). Labeled proteins were revealed using enhanced chemiluminescence (Amersham).

Preparation of Digoxygenin Labeled RNA Probe:

Antisense and sense riboprobes were prepared of a plasmid harboring the (5') 800 bp of the mouse EHD1 cDNA, essentially as described elsewhere (Matise and Joyner, 1997).

In situ Hybridization:

Mouse embryos were fixed in 4% paraformaldehyde in PBS (overnight, 4° C.). Following a series of dehydrations and rehydrations, the embryos were washed in PBT (PBS containing 0.1% TWEEN-20). They were then treated with 6% $H_2O_2$ in PBT and then with proteinase K, after which they were transferred to 0.2% glycine in PBT. After PBT washes, they were fixed with 4% paraformaldehyde, 0.2% glutaraldehyde. Prehybridization was in 50% formamide, 5×SSC pH 4.5, 0.05% heparin, 50 μg/ml tRNA, 1% SDS at 70° C. for 1 hour. Hybridization was in the same solution containing 0.1–0.2 μg of dig labeled probe at 70° C. for 18 hours. Washes were performed in: solution I: 50% formaldehyde, 4×SSC pH 4.5, 1% SDS; solution II: 0.5M NaCl, 10 mM Tris pH 7.5, 0.1% TWEEN-20 at 70° C.; solution III: 50% formaldehyde, 4×SSC pH 4.5, at room temperature. After RNase treatment (100 mg/ml in solution II), solution III washes were repeated at room temperature and 65° C. The embryos were then reacted with anti-dig conjugated alkaline phosphatase in the presence of the substrate BM-purple (Boehringer Mannheim Inc.) until a color was observed.(Matise and Joyner, 1997).

Endocytosis:

Cells ($1 \times 10^5$) were grown on coverslips in 24-wells for 24 hours and transfected with 2 μg of pEGFP-C3 (Clontech, USA) into which a 2 kb human EHD1 cDNA fragment containing the entire ORF was introduced, between the EcoRI and SalI restriction sites. 48 hours later medium was replaced with a serum free medium for 30 minutes at 37° C. Following three washes with HBSS (Hank's Balanced Salts, containing 20 mM Hepes pH 7.4 and 2% BSA), 50 μg/ml rhodamine conjugated transferrin in HBSS was added for 20 minutes at 37° C. Following washes with HBSS and fixation with 3% paraformaldehyde in PBS, the coverslips were glued on slides. Fluorescence of cells was observed using confocal microscope.

Cellular Localization of Deletion Mutants of EHD1:

Cells ($1 \times 10^5$) were grown on coverslips in 24-wells for 24 hours and transfected with 2 μg of different plasmids, as follows: (i) pEGFP-C3 containing a 2 kb human EHD1 cDNA fragment, including the entire ORF, as above (GFP-EHD1); (ii) a mutant lacking the N terminal domain, created by restriction digest of GFP-EHD1 with BamHI, filling with the Klenow fragment of E. coli DNA polymerase I and re-ligation; and (iii) a mutant lacking the EH domain, created by restriction digest of GFP-EHD1 with HincII, and re-ligation. 18 hours later, the cells were fixed with 3% paraformaldehyde in PBS and the coverslips were glued on slides. Fluorescence of cells was observed using confocal or fluorescent microscope.

Characterizing and Isolating the Proteins that Bind, Directly or Indirectly, to EHD1:

Rat Testes Homogenization:

Three month old Spreg-Dowley rat males were scarified. 5 grams testes were homogenized at 1:10 (W:V) in 10 mM HEPES-OH buffer pH 8.3, containing 100 mM NaCl, 1 mM MgCl$_2$, 0.2% Triton X-100, 4 mM PMSF, 10 µg/ml aprotinin and 10 µg/ml leupeptin. The extracts were centrifuged for 30 minutes at 4° C. and the supernatants were immediately loaded on an EHD1-affinity column.

Construction of EHD1—Affinity Columns and Purification of EHD1-Interacting Proteins:

2–5 mg of purified EHD1 protein was coupled to 1 ml of CNBr-activated Sepharose 4B (Sigma Chemicals Co.) according to the manufacturer's instructions. Briefly, CNBr-activated sepharose 4B was washed once in 1 mM HCl. Purified EHD1 protein was dissolved in coupling buffer containing 0.1 M NaHCO$_3$ pH 8.3, 0.5 M NaCl and incubated with the Sepharose suspension for 18 hours at 4° C. The remaining active CNBr groups were blocked by incubation with 0.2 M glycine pH 8.0 at room temperature for 1 hour. Excess of unabsorbed protein was washed away by re-suspending the sepharose beads in coupling buffer.

Protein-Sepharose conjugates were immediately incubated with rat testis extracts for 4 hours at room temperature. Following washes in the homogenization HEPES-OH buffer, EHD1-interacting proteins were eluted with 0.1 M glycine pH 3.7.

Genetic Mapping of the Mouse EHD1 Gene:

Genetic mapping of the mouse EHD 1 gene was performed by analysis of 2 multilocus crosses. Southern blot analysis, using an EHD1 cDNA probe identified a PstI fragment of 2.7 kb in M. spretus, 3.0 kb in M. m. musculus and 6.0 kb in NFS/N and C58/J. DNA inheritance of the variant fragments was followed in two sets of crosses: (NFS/N or C58/J) X M. m. musculus) X M m. musculus (Kozak et al., 1990) and (NFS/N X M spretus) X M. spretus or C58/J (Adamson et al., 1991) and compared with the inheritance of other markers previously typed in these same DNAs, including the Chromosome 19 markers: Ptprcap (protein tyrosine phosphatase, receptor type c polypeptide associated protein), Fth (ferritin, heavy), Cd5 (cluster designation 5), Pcna-ps2 (proliferating cell nuclear antigen, pseudogene 2), as described previously (Takai et al., 1996). Recombination was determined according to Green.(Green, 1981), and genes were ordered by minimizing the number of recombinants.

EXPERIMENTAL RESULTS

Isolation and Characterization of Human and Mouse cDNA Clones Encoding EHD1:

A chimeric phage was isolated from a mouse genomic library, screened with a prosaposin probe which contained two genomic fragments; prosaposin (Sandhoff et al., 1995) and a non-related sequence (FIG. 1). Using the GenHunt program (Compugen) and the Smith-Waterman algorithm (Wisconsin Sequence Analysis Package) several potential exons were identified within the non-prosaposin sequence. A fragment, bordered by the restriction enzymes MunI and HincII (FIG. 1, "probe") and containing one of the putative exons, was isolated and used as a probe to screen a human cerebellar cDNA library. The isolated cDNA was used as a probe to clone the corresponding mouse cDNA. The human and the mouse inserts were sequenced. Comparison of the sequences with the available databases indicated the existence of several homologous sequences, some of which were ESTs while one other was a cloned cDNA. Several C. elegans ESTs were combined to form a full-length cDNA (D69920, yK540gl.5, D69237, C69242, C60364, C47739).

As shown in Table 3, there was 79% homology between the human and the mouse sequences and 64.2% homology between the C. elegans and the human sequences.

Comparison of the predicted protein sequences revealed homology of 93.7 % between the human and the mouse proteins and a striking 74% homology between the C. elegans and the human counterpart (Table 3).

TABLE 3

Homology between different EHD1 cDNAs and EHD1 proteins

|  | Mouse | Drosophila | C. elegans |
| --- | --- | --- | --- |
| Human | 79 | 68.3 | 64.2 |
| Mouse |  | 66.9 | 64.2 |
| Drosophila |  |  | 69.7 |
| Human | 93.7 | 66.5 | 74 |
| Mouse |  | 67.4 | 73.2 |
| Drosophila |  |  | 84.5 |

Homology (in percentage) between different EHD1 cDNAs (the first three rows) and between different EHD1 proteins (numbers in bold, in the three last rows) as predicted by computer analysis.

Figures 3A, 3B:
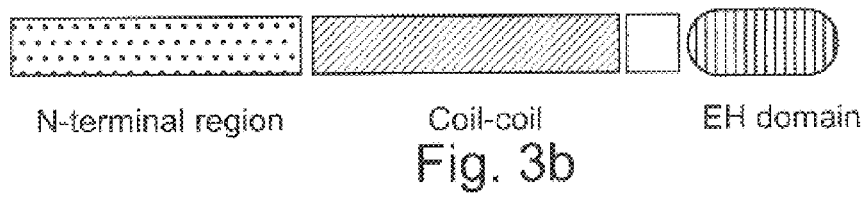
FIGS. 3a–b demonstrates multiple alignment of several EHD1 proteins and an illustrated protein structure, respectively. (3a)—amino acid homology between several proteins is shown. Identical amino acids are shaded with black, similar—with gray. Accession numbers are as follows: human EHD1 (human, SEQ ID NO:4): AF099011; mouse EHD1 (mouse, SEQ ID NO:5): AF099186; C. elegans (celeg, SEQ ID NO: 14) ESTs—D69920, yK540g1.5, D69237, C69242, C60364, C47739; Drosophila PAST-1 (dros, SEQ ID NO:15)—U70135. The region underlined with a thick line represents the central domain, containing the coiled-coil structure. The region underlined with a double line contains the EH domain. (3b)—an illustration of the EHD1 protein structure. The regions encoding the different protein domains are shown.

The mouse and human predicted proteins are 534 amino acids in size. They do not have conserved leader signals, glycosylation signals or nuclear localization signals. However, as shown and illustrated in FIG. 3, they do have an EH domain, including an EF-Ca$^{2+}$ binding motif, at their C-terminus, a highly conserved ATP/GTP binding domain (GxxxxGKTxxxxxxV, SEQ ID NO:16) at their N-terminus (Jakob et al., 1996) and a central coiled-coil structure. Due to the existence of the EH domain, the corresponding genes were designated EHD1 (EH domain containing 1).

Figure 2:
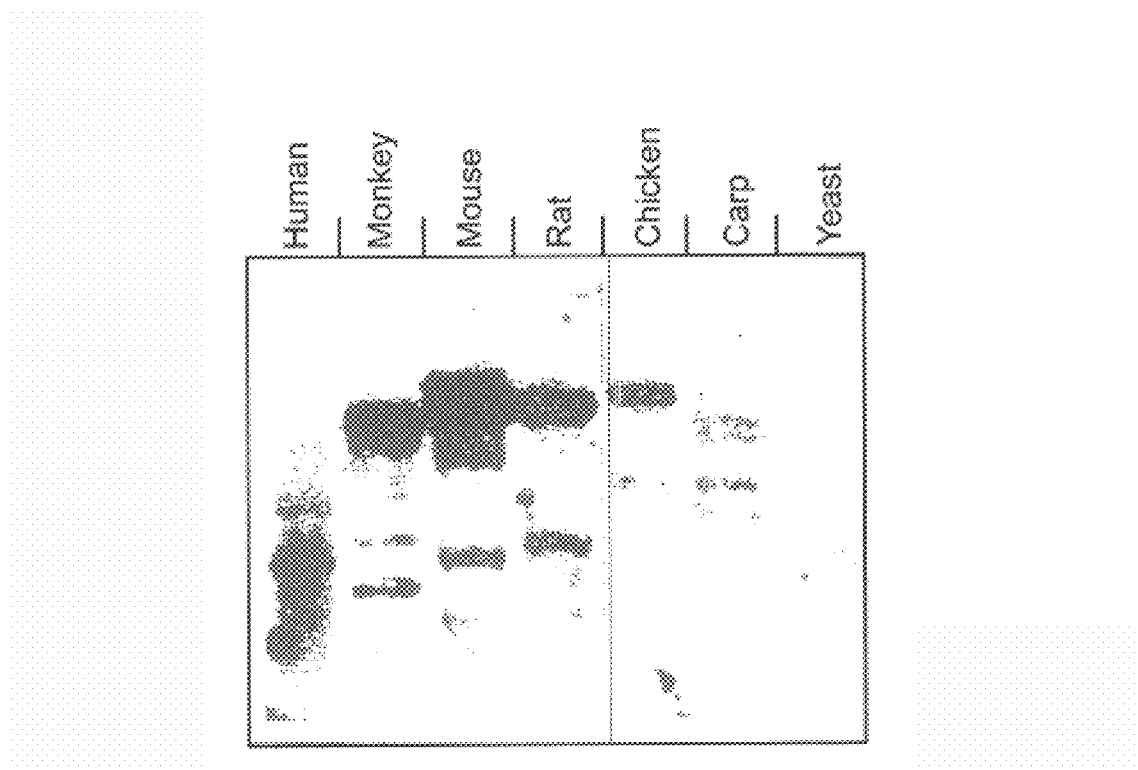
FIG. 2 demonstrates conservation of EHD1 among the animal Kingdom. 10 μg of DNA samples derived from the specified organisms were digested with the restriction enzyme EcoRI, electrophoresed through 0.7% agarose gel and blotted onto nitrocellulose filter. The filter was hybridized with 32P-labeled human EHD1 cDNA as a probe.

Conservation of the EHD1 gene could be demonstrated by Southern blot analysis (FIG. 2) showing hybridizable sequences also in monkey, rat, chicken and carp.

Figure 4A:
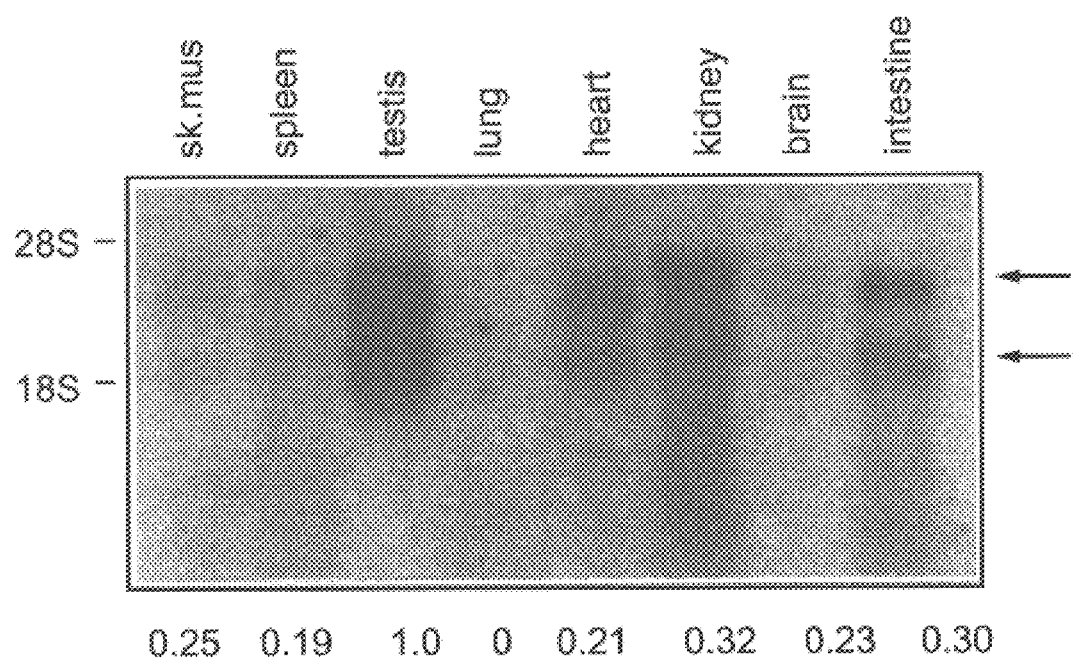
FIGS. 4a–b demonstrate the expression pattern of EHD1. (4a)—RNA was extracted from several mouse organs as described in Materials and Experimental Methods. The RNA was electrophoresed through a formaldehyde-agarose gel, blotted and hybridized with $^{32}$P-labeled human EHD1 cDNA. The filter was stripped and rehybridized to human $^{32}$P-labeled rRNA cDNA. The blot was quantified using phosphor-imager (Agfa Bass) and the amount of EHD1 RNA in each organ was normalized in comparison to the amount of rRNA in the corresponding organ. The numbers present the relative amount of EHD1 RNA in the different tissues in comparison to that found in testis (1.0). (4b)—a commercial RNA blot (Clontech, USA), was hybridized with $^{32}$P-labeled human EHD1 cDNA. The filter was stripped and rehybridized to human $^{32}$P-labeled rRNA cDNA. Since the RNA amounts in the different lanes were very similar no normalization was needed.

RNA Expression:

To study the expression pattern of the new gene, RNA was extracted from several adult mouse organs and Northern blot analysis was performed. The same blot was rehybridized with a ribosomal RNA cDNA as a control probe. As shown in FIG. 4a, two RNA species were evident, 3.6 and 2.0 kb in length, with highest levels in the testis. Lower levels were evident in other organs. 3'-RACE analysis (FIGS. 5a–b) indicated that these RNAs result from use of two different polyadenylation signals, which are 1600 nucleotides apart. To this end, RNA extracted from a mouse cell line (CCL-226) was subjected to RT-PCR with a 3'-RACE kit, using a commercial primer specific to poly(A) tails (AUP) 5'-GGCCACGCGTCGACTAGTACTTTTTTTTTTTTTTT TT-3' (SEQ ID NO:23) and an EHD1 specific primer (GSP) 3'-GGCATTGATGATGTTGAGTGG-5' (SEQ ID NO:24). A second round of PCR, using an EHD1 nested primer (Npr) 3'-CGAGGAGTTTGCCCTGGCG-5' (SEQ ID NO:25) was performed and the resulting fragments (Four fragment were obtained, two larger and two smaller) were sequenced. The sequence demonstrated that in each doublet, the larger fragment corresponded to an RNA species that derived from a bona fide poly(A) signal in the cDNA and the two polyadenylation signals are 1600 bp apart.

Northern blot analysis was also performed on human RNA from several adult organs and the results indicated the existence of three EHD 1 RNA species, 3.6, 3.2 and 2.0 kb in length, with the smaller one being highly expressed in testis. The 3.2 kb mRNA results from exon 3 skipping, as indicated by RT-PCR and its existence was demonstrated in the mouse too (Results not shown). It is therefore plausible that the three mouse EHD 1 MRNA species were not resolved under the conditions used for the RNA gel electrophoresis.

Figure 4B:
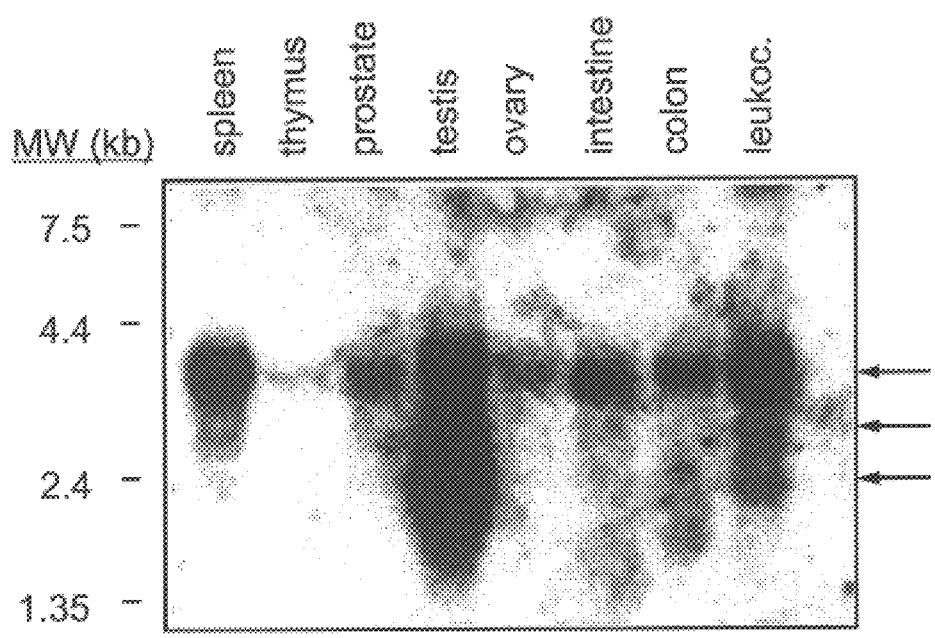

Northern blot analysis was also performed on human RNA from several adult organs and the results indicated (FIG. 4b) the existence of three EHD1 RNA species, 3.6, 3.2 and 2.0 kb in length (indicated by arrows), with the smaller one being highly expressed in testis. The 3.2 kb mRNA results from exon 3 skipping, as indicated by RT-PCR and its existence was demonstrated in the mouse too (results not shown). It is therefore plausible that the three mouse EHD1 mRNA species were not resolved under the conditions used for the RNA gel electrophoresis.

Figures 6A, 6B, 6C:
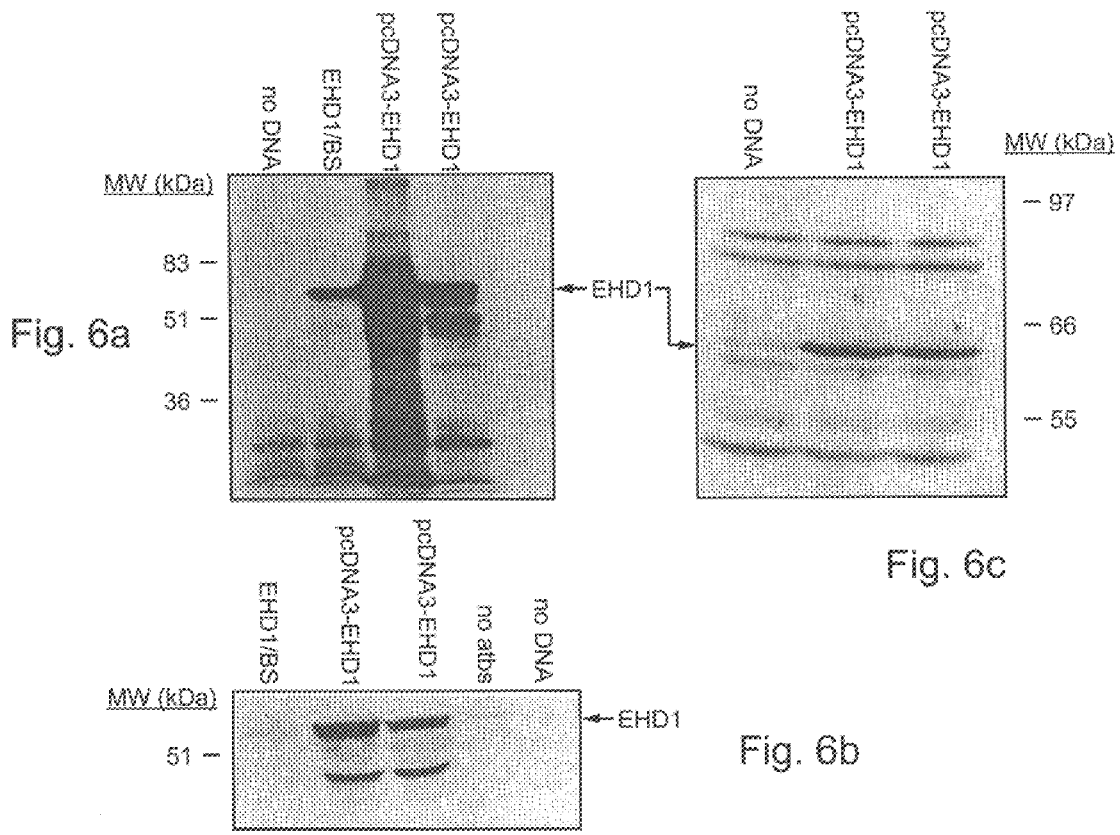
FIGS. 6a–c demonstrate human EHD1 cDNA expression in humans. Human EHD1 cDNA cloned in pBlueskript (Stratagene) (EHD1/BS) or in pcDNA3 (Invitrogen, USA) (pcDNA3-EHD1) was expressed using the TNT Coupled Transcription/Translation Reticulocyte Lysate System according to the manufacturer recommendation (Promega, USA). The protein products, before (6a) or after (6b) immunoprecipitation with anti-human EHD1 antibodies, were analyzed on a 10% SDS-PAGE. The gel was dried and exposed to a X-ray film. (6c)—COS cells were transfected with 10 μg of plasmid DNA (pcDNA3 or pcDNA1) into which the open reading frame of human EHD1 was introduced (pcDNA3-EHD1 and pcDNA1-EHD1, respectively) as described in the Materials and Experimental Methods section. 72 hours later, cell lysates were prepared and samples containing the same amount of protein were subjected to SDS-PAGE. Following electroblotting, the filter was reacted with anti-human EHD1 antibodies (atbd). The visualization was performed using the ECL procedure.
Figure 9A:
FIGS. 9a–d demonstrate intra cellular localization of EHD1. COS cells were transfected with a plasmid harboring the GFP coupled to a human EHD1 cDNA fragment. 48 hours later, rhodamine conjugated transferrin endocytosis was performed. Cells were fixed and visualized using confocal microscopy. Shown are representative confocal microscopic images depicting the cellular distribution of the green fluorescent protein-EHD1 (green, 9a) and transferrin (red, 9b). Overlay images depict colocalization of green fluorescent protein-EHD1 and transferrin (yellow, 9c). (9d)—enlargement of a segment of FIG. 9c (inset) containing yellow granules. Arrows in FIGS. 9c and 9d point to respective locations.
Figure 9B:
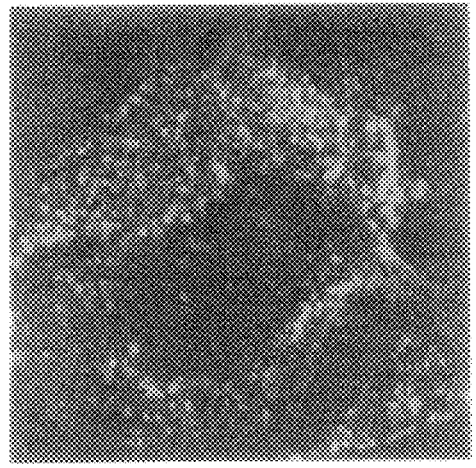
Figure 9C:
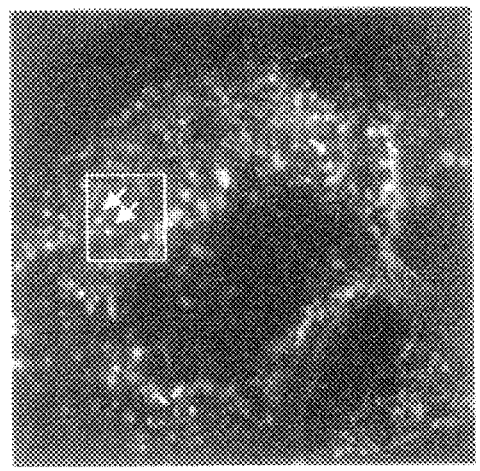
Figure 9D:
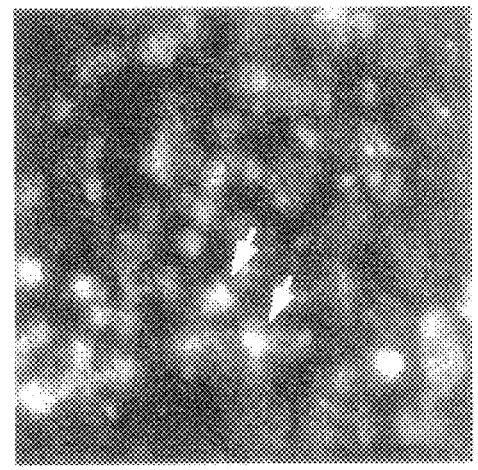
Figure 10A:
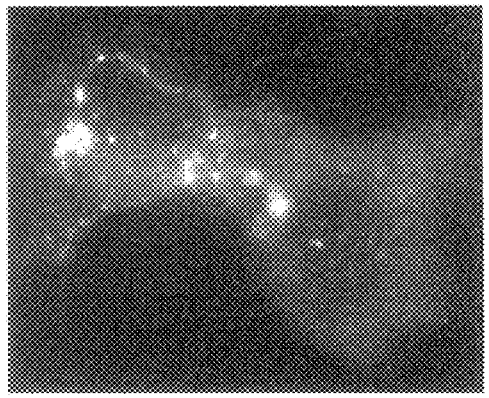
FIGS. 10a–d demonstrates the cellular localization of normal and deleted green fluorescent protein (GFP)-EHD1 fusion proteins. COS cells were transfected with plasmids harboring either the GFP coupled to the entire human EHD1 cDNA ORF (10b), cDNA fragments lacking the N-(10b) or C-(10c) terminal portions of human EHD1 cDNA, or with GFP alone (10d), as control. 18 hours later, cells were fixed and visualized using fluorescent microscopy. Shown are representative microscopic images depicting the cellular distribution of the GFP-EHD1.
Figure 10B:
Figure 10C:
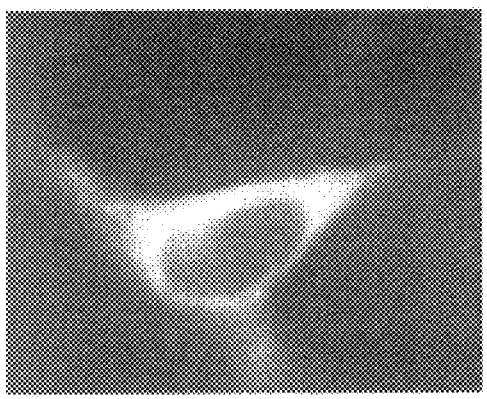
Figure 10D:
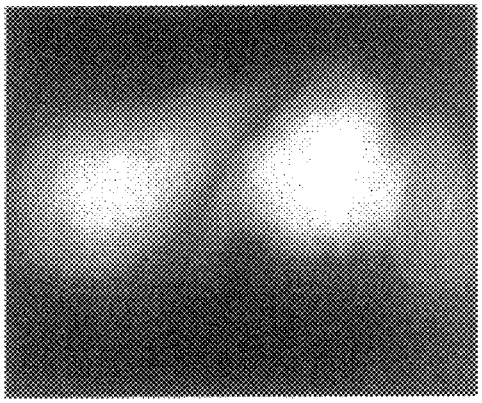

Human EHD1 cDNA Expression:

To gain some insight on EHD1, the human cDNA in pBlueskript (that derived from excision of a λzap phage containing a human EHD1 CDNA insert) or in pcDNA3 (pcDNA3-EHD1) was in vitro transcribed and translated and the products separated on SDS-PAGE, before or after immunoprecipitation with anti-human recombinant EHD1 antibodies. The antibodies were obtained by subcloning a 2 kb human EHD1 cDNA fragment in pET-28b, expressing it in E. coli strain DE3 and injecting the recombinant EHD1 into rabbits, following its purification on a nickel column. The results (FIGS. 6a–b) indicated that the human EHD1 cDNA encoded a major 62 kDa protein product. Some smaller molecular weight proteins were evident too. The predicted molecular weight of EHD1 is 60.8 kDa, which corresponds well with the experimental results. The same vector (pcDNA3-EHD1) or the human EHD1 cDNA coupled to the pcDNA1 vector (pcDNA1-EHD1), were used to transfect COS cells. Cell lysates were prepared 72 hours after transfection and samples were electrophoresed through SDS-PAGE after which immunoblotting was performed, using anti-human EHD1 antibodies. As shown (FIG. 6c), synthesis of one major protein was directed by the human EHD1 cDNA in COS transfected cells with molecular weight comparable to that of the major in vitro product. This result indicates that EHD1 does not undergo a major post-translational modification that significantly alters its molecular weight, however, it is anticipated that EHD1 is phosphorylated by the receptor it binds, as EHD1 has several putative phosphorylation sites, e.g., at locations Tyr233 and Tyr306 of human EHD1 protein (SEQ ID NO:4) and their equivalent locations in the mouse EHD1 protein (SEQ ID NO:5).

Expression Pattern of EHD1 in Mouse:

To determine the expression pattern of EHD1 in adult mouse and during embryogenesis, in situ hybridization and immunohistochemical analyses were performed. Immunohistochemical analysis of adult tissues indicated that EHD1 is expressed in specific cell types. In the testes (FIG. 7a as compared to 7b), EHD1 was expressed in germ cells during meiosis (e.g., spermatogonia, spermatocytes), but not in sperm cells. Adipocytes also showed EHD1 expression (FIG. 7c as compared to 7d). In the retina, EHD1 was expressed in the outer nuclear layer in the rods and cones, in the internal nuclear layer which houses the cell bodies of various associated glial cells and in the ganglion cell layer (FIG. 7e as compared to 7f). In the uterus, EHD1 was expressed at low levels in the basal membrane of the endometrium and to a higher extent in the peripheral muscle cells (not shown). After induced ovulation, EHD1 expression was detected in the granulosa cells (not shown). There was no notable expression in the spleen, liver or brain. During embryogenesis there was a peak of EHD1 expression in all cartilage of the ribs and spine vertebrae undergoing hypertrophy before ossification, at day 15.5 post coitus (FIGS. 8a–f). Whole mount RNA in situ analysis showed that EHD1 expression could be detected by day 9.5 in the limb buds and in the pharyngeal arches (not shown). At day 10.5 there was expression in the limb buds, sklerotomes, at various elements of the branchial apparatus (mandible and hyoid) and in the occipital region (FIG. 8g). At day 15.5 EHD1 expression peaked in cartilage, preceding hypertrophy and ossification.

Cellular Localization of EHD1:

The predicted structure of EHD1 includes an EH domain, shown to be present in eps15 and other related genes which are thought to regulate interactions between proteins required for endocytosis as well as other processes (Di Fiore et al., 1997; Wendland and Emr, 1998). It was therefore interesting to test whether EHD 1 associates with endocytic vesicles, which would indicate that it also mediates protein interactions required for endocytosis. To test this, the human EHD1 cDNA, through its N-terminus, was fused to GFP sequences and expressed in 293, HeLa and Cos cells. 48 hours after transfection, rhodamine conjugated transferrin endocytosis was performed. The cells were fixed and visualized using confocal microscopy. The results (FIGS. 9a–d) indicated that EHD1 was localized to several cytoplasmic vesicular structures, including the Golgi apparatus. There was colocalization of GFP-EHD1 with the rhodamine-conjugated transferrin, to endocytic vesicles.

Cellular Localization of Deletion Mutants of EHD1:

Mutant GFP-EHD1 proteins, missing either the N-terminal domain or the EH containing C-terminal region of EHD1 were created and used for transfection as explained above. For the N-terminal deletion, the GFP-EHD1 plasmid was digested with BamHI to remove a 700 bp fragment, the ends were blunted with the Klenow fragment of E. coli DNA polymerase, and it was self ligated. For the C-terminal mutant, the GFP-EHD1 plasmid was digested with HincII to remove a 600 bp fragment and self ligated. As shown in FIGS. 10a–d, the mutant proteins failed to localize to the endocytic vesicles, after 18 hours of transfection.

Figure 11:
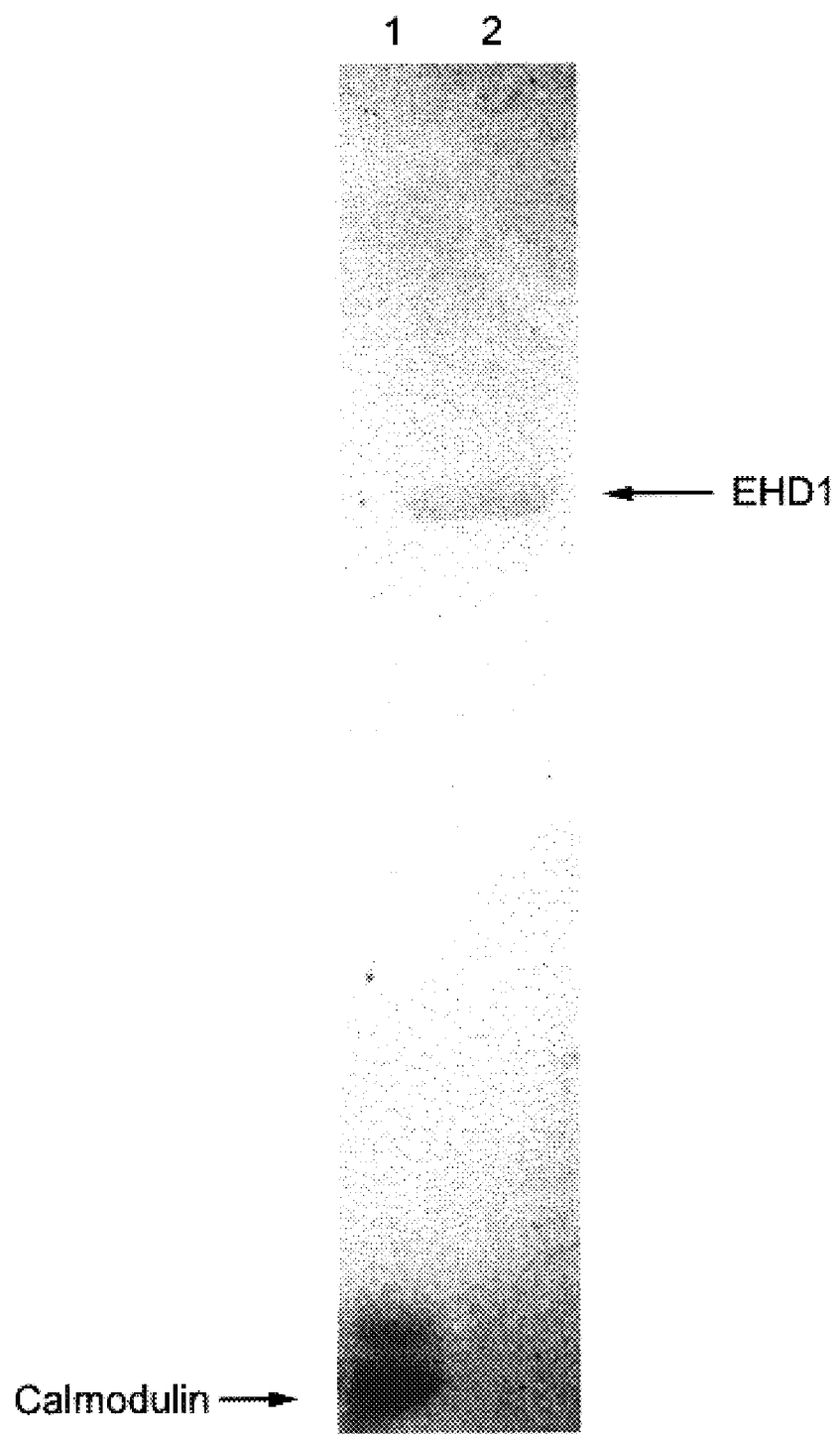
FIG. 11 demonstrates that EHD1 binds $Ca^{2+}$. Recombinant calmodulin or EHD1 were electrophoresed through an SDS-PAGE which was then electrblotted onto a filter. The filter was then stained with ruthenium red.

$Ca^{2+}$ Binding by EHD1:

$Ca^{2+}$ binding experiments, in which a blot containing recombinant EHD1 and calmodulin, a known $Ca^{2+}$ binding protein, were reacted with ruthenium red, show $Ca^{2+}$ binding to EHD1 (FIG. 11).

Figure 12:
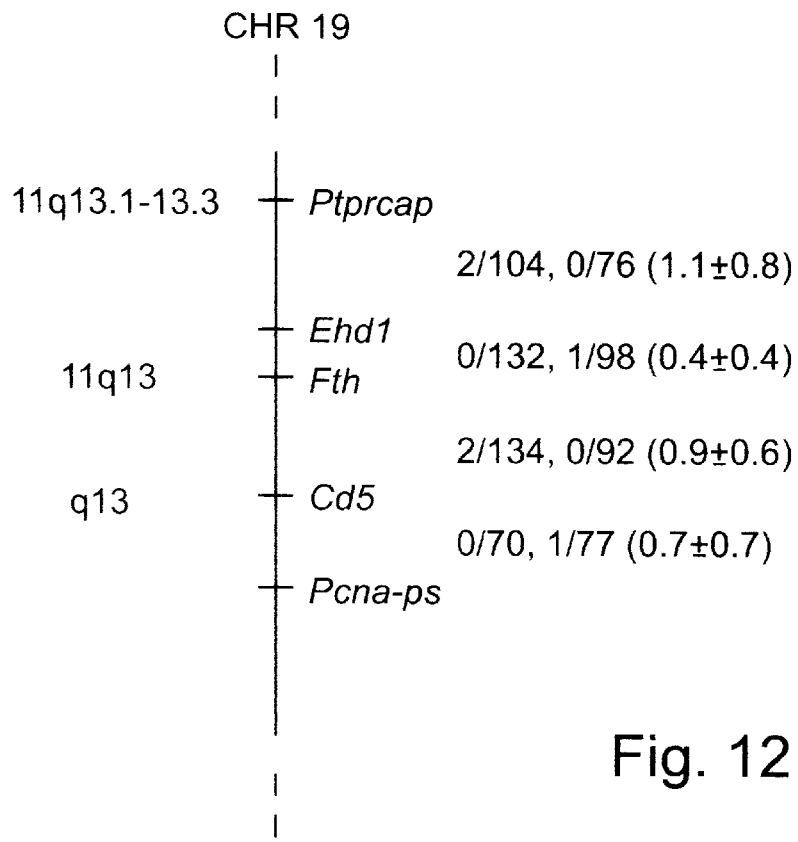
FIG. 12 is a map illustrating the position of the mouse EHD1 gene. Mapping was performed as described in the Materials and Experimental Methods section. Ptprcap—protein tyrosine phosphatase, receptor type c polypeptide associated protein; Fth—ferritin, heavy; Cd5—cluster designation 5; Pcna-ps2-proliferating cell nuclear antigen, pseudogene 2; EHD1—mouse EH domain containing 1.

Mapping of the Mouse and the Human EHD1 Gene:

Genetic mapping of the mouse EHD1 gene was performed by Southern blot analysis of 2 multi locus crosses: ((NFS/N or C58/J X M. m. musculus) x M. m. musculus and (NFS/N X M. spretus) X M. spretus or C58/J) and compared with the inheritance of other markers previously typed in these same DNAs. As shown (FIG. 12), the gene for EHD1 maps to proximal Chromosome 19 near Fth. The mouse PstI polymorphism also was used to map EHD1 on the Jackson Laboratory map, using the BSS panel (results not shown). The results demonstrated mapping near the markers Chk, Sytr, D19Mit12 and D19Mit32. This places EHD2 in a region of conserved synteny between mouse chromosome 19 and human chromosome 11. Search of the Stanford radiation hybrid database revealed an STS that mapped to 11q13, which represents the 3' non-coding region of human EHD1. Therefore human EHD1 maps to 11q13 and is linked to the marker D11S4530.

Figure 13:
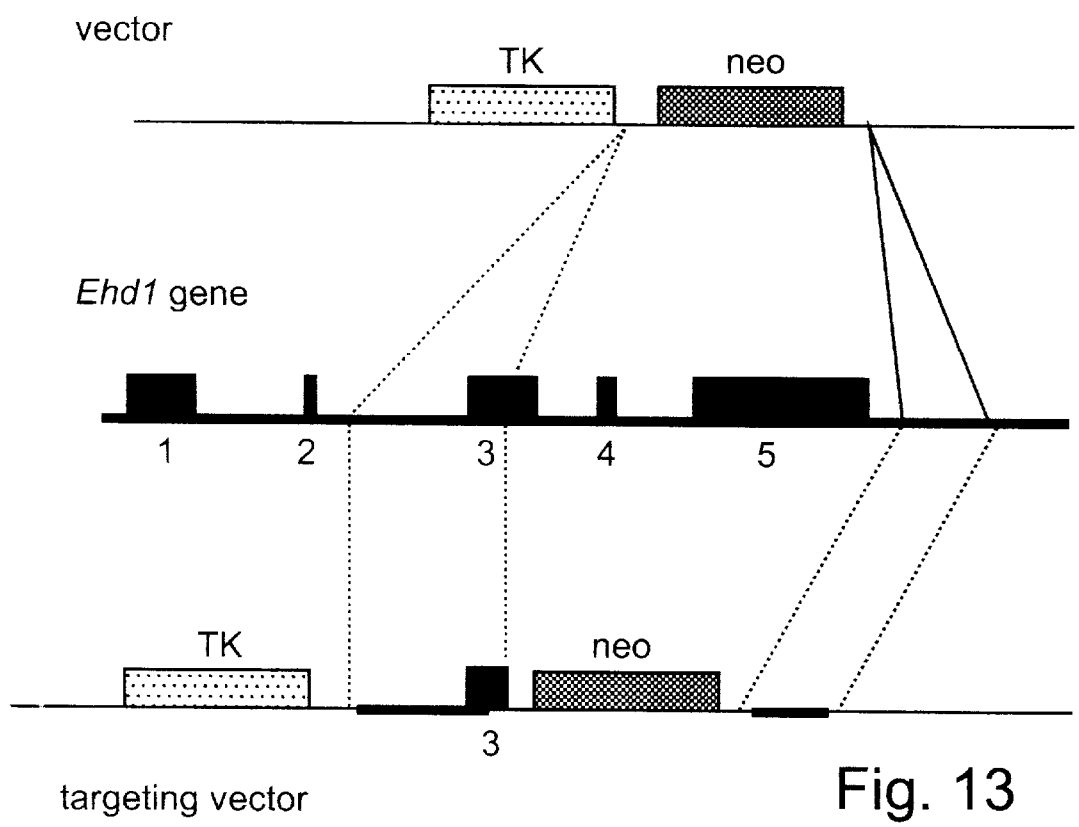
FIG. 13 demonstrates the construction of an EHD1 targeting vector for homologous recombination. Two mouse EHD 1 genomic fragments were introduced into a vector containing the thymidine kinase (TK, negative selection) and the neomycin resistance (aminoglycoside phosphotransferase, positive selection) genes. The upstream fragment was cloned between the neo and the TK genes, while the 3' fragment was cloned downstream of the neo gene. The EHD1 genomic fragments are depicted by thick lines. 1–5—EHD1 exons; neo—the $neo^r$ gene.
Figure 15A:
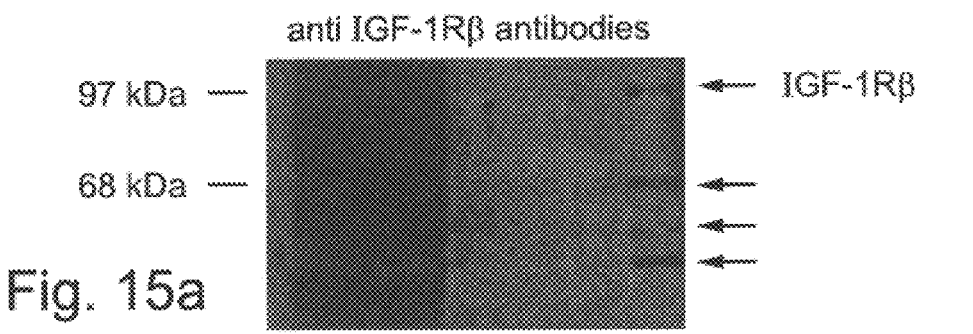
FIGS. 15a–d demonstrate protein—protein interactions of EHD1. Rat testis lysate was reacted with an EHD 1 column and after washes, bound proteins were eluted with low pH. Samples from the original lysate (L), the flowthrough (FT), washes (W) or the eluted material (E1, E2) were subjected to SDS-PAGE, which was immunoblotted and reacted with different antibodies: (15a)—anti-IGF1 receptorβ antibodies; (15b) anti-EHD1-antibodies; (15c)—anti-AP-2 antibodies; (15d)—anti-clathrin antibodies.
Figure 15B:
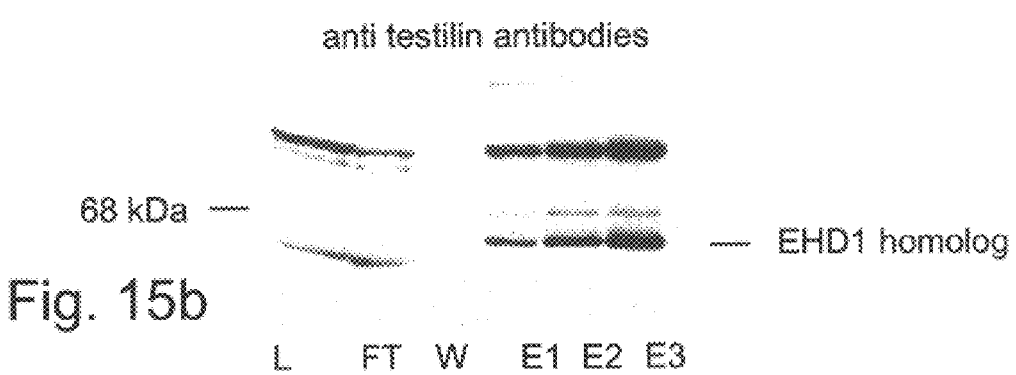
Figure 15C:
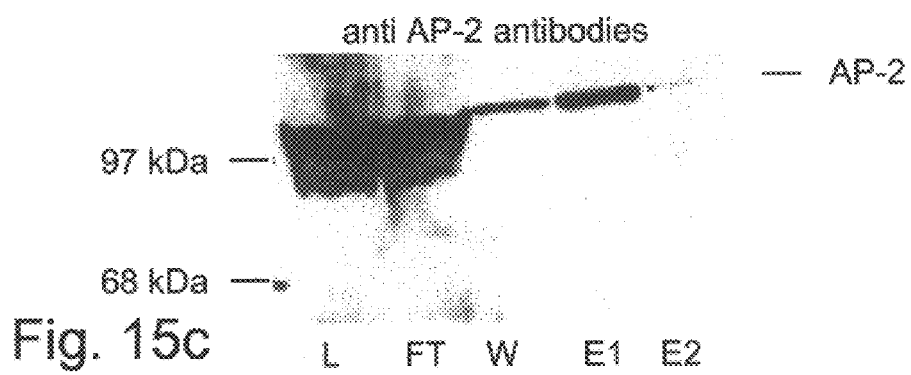
Figure 15D:
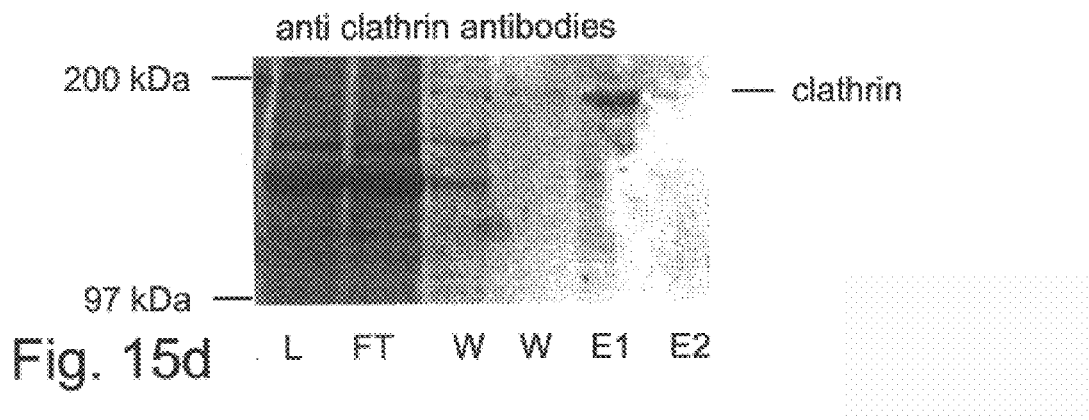
Figure 16:
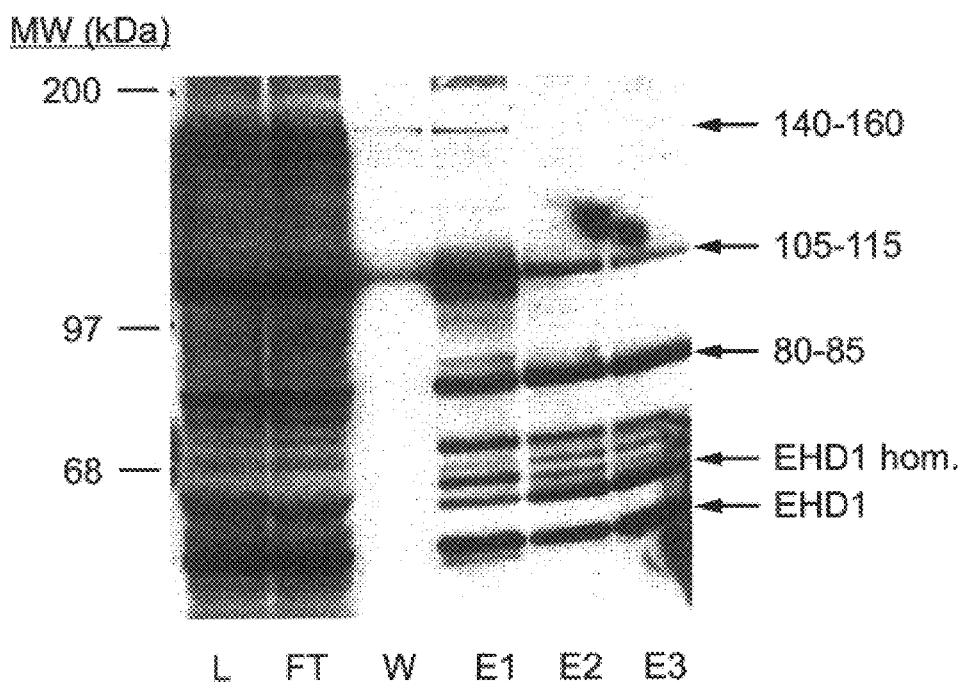
FIG. 16 demonstrates an overlay assay after trapping of complexes on an EHD1 column. Rat testis protein lysate was loaded on an EHD1 column and following washes, bound fractions were eluted. These fractions were immunoblotted after SDS-PAGE, overlaid with recombinant EHD1 and interacted with anti EHD1 antibodies. L-lysate; FT-flowthrough; E-eluted fraction.
Figure 17:
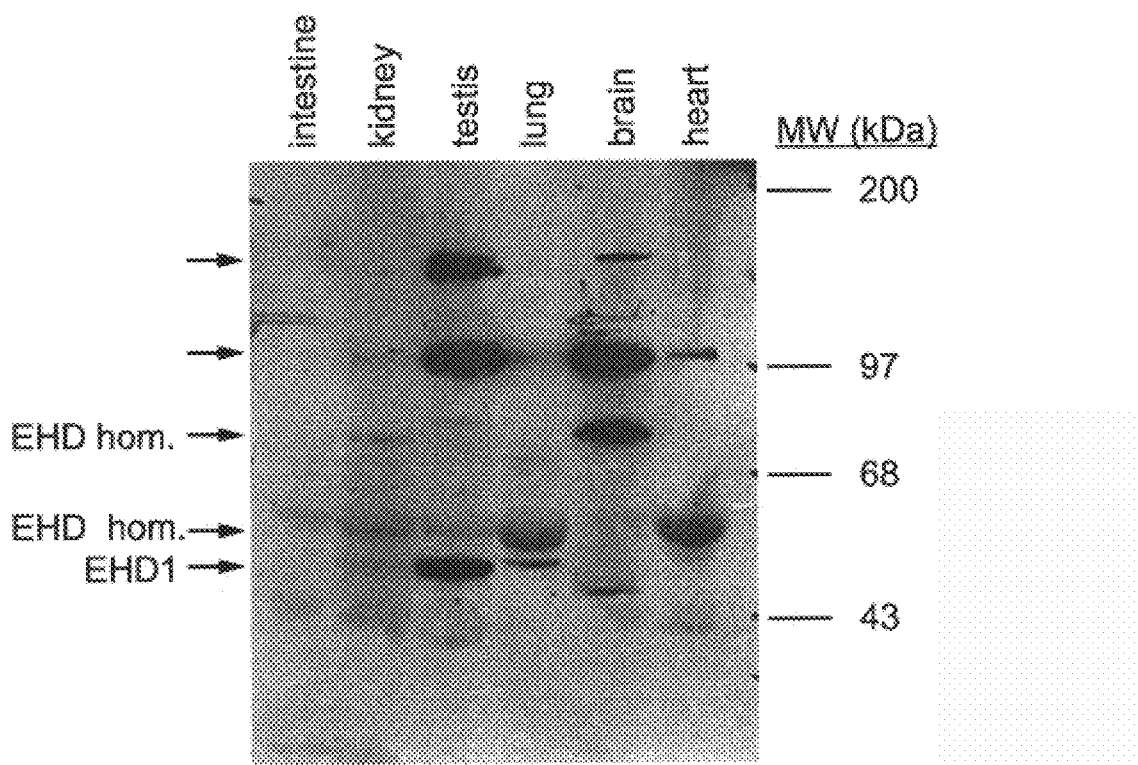
FIG. 17 demonstrates an overlay assay. Protein lysates from several adult mouse tissues as indicated were resolved on an SDS-PAGE, after which they were immunoblotted, overlaid with recombinant EHD1 and interacted with anti EHD1 antibodies. The arrows depict the interacting proteins.

Creation of a Knock-Out Mouse Model:

To further understand the biological role and importance of EHD1, a mutant mouse in which the EHD1 gene is not expressed is pursued using gene targeting technology. To this end, the mouse EHD1 genomic structure was explored. A 129/SVev mouse genomic library in lambda FIXII was screened and several EHD1 positive clones were obtained. All intron-exon junctions were established and 13 kb were sequenced and is shown in SEQ ID NO:3. As shown in FIG. 13, a targeting vector has already been constructed, which can be used for creation of chimeric mice. The vector includes negative (TK) and positive (neo) selection markers, wherein the positive selection marker is flanked by genomic sequences derived from the mouse EHD1 gene.

To this end, the vector will be introduced into 129/SVev derived embryonic stem (ES) cells via electroporation. Selection of colonies in media containing G418 and Gancyclovir will be performed and positive clones will be tested for correct integration (homologous recombination) between the introduced gene and the endogenous EHD1 gene using Southern blot analysis with external genomic probes. At least 3 targeted ES cell lines will be used to make chimeric mice by morulae aggregation and then chimeras will be bred to produce heterozygous mutant mice. Heterozygotes will be intercrossed to produce homozygous mutant animals. (Bedell et al., 1997) It is possible that homozygous mutant embryos will not reach it to birth. In this case, embryos will be analyzed at different stages during embryogenesis and compared to normal embryos. An inability of the mutant embryos to reach it to birth would demonstrate the importance of EHD1 during development and a comparison of the normal and the mutated embryos will allow identification of organs, defective and/or retarded in their development.

EHD1 and Genetic Diseases:

As stated in U.S. application Ser. No. 09/026,898, a direct linkage between BBS1 and EHD1 was searched for. To this end, PCR conditions were established for the human EHD1 gene to find linkage between EHD1 and BBS1, thus making EHD1 a good candidate for BBS1. All exon-intron junctions as well as intronic sequences from 50 BBS1 patients were tested by SSCP and direct sequencing of PCR amplified fragments but no mutation has been found, thus excluding EHD1 as the candidate gene for BBS1.

It was also suspected that EHD1 is the candidate gene for osteochondrodystrophy (ocd). In an effort to demonstrate that this is so, testis RNA and genomic DNA were extracted from ocd and the parental animal (C3H). Results of RT-PCR on RNA and PCR on genomic DNA (FIG. 14) indicated several (23) single nucleotide changes around the initiator ATG, none of which results in an amino acid substitution. However, such changes at the RNA level, may cause a major change in the RNA secondary structure and/or its stability, leading to a change in its translation efficiency.

Characterizing and Isolating the Proteins that Bind, Directly or Indirectly, to EHD1:

In order to find proteins that directly or indirectly bind to EHD1 or are associated with it in a complex, mouse organ extracts were prepared and loaded on an EHD1 column. Eluted fractions were resolved on an SDS-PAGE and their immunoblots were decorated with antibodies against known proteins of the endocytic machinery, like: α-adaptin, which is a component of the AP-2 complex (AP-2 complex is a tetramer of α adaptin~100 kDa, β adaptin~100 kDa, μ adaptin~47–50 kDa and σ adaptin~17–19 kDa), clathrin, which binds to the AP-2 complex, EHD2 itself and IGF1 receptor as the putative candidate for modifying and binding EHD1. The results (FIGS. 15a–d) demonstrate that EHD1 is found in a complex with all the above mentioned proteins, which are part of the endocytic vesicle.

To further characterize the proteins that form a complex (or are associated) with EHD1, fractions, eluted from the EHD1 column, were resolved on an SDS-PAGE and the immunoblots were decorated with recombinant EHD1. The decorated proteins were reacted with anti recombinant EHD1 antibodies and visualized.

In parallel, lysates were resolved through an SDS-PAGE and then overlaid with EHD1 and interacted with anti recombinant EHD1 antibodies.

As shown in FIGS. 15a–d and 16–17 several proteins including EHD1 reacted with EHD1, which was then identified via its interaction with the anti EHD1 antibodies. Few of these proteins such as the α-adaptin chain of the AP-2 complex and clathrin,(Sorkina et al., 1999) were identified.

To characterize the other proteins, extracts will be separated through 2D gels (native electrophoresis in one plane and isoelectric focusing in the orthogonal plane) and the overlay assays will be performed on them. The reacting proteins will be subjected to nanospray mass spectroscopy and the obtained sequences will serve as templates to design primers, which will be used to amplify cDNA sequences from a mouse testis cDNA library, (Yaron et al., 1998).

As an alternative a two hybrid system screen will be employed. The two hybrid screen is based on the ability of a binding domain of the yeast transcriptional activator lexA to be activated by the activating domain of the yeast transcriptional activator GAL4.(Chien et al., 1991). The binding domain is fused to a known, bait protein, while the activating domain is fused to protein sequences encoded by a library from any desired origin. In our case, the bait will be the human EHD1, while the library will be a human expression cDNA library.

IGF1 Receptor and EHD1:

To test the possibility that IGF1 receptor modifies and interacts with EHD1, IGF1 or insulin receptor overproducing cells (NIH3T3 or CHO cells, respectively, kindly provided by Drs. D. LeRoith, NIH, USA and Y. Zick, The Weizmann Institute of Science, Rehovot, Israel) were stably transfected with an EHD1 expression vector using the puromycin selection. The EHD1 expression vectors used were pcDNA1 or pcDNA3 (Clontech, USA), into which a 2 kb human EHD1 cDNA fragment containing the entire ORF was introduced in the sense or antisense orientation. For the sense orientation a 2 kb EcoRI-XhoI fragment was ligated to the vector digested with the same enzymes. For the antisense orientation, a 2 kb EcoRI-HindIII fragment was ligated to the vector digested with the same restriction enzymes.

Positive clones are being tested for overexpression of EHD1. Control cells, over-expressors and cells expressing low levels of the human EHD1 will be grown under starvation condition for insulin or IGF1. They will be treated with insulin or IGF1, respectively, and cellular protein lysates will be prepared. They will be immunopercipitated with anti insulin receptor β chain antibodies or anti IGF1 receptor β chain antibodies. The immunopercipitates will be analyzed by immunoblotting with anti EHD 1 antibodies. In a parallel experiment, the cellular proteins will be immunopercipitated with a monoclonal anti phospho tyrosine antibodies and then will be analyzed by immunoblot with anti EHD1 antibodies.

The results of these experiments will indicate whether EHD 1 gets phosphorylated following treatment with IGF1. To obtain direct evidence that IGF1 receptor is the physiological substrate of EHD1 immunocomplex kinase assays will be performed. To this end, lysates from cells overexpressing IGF1 receptor will be immunopercipitated with anti IGF1 antibodies and the immunopercipitates will be challenged with purified bacterial recombinant EHD1 in the presence of [γ-$^{32}$P] ATP, as a phosphate donor. Under these conditions, $^{32}$P incorporation into EHD1 can be followed by immunoprecipitation with anti EHD1 antibodies and SDS-PAGE or by recovery from an EHD1 column and SDS-PAGE (Fazioli et al., 1993).

It was already noticed that the NIH3T3 cells overexpressing EHD1 have a slower growth rate compared to their parental cells, indicating that overexpression of EHD1 abrogates the normal proliferation rate of these cells. Since these cells also overexpress IGF1 receptor the results may indicate the direct involvement of EHD1 in the normal signaling pathway regulated by binding to IGF1 receptor. This phenomenon was not noticed in the CHO cells overexpressing EHD 1 and insulin receptor.

The growth rate of the cells will be tested by counting them and by thymidine incorporation.

Moreover, the IGF1 and EHD1 overexpressing NIH3T3 cells seem to undergo apoptosis.

It has already been documented that IGF1 has an anti apoptotic effect. To this end, see, D'costa et al., 1998.

ISOLATION AND CHARACTERIZATION OF EHD2 MATERIAL AND EXPERIMENTAL METHODS

Libraries and Screening Procedures:

A mouse fetal brain cDNA library in Lambda Zap II vector (Stratagene, USA) was screened with a 400 bp fragment obtained from SEQ a mouse genomic clone (SEQ ID NO:8, which includes the genomic sequence shown in FIG. 1A of U.S. Pat. application Ser. No. 09/026,898) by PCR amplification using the primers: sense: 5'-CATGAATTCCTGCTTTG-3' (SEQ ID NO:17); and antisense: 5' GACTCAGAGTAGTTTAGG-3' (SEQ ID NO:18). Plasmids containing the corresponding cDNAs were excised from the phages following the manufacturer recommendations. Sequencing was according to Sanger using double stranded plasmid DNA.

A human fetal brain cDNA library in Lambda Zap (uni-Zap) vector (Stratagene, USA) was screened with a fragment prepared by PCR amplification using the following primers: sense: 5'-GCTGACCCTGCTCTGCC-3' (SEQ ID NO:26) and antisense: 5'-ACAAATGCACTGCAGTAG-3' (SEQ ID NO:27). Plasmids containing the corresponding cDNAs were excised from the phages following the manufacturer recommendations. Sequencing was according to Sanger using double stranded plasmid DNA.

RNA Extraction:

RNA was prepared from mouse organs using the TRIREAGENT kit (MRC, USA), according to the manufacturer's recommendations. RNA samples were electrophoresed through a 1% agarose gel containing formaldehyde and transferred onto a nylon membrane. Prehybridization was for 0.5 hour in 0.5 M Na-phosphate buffer pH 7.4, 7% SDS and 1 mM EDTA at 65° C. Hybridization was in the same buffer with 10×10$^6$ cpm of the appropriate probe at 65° C. for 18 hours. After one wash in 2×SSC, 0.1% SDS, for 15 minutes at 65° C. and several washes in 0.2×SSC, 0.1% SDS, at 65° C. the filter was exposed to an X-ray film. Phosphor-imaging analysis was performed as well.

Probe preparation: Probes were prepared by the random priming technique using commercial kits according to the manufacturers' recommendations.

Identification of a Polymorphic CA Repeat:

DNAs prepared from eight different mouse strains and the genomic EHD2 clone (SEQ ID NO:8) were amplified using the PCR technique, with the primers: sense: 5'-CTCCTCCCTCCATCTAA-3' (SEQ ID NO:19) and antisense: 5'-CTCAGACAAAGGTGTTCC-3' (SEQ ID NO:20). The antisense primers was end labeled by incubating 10 pmoles of the primer in the presence of 10 pmoles of γ-$^{32}$P-ATP with 10 units of T4 DNA polymerase for 30 minutes at 37° C. in 70 mM Tris-HCl pH 7.6, 10 mM MgCl$_2$ and 5 mM DTT. The PCR conditions were as follows: 10 minutes denaturation at 100° C. and then: 1 minute at 55° C., 1 minute at 72° C. and 1 minute at 92° C. for 30 cycles. The PCR products were resolved through a 6% urea-polyacrylamide sequencing gel.

Genetic Mapping of the Mouse EHD2 Gene:

Genetic mapping of the mouse EHD2 gene was performed by analysis of 2 multilocus crosses between *Mus. m. domesticus* (B) and *M. spretus* (S). DNA originated from these two parental strains and all the backcross DNA samples ((BxS)xB) and ((BxS)xS) (all the DNA samples were obtained from the Jackson Laboratories, Maine, USA) was amplified using the primers: sense: 5'-CTCCTCCCTCCATCTAA-3' (SEQ ID NO:21) and antisense: 5'-CTCAGACAAAGGTGTTCC-3' (SEQ ID NO:22). The DNA fragments were resolved on a 2.5% agarose gel and the data was sent to the Jackson Laboratory, were it was evaluated and linkage was established.

EXPERIMENTAL RESULTS

Isolation and Characterization of Mouse cDNA Clones Encoding EHD2:

Comparison of the EHD1 cDNA sequence (EQ ID NO:2) with that of the genomic clone (SEQ ID NO:8, which includes the genomic sequence shown in FIG. 1A of U.S. Pat. application Ser. No. 09/026,898) indicated that they contain similar but not identical sequences. Namely, the genomic clone contained exons with high homology to those of EHD1 but not identical. In order to clone the cDNA whose exons were contained within the genomic clone, two primers were used to amplify from the genomic clone what should present its 3' untranslated region as derived by homology to EHD1, as described in Materials and Experimental Methods. The obtained fragment was used to screen a cDNA library as described above. Positive inserts were sequenced. Comparison of the new sequence with that of EHD1 indicated high homology between them in the coding region and the predicted proteins, and much less so between their 5' or 3' untranslated regions (see FIGS. 18–21). There is 80.1% sequence identity between EHD1 and EHD2 coding regions and 84.6% homology between the two proteins. Comparison of the predicted protein sequences also revealed homology of 84% between the human EHD1 and the mouse EHD2 protein. The new mouse protein is 535 amino acids in size. It does not have a leader signal, glycosylation signal or nuclear localization signal. However, it does have an EH domain, including an EF-Ca$^{2+}$ binding motif, at its C-terminus, a highly conserved ATP/GTP binding domain (GxxxxGKTxxxxxxV, SEQ ID NO:16) at their N-terminus, a central coiled-coil structure and putative phosphorylation sites, very similar to that of EHD1. Therefore it was designated EHD2 (EH domain containing 2). Several ESTs were found in the database that included parts of the EHD2 3' UTR (AA268324; AA510832; AA163846; AA002645; AA260370; AA163846). However, non of them include any EHD2 coding sequences.

Isolation and Characterization of Human cDNA Clones Encoding EHD2:

Searching the EST databases revealed human ESTs (T03471; A708604) with homology to the mouse EHD2 3' UTR. According to this sequence two primers were synthesized, a sense primer: 5'-GCTGACCCTGCTCTGCC-3' (SEQ ID NO:28) and an antisense primer: 5'-ACAAATGCACTGCAGTAG-3' (SEQ ID NO:29).

These primers were used to amplify a 376 bp fragment from a human cDNA library. This fragment was used as a probe to isolate human EHD2 clones from a human fetal brain cDNA library. The clones are being sequenced and a partial sequence is set forth in SEQ ID NO:7 (cDNA) and 9 (protein). A CA repeat was found in the 3' untranslated region of the human EHD2 cDNA, which according to preliminary results seems to be polymorphic (data not shown).

Figure 22:
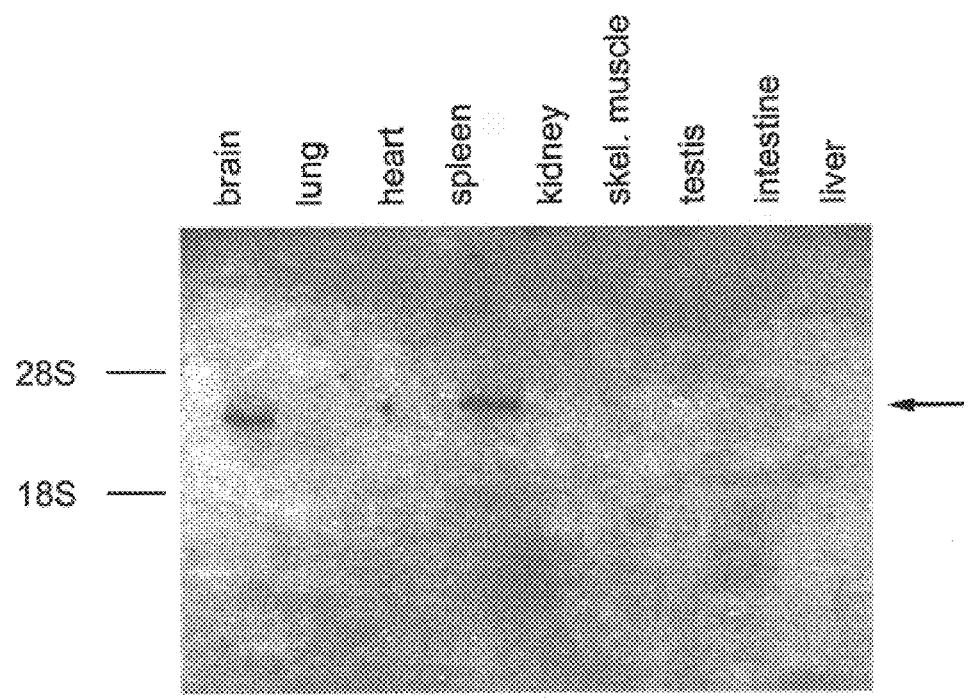
FIG. 22 demonstrates the expression pattern of EHD2. RNA was extracted from several mouse organs as described in Materials and Experimental Methods. It was electrophoresed through a formaldehyde-agarose gel, blotted and hybridized with $^{32}P$-labeled fragment of the 3'-UTR of the human EHD2 cDNA. The filter was stripped and rehybridized to human $^{32}P$-labeled rRNA cDNA (not shown). The blot was quantified using phosphor-imager (Agfa Bass).

EHD2 RNA Expression:

To study the expression pattern of the EHD2 gene, RNA was extracted from several adult mouse organs and Northern blot analysis was performed. As shown in FIG. 22, one RNA species was evident, 3.6 kb in length, in kidney and brain. It is possible that EHD2 is expressed in other organs as well, at quantities that are under the detection level of the method used.

Figure 23:
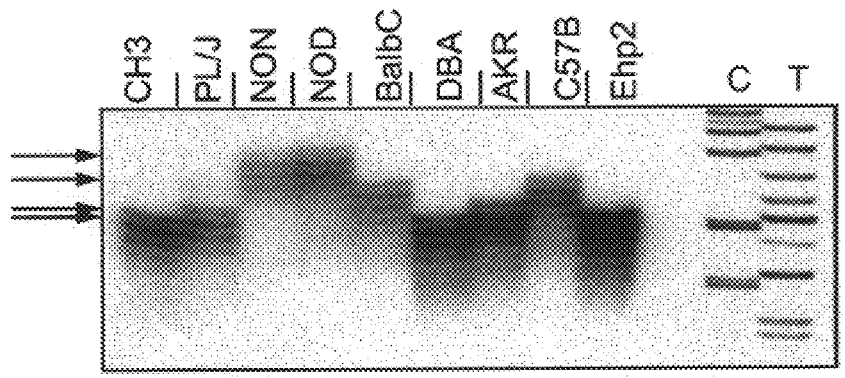
FIG. 23 demonstrates PCR amplification of the mouse EHD2 CA repeat. DNAs prepared from eight different mouse strains and the genomic EHD2 clone (SEQ ID NO:8) were amplified using the PCR technique, with two primers, as described in Materials and Experimental Methods. The PCR products were resolved through a 6% urea-polyacrylamide sequencing gel. The gel was dried and exposed to an X-ray film.

Mapping of the Mouse and the Human EHD2 Gene:

The mouse EHD2 cDNA was found to contain a CA repeat at its 3' UTR. To address the question whether this repeat is polymorphic, which makes it a good marker for linkage and mapping studies, DNAs prepared from eight different mouse strains and the genomic EHD2 clone were amplified using the PCR technique, with two primers, as described in Materials and Experimental Methods. The PCR products were resolved through a 6% urea-polyacrylamide sequencing gel. The results (FIG. 23) clearly demonstrated that the CA repeat is polymorphic, with at least 4 alleles among the 8 different DNA samples tested.

Figure 24A:
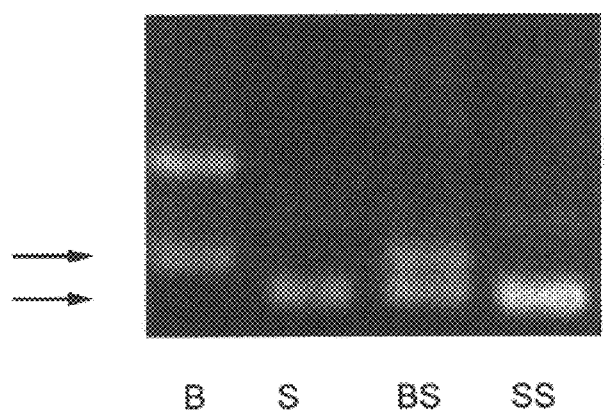
FIGS. 24a–c demonstrates mapping the mouse EHD2 gene. (24a)—Amplification of the CA repeat in the parental mouse strains M. m. domesticus (B) and M. spretus (S). (24b)—Amplification of DNA samples of the different panels DNAs obtained from the Jackson Laboratory was performed and samples were electrophoresed through a 2.5% agarose gels. (24c)—Schematic illustration of EHD2 map position, including loci mapped on chromosome 17, adjacent to the EHD2 locus.
Figure 24B:
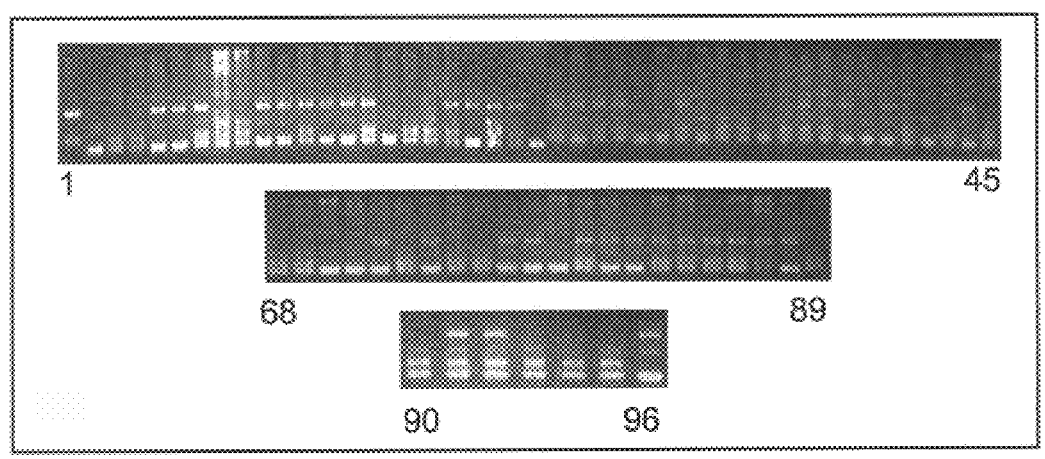
Figure 24C:
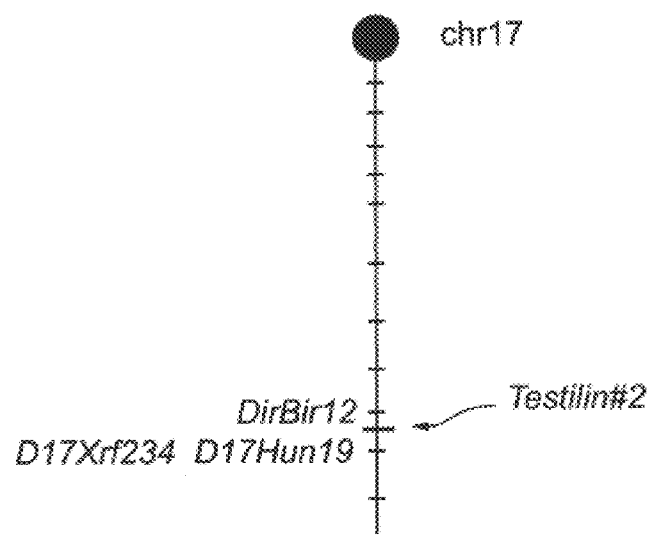

Genetic mapping of the mouse EHD2 gene was performed as described in Materials and Experimental Methods. The CA-repeat was amplified from the two parental strains and all the backcross DNA samples ((BxS)xB) and ((BxS)xS). The DNA fragments were separated by electrophoresis through a 2.5 % agarose gel (FIGS. 24a–b). The results indicated amplification of 3 fragments: an unrelated upper fragment and two lower, polymorphic fragments. In the DNA samples presented in FIG. 7a either both of them appeared or only the lower band at a double dose (representing two alleles). The results were submitted to the Jackson Laboratories and linkage was demonstrated to mouse chromosome 17q40–43, between the markers: DirBir12, and D17Hun19 and D17Xrf234 (FIG. 24c). This places EHD2 in a region of conserved synteny between mouse chromosome 17q40–43 and human chromosome 2p.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications cited herein are incorporated by reference in their entirety.

REFERENCES

1. Adamson, M. C., Silver, J. and Kozak, C. (1991). The mouse homolog of the gibbon ape leukemia virus receptor: Genetic mapping and a possible receptor function in rodents. Virol. 183: 778–781.
2. Baker, J., Hardy, M. P., Zhou, J., Bondy, C., Lupu, F., Bellve, A. R. and Efstratiadis, A. (1996). Effects of an Igf1 gene null mutation on mouse reproduction. Mol. Endocrinol. 10: 903–918.
3. Baraz, L., Friedler, A., Blumenzweig, I., Nussinuv, O., Chen, N., Steinitz, M., Gilon, H., and Kotler, M. (1998) "Human immunodeficiency virus type 1 Vif derived peptides inhibit the viral protease and arrest virus production" FEBS Letters 441:419–426.
4. Beales, P. L. Warner, A. M. Hitman, G. A. Thakker, R. and Flinter, F. A. (1997) "Bardet-Biedl syndrome: a molecular and phenotypic study of 18 families". J Med Genet 34: 92–98.
5. Bedell, M. A., Jenkins, N. A. and Copeland, N. G. (1997). "Mouse models of human disease. Part I: Techniques and resources for genetic analysis in mice". Genesand Development 11:1–11.
6. Benmerah, A., Lamaze, C., Begue, B., Schmid, S. L., Dautry, V. A. and Cerf, B. N. (1998). AP-2/Eps15 interaction is required for receptor-mediated endocytosis [In Process Citation]. J Cell Biol. 140: 1055–1062.
7. Bruford, E. A. Riise, R. Teague, P. W. et al (1997) "Linkage mapping in 29 Bardet-Biedl syndrome families confirms loci in chromosomal regions 11q13, 15q22.3–q23, and 16q21". Genomics 41: 93–99.
8. Burch and Mahan (1991) Oligodeoxynucleotides antisense to the interleukin I receptor m RNA block the effects of interleukin I in cultured murine and human fibroblasts and in mice. J. Clin. Invest. 88:1190.
9. Calabretta et al. (1991) Normal and leukemic hematopoietic cell manifest differential sensitivity to inhibitory effects of c-myc antisense oligodeoxynucleotides: an in vitro study relevant to bone marrow purging. Proc. Natl. Acad. Sci. USA 88:2351.
10. Callagham, J., Simonsen, A., Gaullier, J. M., Toh, B. H. and Stenmark, H. (1999) "The endosome fusion regulator early endosomal autoantigen 1 (EEA1) is a dimer" Biochem J 338:539–543.
11. Caplan, A. I. (1994). "The mesengenic process". Clin Plast Surg 21: 429–435.
12. Cao, H., Garcia, F. and McNiven, M. A. (1998). Differential Distribution of Dynamin Isoforms in Mammalian Cells. Mol. Biol. Cell 9: 2595–2609.
13. Carbone, R., Fre, S., Iannolo, G., Belleudi, F., Mancini, P., Pelicci, P. G., Torrisi, M. R. (1997). eps15 and eps15R are essential components of the endocytic pathway. Cancer Res. 57: 5498–5504.
14. Carmi, R., Elbedour, K., Stone, E. M. and Sheffield, V. C. (1995). Phenotypic differences among patients with Bardet-Biedl syndrome linked to three different chromosome loci. Am. J. Med Genet. 59: 199–203.
15. Chan, S. J., Plisetskaya, E. M., Urbinati, E., Jin, Y. and Steiner, D. F. (1997). "Expression of multiple insulin insulin-like growth factor receptor genes in salmon gill cartilage". Proc. Natl. Acad. Sci. USA 94: 12446–12451.
16. Chen, H., Fre, S., Slepnev, V. I., Capua, M. R., Takei, K., Butler, M. H., Di Fiore, P. P. (1998). Epsin is an EH-domain-binding protein implicated in clathrin-mediated endocytosis. Nature 394: 793–797.
17. Chien, C. T., Bartel, P. L., Sternglanz, R. and Fields, S. (1991). "The two-hybrid system: a method to identify and clone genes for proteins that interact with a protein of interest". Proc Natl Acad Sci U S A 88: 9578–9582.
18. Coda, L., Salcini, A. E., Confalonieri, S., Pelicci, G., Sorkina, T., Sorkin, A., Pelicci, P. G. (1998). Eps15R is a tyrosine kinase substrate with characteristics of a docking protein possibly involved in coated pits-mediated internalization. J. Biol. Chem. 273: 3003–3012.
19. Cook (1991) Medicinal chemistry of antisense oligonucleotides—future opportunities. Anti-Cancer Drug Design 6:585.
20. Corvera, S and Czech, M. P. (1998) "Direct targets of phosphoinositide 3—kinase products in membrane traffic and signal transduction" Trend in Cell Biology 8:442–446.

21. Darnell, J., Lodish, H., Baltimore, D., Berk, A., Zipursky, S. L. and Matsudaira, P. (1995) Cell-to-cell signaling: hormones and receptors. In "Molecular Cell Biology", pp.899–905 Scientific American Books, Inc., New York.
22. D'costa, A. P., Prevette, D. M., Houeonou, L. J., Wang, S., Zackenfels, K., Eohrer, H., Zaph, J., Caroni, P. and Oppenheim, R. W. (1998) Mechanism of insulin like growth factor regulation of programmed cell death of developing avian motomeurons. J. Neurobiol. 36(3):379–394.
23. de Beer, T., Carter, R. E., Lobel-Rice, K. E., Sorkin, A. and Overduin, M. (1998). Structure and Asn-Pro-Phe binding pocket of the Eps15 homology domain. Science 281: 1357–1360.
24. Dealy, C. N. and Kosher, R. A. (1996). IGF1 and insulin in the acquisition of limb-forming ability by the embryonic lateral plate. Dev. Biol. 177: 291–299.
25. Di Battista, J. A., Dore, S., Morin, N., He, Y., Pelletier, J. P. and Martel, P. J. (1997). Prostaglandin E2 stimulates insulin-like growth factor binding protein-4 expression and synthesis in cultured human articular chondrocytes: possible mediation by Ca(++)-calmodulin regulated processes. J Cell Biochem. 65: 408–419.
26. Di Fiore, P. P., Pelicci, P. G. and Sorkin, A. (1997). EH: a novel protein—protein interaction domain potentially involved in intracellular sorting. Trends Biochem Sci. 22: 411–413.
27. Dunn, S. E., Ehrlich, M., Sharp, N. J., Reiss, K., Solomon, G., Hawkins, R., Baserga, R. (1998). "A dominant negative mutant of the insulin-like growth factor-I receptor inhibits the adhesion, invasion, and metastasis of breast cancer". Cancer Res 58: 3353–3361.
28. Ebeling, P. R. (1998). "Osteoporosis in men. New insights into aetiology, pathogenesis, prevention and management " [In Process Citation]. Drugs Aging 13: 421–434.
29. Erickson, J. C., Hollopeter, G. and Palmiter, R. D. (1996). "Attenuation of the obesity syndrome of ob/ob mice by the loss of neuropeptide Y" [see comments]. Science 274: 1704–1707.
30. Fazioli, F., Minichiello, L., Matoskova, B., Wong, W. T. and Di Fiore, P. P. (1993). eps15, a novel tyrosine kinase substrate, exhibits transforming activity. Mol. Cell. Biol. 13: 5814–5828.
31. Floyd, S. and de Camilli, P. (1998). "Endocytosis proteins and cancer: a potential link?" Trends in Cell Biol. 8: 299–301.
32. Fouque, D., Juillard, L., Lasne, Y., Tabakian, A., Laville, M., Joly, M. O. and Laville, M. (1998). "Acute leptin regulation in end-stage renal failure: the role of growth hormone and IGF1 " [see comments]. Kidney Int 54: 932–937.
33. Frade, J. M., Marti, E., Bovolenta, P., Rodriguez, P. M., Perez, G. D., Rohrer, H., Edgar, D. (1996). Insulin-like growth factor-I stimulates neurogenesis in chick retina by regulating expression of the alpha 6 integrin subunit. Development 122: 2497–2506.
34. Green, E. L. (1981) Linkage, recombination and mapping. In "Genetics and Probability in Animal Breeding Experiments", pp.71–113 Macmillan, New York.
35. Groigno, L., Bonnec, G., Wolff, J., Joly, J. and Boujard, D. (1996). Insulin-like growth factor I receptor messenger expression during oogenesis in Xenopus laevis. Endocrinology 137: 3856–3863.
36. Gudkov, A.V., Zelnick, C. R., Kazarov, A. R., Thimmapaya, R., Suttle, D. P., Beck, W. T., and Roninson, I. B. (1993) "Isolation of genetic suppressor elements, including resistance to topoisomerase II interactive cytotoxic drugs, from human topoisomerase II cDNA" Proc. Natl. Acad. Sci. USA 90:3231–3236.
37. Gudkov, A. V. and Robinson I. B. (1997) "Isolation of genetic suppressor elements (GSEs) from random fragment cDNA libraries in retroviral vectors" Methods Mol Biol 69;221–240.
38. Heikhila et al. (1987) A c-myc antisense oligodeoxynucleotide inhibits entry into S phase but not progress from G(0) to G(1). Nature, 328:445.
39. Hill, D. J. and Logan, A. (1992). Peptide growth factors and their interactions during chondrogenesis. Prog. GrowthFactor. Res. 4: 45–68.
40. Iannolo, G., Salcini, A. E., Gaidarov, I., Goodman, O. B., Jr., Baulida, J., Carpenter, G., Pelicci, P. G. (1997). "Mapping of the molecular determinants involved in the interaction between eps15 and AP-2". Cancer Res 57: 240–245.
41. Jakob, U., Scheibel, T., Bose, S., Reinstein, J. and Buchner, J. (1996). Assessment of the ATP binding properties of Hsp90. J Biol. Chem. 271: 10035–10041.
42. Kadowaki, T., Tobe, K., Honda-Yamamoto, H., Kaburagi, Y., Momomura, K., Ueki, K., Takahashi, Y. (1996). "Signal transduction mechanism of insulin and insulin-like growth factor-1". Endcr. J. 43 Suppl: S33–S41.
43. Kirchhausen, T., Bonifacino, J. S. and Riezman, H. (1997). Linking cargo to vesicle formation: receptor tail interactions with coat proteins. Curr. Opin. Cell Biol. 9: 488–495.
44. Kozak, C. A., Peyser, M., Krall, M., Mariano, T. M., Kumar, C. S., Pestka, S. and Mock, B. A. (1990). Molecular genetic markers spanning mouse chromosome 10. Genomics 8: 519–524.
45. Kwitek-Black, A. E., Carmi, R., Duyk, G. M., Buetow, K. H., Elbedour, K., Parvari, R., Yandava, C. N. (1993). Linkage of Bardet-Biedl syndrome to chromosome 16q and evidence for non-allelic genetic heterogeneity. Nat .Genet. 5: 392–396.
46. Leberer, E. Hartner, K. T. Brandl, C. J. et al (1989) "Slow/cardiac sarcoplasmic reticulum Ca2+ -ATPase and phospholamban mRNAs are expressed in chronically stimulated rabbit fast-twitch muscle". Eur J Biochem 185: 51–54.
47. Leberer, E. Timms, B. G. Campbell, K. P. and MacLennan, D. H. (1990) "Purification, calcium binding properties, and ultrastructural localization of the 53,000- and 160,000 (sarcalumenin)-dalton glycoproteins of the sarcoplasmic reticulum". J Biol Chem 265: 10118–10124.
48. Leppert, M., Baird, L., Anderson, K. L., Otterud, B., Lupski, J. R. and Lewis, R. A. (1994). Bardet-Biedl syndrome is linked to DNA markers on chromosome 11q and is genetically heterogeneous. Nat Genet. 7: 108–112.
49. LeRoith, D., Werner, H., Beitner-Johnson, D. and Roberts, T. C., Jr. (1995). "Molecular and Cellular Aspects of the Insulin-Like Growth Factor I Receptor". Endocrine Rev. 16: 143–163.
50. Liu, J. P., Baker, J., Perkins, A. S., Robertson, E. J. and Efstratiadis, A. (1993). Mice carrying null mutations of the genes encoding insulin-like growth factor I (IGF1) and type 1 IGF receptor (IGF1 receptor). Cell 75: 59–72.
51. Lok, F., Owens, J. A., Mundy, L., Robinson, J. S. and Owens, P. C. (1996). Insulin-like growth factor I promotes growth selectively in fetal sheep in late gestation. Am.J-.Physiol. R1148–1155.
52. Lorenzo, P. L., Illera, M. J., Illera, J. C. and Illera, M. (1995). Influence of growth factors on the time-dependent meiotic progression of the bovine oocytes during their in vitro maturation. Rev. Esp. Fisiol. 51: 77-83.

53. Mandel, S., Moreland, E., Nichols, V., Hanna, C. and Lafranchi, S. (1995). "Changes in insulin-like growth factor-I (IGF1), IGF-binding protein-3, growth hormone (GH)-binding protein, erythrocyte IGF1 receptors, and growth rate during GH treatment". J Clin Endocrinol Metab 80: 190–194.
54. Maniatis, T., Fritsch, E. F. and Sambrook, J. (1982). in "Molecular Cloning: A Laboratory Manual" Cold Spring Harbor Laboratory, NY.
55. Mathews, L. S., Hammer, R. E., Behringer, R. R., D'Ercole, A. J., Bell, G. I., Brinster, R. L. and Palmiter, R. D. (1988). Growth enhancement of transgenic mice expressing human insulin-like growth factor I. Endocrinology 123: 2827–2833.
56. Mathews, L. S., Hammer, R. E., Brinster, R. L. and Palmiter, R. D. (1988). Expression of insulin-like growth factor I in transgenic mice with elevated levels of growth hormone is correlated with growth. Endocrinology 123: 433–437.
57. Matise, M. P. and Joyner, A. L. (1997). Expression patterns of developmental control genes in normal and Engrailed-1 mutant mouse spinal cord reveal early diversity in developing interneurons. J Neurosci. 17: 7805–7816.
58. Mukherjee, S., Ghosh, R. N. and Maxfield, F. R. (1997). Endocytosis. Physiol. Rev. 77: 759–803.
59. Navarro, P., Valverde, A. M., Benito, M. and Lorenzo, M. (1998). Insulin/IGF1 rescues immortalized brown adipocytes from apoptosis down-regulating Bcl-xS expression, in a PI 3-kinase- and map kinase-dependent manner. Exp Cell Res 243: 213–221.
60. Paoluzi, S., Castagnoli, L., Lauro, I., Salcini, A. E., Coda, L., Fre, S., Confalonieri, S., Pellici, P. G., Di Fiore, P. P., and Cesareni, G., (1998) "Recognition specificity of individual EH domains of mammals and yeast" EMBO J. 17:6542–6550.
61. Parisot, J. P., Hu, X. F., DeLuise, M. and Zalcberg, J. R. (1999). "Altered expression of the IGF1 receptor in a tamoxifen-resistant human breast cancer cell line" [In Process Citation]. Br J Cancer 79: 693–700.
62. Pasmanik-Chor, M., Madar-Shapiro, L., Stein, E. O., Aerts, H., Gatt, S. and Horowitz, M. (1997). Expression of mutated glucocerebrosidase alleles in human cells. Hum.Mol.Genet. 6: 887–895.
63. Pestov A G, Polonskaia M and Lester F L (1999) "Flow Cytometric Analysis of the cell cycle in transfected cells without cell fixation" Bio Techniques 26:102–106.
64. Poiraudeau, S., Lieberherr, M., Kergosie, N. and Corvol, M. T. (1997). Different mechanisms are involved in intracellular calcium increase by insulin-like growth factors 1 and 2 in articular chondrocytes: voltage-gated calcium channels, and/or phospholipase C coupled to a pertussis-sensitive G-protein. J.Cell. Biochem. 64: 414–422.
65. Radetti, G., Bozzola, M., Pasquino, B., Paganini, C., Aglialoro, A., Livieri, C. and Barreca, A. (1998). "Growth hormone bioactivity, insulin-like growth factors (IGFs), and IGF binding proteins in obese children". Metabolism 47: 1490–1493.
66. Reed et al. (1990) Antisense mediated inhibition of BCL2 prooncogene expression and leukemic cell growth and survival: comparison of phosphodiester and phosphorothioate oligodeoxynucleotides. Cancer Res. 50:6565.
67. Roos, J. and Kelly, R. B. (1998). Dap160, a neural-specific Eps15 homology and multiple SH3 domain-containing protein that interacts with Drosophila dynamin. J. Biol. Chem. 273:19108–19119.
68. Sandhoff, K. Harzer, K. and Furst, W. (1995) Sphingolipid activator proteins. In "The Metabolic and Molecular Basis of Inherited Disease" (S.Scriber, A.Beaudet, W.Sly, D.Valle, Eds.), pp.2427–2441 McGrew Hill.
69. Sanger, F. (1981). Determination of nucleotide sequences in DNA. Science 214: 1205–1210.
70. Sengar, A. S., Wang, W., Bishay, J., Cohen, S. and Egan., S. E. (1999). "The EH and SH3 domain Ese proteins regulate endocytosis by linking to dynamin and Eps15". Embo J 18: 1159–1171.
71. Schumacher, C., Knudsen, B. S., Ohuchi, T., Di Fiore, P. P., Glassman, R. H. and Hanafasa, H. (1995). The SH3 domain of Crk binds specifically to a conserved proline-rich motif in Eps15 and Eps15R. J Biol Chem. 270: 15341–15347.
72. Sheffield, V. C., Carmi, R., Kwitek, B. A., Rokhlina, T., Nishimura, D., Duyk, G. M., Elbedour, K. (1994). Identification of a Bardet-Biedl syndrome locus on chromosome 3 and evaluation of an efficient approach to homozygositymapping. Hum. Mol.Genet. 3:1331–1335.
73. Skehel J. J., and Wiley, C., (1998) "Coiled coils in both intracellular vesicle and viral membrane fusion" Cell 95:871–874.
74. Sorkina, T., Bild, A., Tebar, F. and Sorkin, A. (1999). Clathrin, adaptors and eps15 in endosomes containing activated epidermal growth factor receptors. J Cell Sci 112:317–327.
75. Strohm, O., Osterziel, K. J. and Dietz, R. (1998). Insulin-like growth factor-I and risk of breast cancer [letter]. Lancet 352: 489.
76. Sweet, H. O. and Bronson, R. T. (1991). Osteochondrodystrophy (ocd): a new autosomal recessive mutation in the mouse. J Hered. 82: 140–144.
77. Szczylik et al (1991) Selective inhibition of leukemia cell proliferation by BCR-ABL antisense oligodeoxynucleotides. Science 253:562.
78. Tajima, Y., Watanabe, D., Koshimizu, U., Matsuzawa, T. and Nishimune, Y. (1995). Insulin-like growth factor-I and transforming growth factor-alpha stimulate differentiation of type A spermatogonia in organ culture of adult mouse cryptorchid testes. Int.J. Androl. 18: 8–12.
79. Takai, S., Kozak, C. A., Kitamura, K. and Takeda, A. (1996). Assignment of the CD45-AP gene to the centromeric end of mouse chromosome 19 and human chromosome 11q13.1–q13.3. Genomics 38: 429–431.
80. Tardif, G., Reboul, P., Pelletier, J. P., Geng, C., Cloutier, J. M. and Martel, P. J. (1996). Normal expression of type 1 insulin-like growth factor receptor by human osteoarthritic chondrocytes with increased expression and synthesis of i nsulin-like growth factor binding proteins. Arthritis Rheum. 39: 968–978.
81. Tebar, F., Confalonieri, S., Carter, R. E., Di, F. P. and Sorkin, A. (1997). Eps15 is constitutively oligomerized due to homophilic interaction of its coiled-coil region. J.Biol.Chem. 272: 15413–15418.
82. Thomas, P. S. (1980). Hybridization of denatured RNA and small DNA fragments transferred to nitrocellulose. Proc. Natl. Acad. Sci. USA 77: 5201–5205.
83. Villalpando, F. I., Villafan, M. H. and Pacheco, P. (1996). Delayed expression of the insulin-like growth factor I (IGF1) gene in the XY sex-reversed female mouse ovary. Int.J.Dev Biol. 40: 477–482.
84. Wang, L., Ma, W., Markovich, R., Chen, J. W. and Wang, P. H. (1998). "Regulation of cardiomyocyte apoptotic signaling by insulin-like growth factor I". Circ Res 83: 516–522.

85. Warren, R. A., Green, F. A., Stenberg, P. E. and Enns, C. A. (1998). Distinct saturable pathways for the endocytosis of different tyrosine motifs. J. Biol.Che. 273: 17056–17063.
86. Welch P. J., Barber J. R., and Wong-Staal F. (1998) Expression of ribozymes in gene transfer systems to modulate target RNA levels. Curr. Opin. Biotechnol., 9(5):486–496.rrr
87. Wendland, B. and Emr, S. D. (1998). Pan1p, yeast eps15, functions as a multivalent adaptor that coordinates protein—protein interactions essential for endocytosis. J.Cell.Biol. 141: 71–84.
88. Werner, H. (1998). "Dysregulation of the type 1 IGF receptor as a paradigm in tumor progression". Mol Cell Endocrinol 141: 1–5.
89. Yamabhai, M., Hoffman, N. G., Hardison, N. L., McPherson, P. S., Castagnoli, L., Cesareni, G. Kay, B. K. (1998). "Intersectin, a Novel Adaptor Protein with Two Eps15 Homology and Five Src Homology 3 Domains". J Biol Chem 273: 31401–31407.
90. Yamamura, T., Hitomi, J., Nagasaki, K., Suzuki, M., Takahashi, E., Saito, S., Tsukada, T. (1996). Human CAAF1 gene—molecular cloning, gene structure, and chromosome mapping. Biochem.Biophys.Res Commun. 221: 356–360.
91. Yaron, A., Hatzubai, A., Davis, M., Lavon, I., Amit, S., Manning, A. M., Andersen, J. S. (1998). "Identification of the receptor component of the IkappaB alpha-ubiquitin ligase". Nature 396: 590–594.
92. Yoshimura, Y., Nagamatsu, S., Ando, M., Iwashita, M., Oda, T., Katsumata, Y., Shiokawa, S. (1996). "Insulin-like growth factor binding protein-3 inhibits gonadotropin-induced ovulation, oocyte maturation, and steroidogenesis in rabbit ovary". Endocrinology 137: 438–446.
93. Yoshinaga, K. (1994). "Morphological Studies on Germ Cell Development and Differentiation in Mammals". Med. Electron Microsc. 27: 251–253.
94. Young, T-L.Penny, L. Woods, M. O. et al (1998) A fifth locus for Bardet-Biedl syndrome maps to chromosome 2q31. Am. J. Hum. Genet. 63 (suppl.): A317.
95. Zachow, R. J. and Magoffin, D. A. (1997). "Direct intraovarian effects of leptin: impairment of the synergistic action of insulin-like growth factor-I on follicle-stimulating hormone-dependent estradiol-17 beta production by rat ovarian granulosa cells". Endocrinology 138: 847–850.

What is claimed is:

1. An isolated nucleic acid comprising a genomic, complementary or composite polynucleotide sequence encoding a polypeptide being functional in endocytosis in cells and being at least 80% homologous to SEQ ID NOs:4 or 5 as determined using the BestFit software of the Wisconsin sequence analysis package, utilizing the Smith and Waterman algorithm, where gap creation penalty equals 8 and gap extension penalty equals 2.

2. The isolated nucleic acid of claim 1, wherein said polypeptide is capable of increasing endocytic sequestration of IGF-1R when overexpressed in cells displaying said IGF-1R.

3. An isolated nucleic acid comprising a polynucleotide sequence as set forth in SEQ ID NOs: 1 or 2.

4. An isolated nucleic acid comprising a polynucleotide sequence encoding a polypeptide as set forth in SEQ ID NOs:4 or 5.

* * * * *

SEQUENCE LISTING (1) GENERAL INFORMATION:

(iii) NUMBER OF SEQUENCES:27

(2) INFORMATION FOR SEQ ID NO:1:

(i) SEQUENCE CHARACTERISTICS:
        (A) LENGTH:3508
        (B) TYPE:nucleic acid
        (C) STRANDEDNESS:double
        (D) TOPOLOGY:linear (xi) SEQUENCE DESCRIPTION: SEQ ID NO:1:

```
CCCAATTCCG  CCCTGCCCCC  GCCGCGGCGG  CGCTAGCCGC  CACTGAGGGA           50

CCGACCCTAT  AAAGGCCGCT  CCGCGAGGGG  TGCGCAGCAT  TCGGCAGAGG          100

GCGCCTTCGA  CGGGCTGGGC  TGTGCGCCTG  CGCAGTGTGG  GTCGCTCCCG          150

ATTCCCTGCC  CCGGCCGGCC  CCGCCTCGGC  TCCGCACCCT  CGCCCCGCTC          200

TCAGCCGCCG  CTCTGCCCCG  CAGCAGCCAG  CCCCGTGTCC  GGCAGTATGT          250

TCAGCTGGGT  CAGCAAGGAT  GCCCGCCGCA  AGAAGGAGCC  GGAGCTCTTC          300

CAGACGGTGG  CTGAGGGGCT  GCGGCAGCTG  TACGCGCAGA  AGCTGCTACC          350

CCTGGAGGAG  CACTACCGCT  TCCACGAGTT  CCACTCGCCC  GCGCTGGAGG          400

ACGCTGACTT  CGACAACAAG  CCTATGGTGC  TCCTCGTGGG  GCAGTACAGC          450

ACGGGCAAGA  CCACCTTCAT  CCGACACCTG  ATCGAGCAGG  ACTTCCCGGG          500

GATGCGCATC  GGGCCCGAGC  CCACCACCGA  CTCCTTCATC  GCCGTCATGC          550

ACGGCCCCAC  TGAGGGCGTG  GTGCCGGGCA  ACGCGCTCGT  GGTGGACCCG          600

CGGCGCCCCT  TCCGCAAGCT  CAACCGGTTT  GGCAACGCTT  TCCTCAACAG          650

GTTCATGTGT  GCCCAGCTGC  CCAACCCCGT  CCTGGACAGC  ATCAGCATCA          700

TCGACACCCC  CGGGATCCTG  TCTGGAGAGA  AGCAGCGGAT  CAGCAGAGGC          750

TATGACTTTG  CAGCCGTCCT  GGAGTGGTTC  GCGGATTGTT  GGGACCGCAT          800
```

-continued

| | |
|---|---|
| CATCCTGCTC TTCGACGCCC ACAAGCAGGA CATCTCCCAT GAGTTCTCGG | 850 |
| AAGTGATCAA GGCTCTGAAG AACCATGAGG ACAAGATCCG CATGGTGCTG | 900 |
| AACAAGGCAG ACCAGATCGA GACGCAGCAG CTGATGCGGG TGTACGGGGC | 950 |
| CCTCATGTGG TCCCTGGGCA AGATCATCAA CACCCCCGAG GTGGTCAGGG | 1000 |
| TCTACATCGG CTCCTTCTGG TCCCACCCGC TCCTCATCCC CGACAACCGC | 1050 |
| AAGCTCTTTG AGGCCGAGGA GCAGGACCTC TTCAAGGACA TCCAGTCACT | 1100 |
| GCCCCGAAAC GCCGCCCTCA GGAAGCTCAA TGACCTGATC AAGCGGGCAC | 1150 |
| GGCTGGCCAA GGTTCACGCC TACATCATCA GCTCCCTCAA GAAAGAGATG | 1200 |
| CCCAATGTCT TTGGTAAAGA GAGCAAAAAG AAAGAGCTGG TGAACAACCT | 1250 |
| GGGAGAGATC TACCAGAAGA TTGAGCGCGA GCACCAGATC TCCCCTGGGG | 1300 |
| ACTTCCCGAG CCTCCGCAAG ATGCAGGAAC TCCTGCAGAC CCAGGACTTC | 1350 |
| AGCAAGTTCC AGGCGCTGAA GCCCAAGCTG CTGGACACGG TGGATGACAT | 1400 |
| GCTGGCCAAC GACATCGCGC GGCTGATGGT GATGGTGCGG CAGGAGGAGT | 1450 |
| CCCTGATGCC TTCCCAGGTG GTCAAGGGCG GCGCCTTTGA CGGCACCATG | 1500 |
| AACGGGCCGT TCGGGCACGG CTACGGCGAG GGGGCCGGCG AGGGCATCGA | 1550 |
| CGACGTGGAG TGGGTGGTGG GCAAGGACAA GCCCTCCTAC GACGAGATCT | 1600 |
| TCTACACGCT GTCCCCTGTC AACGGTAAGA TTACGGGTGC CAATGTTAAG | 1650 |
| AAGGAGATGG TGAAGTCCAA GCTCCCCAAC ACCGAGCTAG GGAAGATCTG | 1700 |
| GAAGCTGGCC GACGTGGACA AGGACGGGCT GCTGGACGAC GAGGAGTTCG | 1750 |
| CGCTGGCCAA CCACCTCATC AAGGTCAAGC TGGAGGGCCA CGAGCTGCCC | 1800 |
| GCCGACCTGC CCCCGCACCT GGTGCCGCCC TCCAAGCGCA GACATGAGTG | 1850 |
| ATGGCGCCCG GCCCCGCACC TGCCATTTGC ACGCCCGGCC GGGAGGCAGA | 1900 |
| GACGGGGGGA GGGGAAGCCT CACCATTTCT CAAGGTCCAT AAAGACTGAG | 1950 |
| CGGATGTTTC CTCGCCTCTC GAAAAGGAAA ACCACCATCT TTCTTTTAAG | 2000 |
| GCTGTTCCTG GGCCTGGCGG GGGAGGCAGG GGTGAGAGGA TGGAATTGTG | 2050 |
| TGCACAAGAA CTGTGGCTAT TTTAATATAA CGTTAGAGGC TGCGTTCTTT | 2100 |
| GTCGCCGCCT CCCCTGTGTG CCAGCCCTGT GTGCACGGCC TCTGCCCCCC | 2150 |
| GGCCTTTGCT GTGGCTGGAG CTGGACAGTG CAGCGACTGC GACCGTGGGG | 2200 |
| GAGCCAGGTC GCCCTTTTGG CAGCTGCTAG GCTGAGGCTG CATGGACAGG | 2250 |
| AACACCAGGC ACCCTCCGTG TGCTTCTGAG CTGAGGTTGC TTCACGGGAC | 2300 |
| CGTGGCTTCC TTCCTCACCT GGCTCTGCCT CCCCCGTGCT CTCGGGCGAA | 2350 |
| GTGGGTTCTT GTGCCTTCCC CTCCCGGGCC CAGGCTCCCC GTGCGCGGGC | 2400 |
| CCTGCCCTTT CCTCCCGCGC CCCACCGGCT CCGACGCGCA ACCCCGCTCA | 2450 |
| GCAGTCACAG AAGCAGGGCC CAGCCACCTT GGTCTTTTTT TGGGAGTTCA | 2500 |
| GGGGAGTAGG AGAATGTCTT CCAGAAAAAT ACATAAGCTA GTTTCTGTTC | 2550 |
| TGTAAAGTGA TATCTTTCAT ACTTGACCAA AGTTCCCAAT AACTTCCCAA | 2600 |
| CCACTGTTCA AAACTGTGAA TTTTTGTCTC CCCTTCCCAC CCTCCAACCA | 2650 |
| AGGAACAACC CTGCCCAGGG GGNTAATTAA GGAGTGGNAT AACGNGGGGG | 2700 |
| GATTNACNCC CTTTANCCGG AACNNGANGG CTTGTAATTT TCCTGAATTG | 2750 |

| | |
|---|---|
| ATGGAANGNT TTNTTCAATT CNCCAGCTTC GTTNCCANAA ACCNTATTAA | 2800 |
| NTTANAGTGA GAGCTCTNGG GGAACCCNAC CCTCCGAACN TTTGGGGGAG | 2850 |
| GGTTGGTCGG NGCNNTTGGC AACCCGGCGG GGGCCCTAAA CGGACAAGCC | 2900 |
| CCAGTGATGG GCAAAGAATA TGCCAGAGGT CCTNGATACC TTTTAAGCCC | 2950 |
| AAGACAAGGG GGAGCAGGGA CAAAACCAGC CCAATATGTA ATCCCCTCTC | 3000 |
| ATTTCCTACC TTCCTTCCTC CTCTGTTTAG CAAAGGAGGG CAGCTCACTT | 3050 |
| GGATGTCCTT ACAACGCCCC TGGCCCCCAG GTTGAGCAAT AAGAAACCAG | 3100 |
| AACCTTGCGC CCAGTGGCCC GGGCCAGTTC AGGCCGCCTC CCCCTCCTCT | 3150 |
| GCCTGGGGCC ATTGAGCCCA GCCTCCAGGG CCCGGGCGCG TTTGCAGCCA | 3200 |
| GTGGCCACTG TCCGGGCTGT GATGGCACCA AGGCAGGTGG AGCACCAGGT | 3250 |
| ACCACACAGC TGGGCTTCCC ACCAGGCTTT CCCGCGGGGG TCTCAGGGAG | 3300 |
| TTCTCCCCAG CGCTGCTTGC TCGGAGTCTG CAGGAACTGG CCTTGTTCTC | 3350 |
| CTAGCCCGTC ACTCCATACA GTATTAGGTG AGGATGGATG CGGGCGCTGT | 3400 |
| CCTTGCCGGG AAGTCACTGT TTGAAGTTGC AGTGGCTTGT TCACACCTGT | 3450 |
| GGAAGAGAAG TGAAGACTTT CTCCTTGCAT TAAAAAGTCT GAACTGTGAA | 3500 |
| AAAAAAAA | 3508 |

(2) INFORMATION FOR SEQ ID NO:2:

(i) SEQUENCE CHARACTERISTICS:
        (A) LENGTH:3348
        (B) TYPE:nucleic acid
        (C) STRANDEDNESS:double
        (D) TOPOLOGY:linear (xi) SEQUENCE DESCRIPTION: SEQ ID NO:2:

| | |
|---|---|
| ATTCGGCACG GGGTCGGCCG CGCGCCCCAG TCCCGCTCAG CCACCGCTCC | 50 |
| GTCCTGTAGC AGCCAGCCCC GTCTCCGGCA TCATGTTCAG CTGGGTGAGC | 100 |
| AAGGATGCCC GCCGCAAGAA GGAGCCGGAG CTCTTCCAGA CGGTGGCCGA | 150 |
| GGGGCTGCGG CACGTGTACG CGCAGAAGCT GCTGCCGCTG GAGGAGCACT | 200 |
| ATCGCTTCCA CGAGTTCCAC TCGCCCGCGC TGGAGGACGC TGACTTCGAC | 250 |
| AACAAGCCGA TGGTGCTCCT GGTCGGCCAG TACAGCACCG GCAAGACCAC | 300 |
| CTTCATCCGC CACCTGATCG AGCAGGACTT CCCGGGGATG CGCATCGGGC | 350 |
| CGGAGCCCAC CACCGACTCC TTCATCGCGG TCATGCACGG CCCCACCGAG | 400 |
| GGCGTGGTGC CCGGCAACGC GCTCGTCGTG GACCCGCGGC GCCCCTTCCG | 450 |
| CAAGCTCAAC GCCTTCGGCA ACGCCTTCCT CAACAGGTTC ATGTGTGCAC | 500 |
| AGCTGCCCAA CCCAGTACTG GACAGCATCA GCATCATTGA CACTCCTGGG | 550 |
| ATCCTGTCTG GGGAGAAGCA GCGCATCAGC CGAGGTTATG ACTTTGCGGC | 600 |
| TGTCCTTGAG TGGTTCGCAG AGCGTGTGGA CCGCATCATC TTGTTGTTCG | 650 |
| ACGCCCACAA GCTGGACATC TCAGACGAGT TCTCAGAAGT CATCAAGGCC | 700 |
| CTCAAAAATC ACGAGGACAA GATCCGTGTG GTGCTGAACA AGGCTGATCA | 750 |
| GATCGAGACG CAGCAGCTGA TGCGAGTATA CGGGGCCCTC ATGTGGTCCC | 800 |
| TGGGGAAGAT CATCAACACC CCCGAGGTGG TCAGAGTCTA CATCGGCTCC | 850 |
| TTCTGGTCAC ACCCACTGCT CATCCCTGAC AACCGGAAGT TCTTTGAGGC | 900 |

-continued

```
GGAGGAGCAG GACTTTTTCA AAGACATCCA GTTTCTGCCG AGAAACGCCG        950

CCCTCAGGAA GTTCAATGAC CTCATCAAGC GGGCCAGGCT GGCCAAGGTC       1000

CATGCCTACA TCATCAGTTC CCTCAAGAAG GAGATGCCCA ATGTTTTCGG       1050

GAAAGAGAGC AAGAAGAAAG AGCTGGTGAA CAACCTGGGA GAGATCTACC       1100

AGAAGATCGA GCGGGAGCAC CAGATCTCCT CCGGCGACTT CCCAAGCCTG       1150

CGTAAGATGC AGGAACTCCT GCAGACCCAG GACTTCAGCA AGTTCCAGGC       1200

CTTGAAGCCC AAGCTGCTGG ATACAGTGGA TGATATGCTG GCCAACGATA       1250

TAGCTCGGCT GATGGTGATG GTGCGCCAGG AGGAGTCCCT GATGCCCTCA       1300

CAGGCTGTGA AGGGTGGTGC TTTTGATGGC ACCATGAATG GGCCCTTTGG       1350

GCATGGCTAC GGCGAGGGGG CTGGCGAGGG CATTGATGAT GTTGAGTGGG       1400

TAGTTGGCAA GGACAAGCCC ACCTATGATG AGATCTTCTA CACACTGTCT       1450

CCTGTCAACG GCAAGATCAC AGGTGCTAAT GCCAAGAAGG AGATGGTGAA       1500

GTCCAAGCTG CCCAACACAG TGCTGGGAA GATCTGGAAG TTGGCAGATG        1550

TGGACAAGGA TGGCCTGCTG GATGACGAGG AGTTTGCCCT GGCCAACCAC       1600

CTTATCAAGG TGAAGCTAGA GGGCCACGAG CTGCCCGCTG ACCTTCCTCC       1650

ACATCTCATT CCACCCTCCA AACGGAGGCA CGAGTGACTT CCATGCCTGA       1700

GATACCTACA ACCCCAGGGC TGCTGCCACT TTCTACCCAC AGCTCCTTGT       1750

CTGCCCAGGT GGCTGGGGCT GGAGGGGCAG AAATTGGGGG AGGGAAAGGG       1800

TCACCATTTT TCAAGGTCCA TAAAGACCTG ACGGTGTTTC CTCAGCTCTT       1850

GAATAGGAAA ACACCATCTT TCTTTTAAAG CTGTTCCGGG GTTCAGCGGG       1900

AGGCATGGGT GATGCTTGGA TATGAACAGT GGGATTTTGT GCACAGGAAC       1950

CATGATATTT TTAATATATA ACATTAGAGG CAGCTGCTGG TTTGCATCTC       2000

TTGTCTGACA GCCCNAGGAT TGTTCTGGGC CCTGCTGAGG GTGATGCNAA       2050

CCTTCTTGTT ACCCTTTCTT AGCCCTCATC TTTGGCTGAG GTAGAAGATG       2100

TATCCTACGT GAGAGGAGTG CCGATGAAGA TTGTCCTGAT TAAGAGTTAA       2150

TTGTCAAAAA AAAAAAAAAC TGCGCGGACG TATCCTTAGT GAGGTATTAC       2200

GTGCTGCCGT GTTAAACGGT ATGGACCTGG GTCGAATAAT GTTTGGACTC       2250

TTTCGGAGTG ATAGAAAACT CGCGATCGCC AAAATCCGGT GAATTGGAGT       2300

GGCCCCTTAT GCGATGCGGG TGTTTCGAGG TTCATGTTGC GGTTGTGGTT       2350

TGTGGTGCGT GTTGTGTTAT TGTGGGTGTG TTTAGGTGCG CATCTAGTTC       2400

ACAATGATGT CGTGACTTTT GCGTTATTTA ACACATTGTT GTGTGGTAAA       2450

AAACAGTCCA TGAACGTCTA GGAAAATGCA TAAGCTACTT AGTGTTCTGT       2500

AGTGACACTT GATACTTGAC CAAGACTTTG AGTAACTTAC ATCACTTCGT       2550

TCAAAACTGT GATTTTGTC TCCTCTTTCC TATACTCCAC CGTTGGACGA        2600

TTTCCACCCC CAGAGCCTCG ATAGAGCTGA CATCCTAGGG CTTGAGTTTG       2650

CTTTCTGGCT GAGGGGAGGT CATCCCAGCT TCTGCTCAGA GGGTCTGAAA       2700

TGTAGCCCCC CACCCCCGCC CCAAGGTCAA CCTTTATGGT AGCTTTCCTG       2750

GAGCCCCTCT CTGCCTTGGA CAGGCAGTAG GCCCCTGTGA CCTGGGGTGG       2800

TCTGGGGCTG GTAAGAGGAA GCCTGTGGCT CTGGCCTGGG TGTAGTGTCC       2850

ATGCAGGACG ACAGGGGAAA ACCCAGCCCC TTCCCTCGCC CTGTCATTTC       2900
```

| | |
|---|---:|
| CTTCCTCTCC TCCTCTGCTG AGCCAAGGAG GTCTGGGTGT CCTGAGAGCC | 2950 |
| CCAGACTGAG CAGTAAGAAG CCTGAGCTAG CAAATGACCA CTTTAGTCAC | 3000 |
| CCCACTGTAG CCTGGGGACC CGGACACATC CTGTGGCCAG TGGTTTGGCT | 3050 |
| GTCAGGGTGG GCTTTCCACT GAGCTGGGTA GGGCATTGCA GCCTGCTCCT | 3100 |
| CTGACACTGT AGGTGGGCTT CAGGGAGCTG GCCTGCCAAC CCCCCAGCAC | 3150 |
| TGTTCTGGGC CCTCGTGAGG GTGAGCTCCA GCCTGGCCTG TTACCTCCCT | 3200 |
| GCCTCAGCCC TCCACTCCTT GGCTGAGGGT GAGAGAGATG TCATCCTCAG | 3250 |
| CTGTAGAGGG AGTGGCCCCC GAATGAAGAC TGGTTCTCGC ATTAAAGGAA | 3300 |
| GTTTAATTGT GCCAAAGCCA AAAAAAAAAA AAAAAAAAAA AAAAAAA | 3348 |

(2) INFORMATION FOR SEQ ID NO:3:

(i) SEQUENCE CHARACTERISTICS:
        (A) LENGTH:14707
        (B) TYPE:nucleic acid
        (C) STRANDEDNESS:double
        (D) TOPOLOGY:linear (xi) SEQUENCE DESCRIPTION: SEQ ID NO:3:

| | |
|---|---:|
| GNTCNACTCN ATCTTTTGGG AGAACAGCTG GTCCTCTCCA CTGCTGAGCC | 50 |
| ATCTCTCCAA CCCCGAGTTT TCATTTTTTA TGACAGGATC GTCTCTGGAT | 100 |
| GGCATCAGCT TGCCGTGGAC TAAGTGCTAG AACTGTAGGG TGTGCGCCAC | 150 |
| CACGTCTGTC TTATGTTTGC AGTTTTGTTT TTAAAGGCAG AATATCAGCC | 200 |
| CTGTGTGTGG CCACAGGCCT TTAATCCCAG GACTCAGGAG ACAGAGGCTG | 250 |
| GAGGACCTCT GTGCTCAAGG CCAGCCTGGT CTACATAGTG AATTCCAGGA | 300 |
| CAGCCACATA GTGAGACCCT GTCTTAGAAA CAAACAGGAT ATCATACAGC | 350 |
| CTGTGCTGGC CCTAACTTCT TATTTCTCCA CTGATGACCT TGAATGCCTG | 400 |
| ATTCTTCTGC CTCTACTTTT CAAGTGCTGG GACTAGAAAT ACACATTATC | 450 |
| ATACTTGAAT TTCCTTTATT TTCTAATTTT GGAGAAATGT ACCTACTATA | 500 |
| TAAGCTGTAC CGTTTCCCAC CGTTGGAGAG CAGTGGGGTT TGGTGCCGCT | 550 |
| GCACTGCTGT GAGCCATCAC ACTGTTCCAT TTTCCCAAAA CCTTTCAGTC | 600 |
| AGCACTGCCA CCTTGCCTTC CACCCTGGCC CTGGCCCCAG TGTCTTCTCT | 650 |
| GCATCGCCCC CTGGCTTCCT CATAGGTGGG CCTGGCTGCT GGGGCTTGTC | 700 |
| ATACAGTTGT TCACATGGCC ACTCCTTCCT TATCTGAGAT GTCTCTGGTC | 750 |
| CCCACTGAAG TCCCTCCCCC TGCAGGTGGG CTTCTCCGTC TCGTCTATCC | 800 |
| TCTCAAGCTG TGTGCTCTGT ATCCTTGGTG GAAACTGGTG TCCGCTCTCT | 850 |
| CTAGCCAGAC GGTGGTGCAG GGTGCCCCTG TTAGATACTC TTTCCCTCTG | 900 |
| TGTGTGCACA CAGCTACCTT TATGTTGTTG TGTGGGTGGG ACGGACACGC | 950 |
| ACCCTGCGGC CTGCTGTTTT GCCANCTCTG TCACCAGCTT GAACTCCTCA | 1000 |
| CCGAGAGCCG GGAGTCTGCT TTTGTGACTG CGTGGCTCTC CTGGGCTCCA | 1050 |
| TGTCCATTGC CACCCTTTGG CGTCCAGGGC TCCTGGAAAC CAGTGTCCTC | 1100 |
| TCTCTAAATC CACATAAGAC ACCTGAGTGT AATGAGGGAC AATCGGTTCA | 1150 |
| ATAGTGCCAG ATGGGCCTGC GGGTGGCCTA CAGTCATAGA GTCACATGCC | 1200 |
| TGTGTCAACA TGGCTGCAGT CCTTTGGGTA ATCAGTGATG TGTTTGGTCA | 1250 |

```
CCCAGAGTGC TCTCTTTTCA CCCAAAGCGT GTTTCCCACC AGAGGGAAAA      1300

GGTTTGGGGC CATAGTCGGT CGGGCTTGGA AGGTGACCTC AGAAAAATCA      1350

AGCATGGTAG CTCTTATCTG CAATCCCGCC CCTCAGGAGG CAGAGGCAGG      1400

AGAATTGCCA CCATTTGAAG CCTGCTTGGA ATATGGAGTA ATAGCCTGTC      1450

TTTTTTTTTT TTTTTTTTTT TTTTAAAGAT TTATTTATTA TTATATGTAA      1500

GTACACTGTA GCTGTCTTCA GACACACCAG AAGAGGGAGT CAGATCTTGT      1550

TACGGATGGT TGTGAGCCAC CATGTGGTTG CTGGGATTTG AACTCTGGAC      1600

CTTCGGAAGA GCAGTCGGGT GCTCTTACCC ACTGAGCCAT CTCACCAGCC      1650

CAAGCCTGTC TTAAACTCCA AAATAATTA ACCGGGAAGG TCCCTTCACC       1700

GCCTGAGAAA GAAGAAGAGA CTTAATGAAG CTGAACATGA TGGCTCATGC      1750

TTTTAATTCC TGTATTTGAG AGGCAGAGGC AGGTGAATCT CTGAATTTGA      1800

TGCCAGCCTG GTCTCCTAGT GAGTTCCAGG CCAGCCAGGG CTACACAGTG      1850

AGACTNTGTC CCCTAGAAAA AGGAAAAGCA AACCCAACCC AGCTAACTGC      1900

AGTGCTGCGG AGAACCAGGC GGGCGGGCGG GAGGGCCAGG GGAAGGGCCT      1950

CCTCCCATCG CTCTCATTCA GTGTTCCCTT CCCCCACCAG AGGGGAAAGG      2000

ATTGGGGCCA TAGTGCTCAG GGCTTGGGAA GGTGACCTCA GCTTCCCTGC      2050

TGAAGGCCTG ACTGCCTAGC CAAAGCCAAC AGGACTGGTG GTGCTTGGCC      2100

TGGAGTTTCC CTGTTCGCAG GAACTGGGGT TTGGCCTCGC TGCTGCCCCT      2150

GCTGTGTGAG GTAGCTTCAG CTTTGGATGG GGCCAAATGG GCTGAGTGGG      2200

AAGGAGCAGA GCCTCTCTTT GGTGAGCAGG AGTGTCAGTT CCTGAGTCAG      2250

CACTTCTTCA GCAGTGCTGT GTTCCTAGAA CTCACGTACA AGGAAGGCCT      2300

CAGGGCCCCG GACAGGCTCT GGGCTCAGCT GGGGTACAGC TCAGAGCCCT      2350

GGGCAGCAGC TGCCTCTCCT GGCCTCTGCT TCCCGCTATG CTGCTGCTCT      2400

AGACCTTCCC TTCTGGTTTT CTGCTGACAG CTCACTCCTC CGGTGTCCAC      2450

TCCCTGCTCC CAGCCAGCTG CAGGGAGCAA GGAGGGCCTT GTACTTTGGA      2500

ACTGGCTGGC TGCTGAAATG CAGTGTGACC TGGCCCTCCC TGTGCACTTG      2550

ATACCTGAAG CTCTGACACT GAACCAGCCG CACACCGACT GCAGCTCAGT      2600

GTACCTCCGC CTTCAAGGTA GCCTCAATTG GCTGACTAAT GTGCCCCCAA      2650

GTTCCTGTGT GTCAAGAATG TAGAGGTCAG AAGACAACCT TGTAGAGAAG      2700

GGTTCTCTCT CCACCTTCAC ATGGGTCCCA AAGATCAAAT TCACTGCCAG      2750

GCTCGTATGG AAAGCACCCA GATCAGCTGA GCCATCTCAT TGGCTTTGTT      2800

CTTCTTAATT GTTTCCTGGT ATTGCCTGGA ATTGAACCCA GAACTTTGTT      2850

TTTGCTTGGC CTGTCTAGCC TAGCACCTTC GAAGTGCCAC CACCCCAGCT      2900

TTATACACAG GGTGGGGGAA CATTGAGTGG TACCCCCCCT AGCTGTACAG      2950

TGCAGCATCA GCAGGCCTTG ATGAACGGGG TGGTGGGGAA TCCTGTGCCA      3000

GCATGTGTAG TCCTGGACAC TGTCCTTTCC TCGGGACTTC CCCCTACAGT      3050

CAGTCTGTCT GTCTGTCTGT CTGTCTGTCT GTCTGTCTCC TGCATCTGAA      3100

GATTGCACGT CAGCCCTCCT GAGGTTGGGC TTGGAGTAGT TTTCCCAGTG      3150

CTAGAGCGGT TTGTGAGGCA AGAGTTTGGC TGGACCAGCC TGTTCCAGAC      3200
```

```
TGTCTTCTCT CTGAGTTGCT TCCCTGGCTC ATCTTTTGGG GTCTTGGCAA        3250

CTTTCTGGGA AGTACTAAGT GGTTCTCAGA GGGCTGGCCT ACATTTGGGG        3300

TGACCTGGAA CCTGTGAACA TTCAGTAAGT GACAGGAAAC TTAGTCCAGG        3350

CAAAGAGAAG GACAGTGTTC AGATTCCGCG GAGAGGTCAG GCTGTCATGA        3400

GGCTCTGCGC AGCTGTTTCC AGTCTTCCCA GCTCTGCTTG TGCTCCTGAC        3450

GGGCAGGCAG GGGTCTCAAA TTTGGGAGCA GTGGGAGAGA GCAGCAGGGA        3500

AGCACAGTTG TCAGACAGGG TCCAGAAGTC CCTGAGCTAC GTTTACGTGG        3550

AAAGCGACCA GCTCTGCAAT GTCGGCCGTG CCACTTCCCT TCTTGCCGCC        3600

CAGGCTATGA CTCCCTCCAG TACCTGCCGT CCCAGTCCTC AGGAAGAAAA        3650

CTGCGAGACT CACACTTAAG TTTTATTTAC TTGTGTGTGG AGCCACAGAG        3700

CAGTTGTGGA GACCAAGAAG ACAGCTTTCT GTGCTTGCCC CTCTTCCTTC        3750

CTCTGGGTTC CCGGGATCGT GTCAGCAGCA TGAACAGCAA GTGCTTTTAC        3800

ACACAAACCG TCTTGCTGGC CCGAAATCAT ACTTTTTGGG GGTGTAGGGG        3850

GGATGAGGGG TATTTTGTTC AAAACAGTTG CATGTCACTT ATGCTGTCCT        3900

TGAATGTGTT CTGTAGCCAA GGGTGACCTT GATCTTTCTT TCTTTTTTTT        3950

TTAAAGATTT ATTTATTATT ATACATAAGT ACACTGTAGC TGTCTTCTGA        4000

CACACCAGAA GAGGGCGTCA GATCTCATTA CAGGTGGTTG TGAGCCACCA        4050

TGTGGTTGCT GGGATTTGAA CTCAGGACCT TCAGAAGAGC AGTCAGTGCT        4100

CTTAACCGCT GAGCCATCTC ACCAGCCCAA CCTTGATCTT TCTGCCTCTG        4150

CTTTCCAAGA TTTCCAGTAT GTACCAACCA CCATGCCTGG CTAATAGTAC        4200

TGTCAGTCAT TAATGGGAA ATTCAGTTAT GTCTCTGTCA TAGATGTCTT         4250

AGATGGCAAA GGTCACTTTA ATTGGGATGG GAAACAGCAC AGAGTAAGGT        4300

TCAGGACTAG AGTCAGCAAC TTGGCTTTAG AGACGCATTT AAGACCTACA        4350

CAAAAGGGAA GTGGTCTGTG GTACTTTTGA GGGCTTGTTG GAGAACAAAA        4400

GTCAGCAAAC CTTTTCCTTG AATTAGTATT GTCAGCTATG TAGAGCTTTT        4450

AGTTTCTGCT GCAACAATCA AACTCAGCTA TTACAGACAA AAGTTGGCGT        4500

AGCCATGTAA ATGAGTGCCT TTGTTTCAAT AAAACTTTAT TCATACAAGC        4550

AAATGATAGG CCAGTTTTGG TCCTGAGCTT ACCAGCCCCT ATTGTAGAAA        4600

ATGAGCAAGG CTTGTACAAG GATCTGATGT TTAGACACCA GATAGATGGC        4650

AGCTGCTGAT TGCTGCTGCT TATTGTCACT GCGCTGTTCG GGGCACAGAG        4700

CTGGCGGGTT TCTCTGTGCC TGTGTCACTG TGCTGAGTGA GCTGTTAAGT        4750

ATAAACTAGT AGCATGCTTT GGCTGAGCAT CTGTGCATGT CATGTGGGTA        4800

AAAATACCCC TTGAGGCAAG AAAGACCGTG AGTGTGCGGT GAGCGTGCCT        4850

TTGGGCTGTA TAGTAGTGTT CAGATCAGAG CATTTTAGGA ATTTACAAAA        4900

TAACCTCCGG CCTAGAACTT CCAGCCACAC TGGTGCTCGG AAGCACTGGA        4950

GCAGCCTGGG CCTTGGAGTC GTGTTGAGCC CTCTCCTGAT CCTCCCTCAG        5000

GTTATGACTT TGCGGCTGTC CTTGAGTGTT CGCAGAGCGT GTGGACCGCA        5050

TCTCTTTGTT GTTCGACGCC CACAAGCTGG ACATCTCAGA CGAGTTCTCA        5100

GAAGTCATCA AGGCCCTCAA AAATCACGAG GACAAGATCC GTGTGGTGCT        5150

GAACAAGGCT GATCAGATCG AGACGCAGCA GCTGATGCGA GTATACGGGG        5200
```

-continued

| | |
|---|---|
| CCCTCATGTG GTCCCTGGGG AAGATCATCA ACACCCCCGA GGTGGTCAGA | 5250 |
| GTCTACATCG GCTCCTTCTG GTCACACCCA CTGCTCATCC CTGACAACCG | 5300 |
| GAAGCTCTTC GAGGCAGAGG AGCAGGACCT CTTCAAAGAC ATCCAGTCTC | 5350 |
| TGCCGAGAAA CGCCGCCCTC AGGAAGCTCA ATGACCTCAT CAAGCGGGCC | 5400 |
| AGGCTGGCCA AGGTAGGCCA TGGGCTCTGC GGCTGGCATC TGGGGCCAAG | 5450 |
| GTAGCCATGG GCTCTGCGGC TGGCATCTGG GGCCAAGGTA GCCATGGCTC | 5500 |
| TGCGGCTGGC ATCTGGGGCC AAGGTAGCCA TGGGCTCTGC GGCTGGCATC | 5550 |
| TGGGGCCAAG GTAGCCATGG GCTCTGCGGC TGGCATCTGG GGCCAATGTA | 5600 |
| GGCCATGGGC GCTGAACATC ACTTTATCTG TGTGTCCTAT GTACCCACTG | 5650 |
| TGCAGCCTGT GACTCACTAA GGTCCTTTAC TTGGGTCATC TGAGCCTGTT | 5700 |
| TCTTTCTGAG GCTTATGCCT TACCTCAGAT CAGAGAGTGC GGAGAACATG | 5750 |
| CATACCCCTT AGAAATACCA AACAAGAAGT GACTACAGAA GAAAGGAGGA | 5800 |
| CACGGCAAGT GGGATGTGCT GGCCTGCTTG GCTTCAACAA ACCCCTGGGG | 5850 |
| TATATTGCAG TCTAGTGTTC TCAGCTTGGC ACGGAACAGT GTGGACTTAC | 5900 |
| TTGGGTAGGG AGTGACACAC ANCCTCCATT CAAGCCTTCA TGGAANAACA | 5950 |
| ATGCACATAC AAAGAAGCAT TGGTTATTTG GTATTGCTCA NTAGGCACAG | 6000 |
| GCTTCCGCCT GAGTGGAGGT CTGCGGAGCC ATCCTGGTGG GATGGGATTT | 6050 |
| GGGAGGCCTC CGTANGACAT GCTGGGTAAA CTGGGACAGG AAGTAGCGAN | 6100 |
| AGAAAAGATG GTACCAGTCG GTGGCCCAGA AAGTGCTGGA TGCTACCGTC | 6150 |
| CAGATCCCTG GAGGCTGCTG TCTGCACAGG CCATATAAAC ACCTATTCCC | 6200 |
| TTTGTGGGAG CTCAGGCGGG GCCCAGGTCC AATACCAGCT TCTGAGGCGC | 6250 |
| TTGAAGCCCA GGAACCTTAG TGGCCACTAA GCCTGCATGA GAGCTCAGAA | 6300 |
| TGGCCAGAGC TAGGAAGTGA ACNNCAGTGC CACCAGTGGA CTTAGGGGAG | 6350 |
| GAGGCTCTGC ATTGTGGCTT GCCCAGATAG TCACTGGGAG GGACTGTTCC | 6400 |
| AGTAATGGCT CAGGTGACCC CTTTGAACAT GAAGGTCTGA CATGGAGTGG | 6450 |
| ATGCTAGGGT AGTGCACCAG TCCAGACAGT TAGCAGGGTT CCCACTGACC | 6500 |
| CTTCAGCTGC TTAGACATAG TTCAGTTTCT TCAAAAAATG GACGGACTCT | 6550 |
| AAGCAGATGC CACAATGAAC CCATCATCAG ACTACTCTGG ATGCTGAGGC | 6600 |
| AGGAGGATCC CTTGAACAGT TTGAGACTAG TCTGAACAAC ATAGCAAGAC | 6650 |
| ATGGTCTCAA AACACAAAAG TAGGTTCTCG CCTGGCCCCT CTCTGGAAAG | 6700 |
| GGGCTGGCCT TCAGCTCAGA AGACCTGTCC TATGAGGTAC CCTGTCTCCA | 6750 |
| GGATAGCATC TCAAAGTCGG GGGTGTTTAC AAACTGATTG GTTCGCATAG | 6800 |
| AAGTGGNAAG AGATAGCCAC CAAGTGCNTA TGGCCCATTG ACCACAATCC | 6850 |
| CNTCAAGGCC AGAGAAGGTG CTTCCCAGCC ATCCCGTCCC CACTGCTGTT | 6900 |
| TGCAGTGCGA AGGCTGCTGT CCCTACACTA GATCCCAGGC CCCCACCTCT | 6950 |
| GCTCAAGGCC AGTCATGGAA TATTTGGGGG TGCCTTGGTC AGGAAACCAA | 7000 |
| GGCTGATGTT TTGTCCTTTA CTACTGCCAA GTATCAGCCA TTGTCACTCT | 7050 |
| CAAGTACCTG GCCAGGTGGC AGCCAGCCTA TGGCATTTCC CATCGTCTTT | 7100 |
| ACAGGGTCCT AGGCTGGGGG GTTTTCAGTA TCTCCAAAAG TCTAGACATG | 7150 |

| | |
|---|---|
| TATGGCCACC TTGTGAGCTG AGCAGTTCTG AGAAAGGAAC TCAATGAGAA | 7200 |
| TATCATGAGA ATTGGCCCAG GGTCCTAGGG AACTGTCAGG CAGCACTCAA | 7250 |
| CTCTCACAGC CACAGGCCTC ACGCCTGGAA CCTCTGGTCT CCAGTGTCCT | 7300 |
| CCTCACTGCT CTTAGCCCTC TGCCTGCTTT TCCTGGAGGG AAAGTAACTC | 7350 |
| CTTGGCTTAG GCAGACAGAG GTGTGACTGA GCTTGTATGA TCTGCCTGCC | 7400 |
| ATAGCTTTCT TGGAAGAACC AAGTTGCCAA CCCCAGGATT GAAAAGGACT | 7450 |
| GCCCCGGGCT GAGCAGGGAG CAGTGGGTGT GTTGAGGGGA GCTCTGGATG | 7500 |
| GAATTTCCCC ATCTTGAGTC ATCCTGGCCT GTTTTGATGG CACATGGCAT | 7550 |
| ATCACTCAAG TGGGATTCTA CTTGGGACTT CCCATGTACT GTACAGATAT | 7600 |
| ATGTCTGGCA GAGGCTCATT CACAACTTTC TATGGCTCTG CAATGTGTTG | 7650 |
| CTTTTATTAT CGGGAGGGGG CAGCTCGGGG AGAAAACAGG CAGAACTGCG | 7700 |
| TTGTAGTCCA CTCTCTGCAG TCCTCACATA GTTCTTGACA AACCTCTGAG | 7750 |
| CCTCCTCTGA CCACAGTAGA TTTGGATGCA TGAGAAGGGA GTGCCTCTAA | 7800 |
| GCACCCATCT TATGACAGAC TCTAGAGTCG TTGTCTCTAG AATGTCACCA | 7850 |
| TGACTTGTAC AAGAATGGGT TGGAGAGATG ACTCAGCAGT TAGCAGCACT | 7900 |
| CAGGCTCAAT CCCAGCACCC CCAACTGTCT GTAACTTTAG CTCCAGGGGA | 7950 |
| TCCAGAACCC TCACACAGGC ATACATGTAG TCAAAACAGC AATATACAAA | 8000 |
| GAAGATAGAC AGACAGACAG ATAGATAGAT AGTTTTTGCC AGGCCAGTGG | 8050 |
| TGGCACACAC CTTTAATCCC AGTACTTGAA AAGCAGAGGC AGGAGGATTT | 8100 |
| CTGAGTTTGA GGCCAGCATT GTCAACAGAG TGAGTTCTAA GACAGCAAGG | 8150 |
| GCTACCCTGT TTTGAAAAAC AAAAACAAGA AGGAGTGTCC ATCTTCTGTG | 8200 |
| CCGTGTTAGA GGCACCCTTT CCTCCCCTGC CCGAGCACTG AGCTTGAGGC | 8250 |
| ACTGGAGGCC TTGACAGCCC TGAGGGCAGC GTGCCAAGCA AGTNCCCTGA | 8300 |
| TGCCCACTGC TTCCTCCCTN TAGGTCCATG CNAANTNATC AGAGTCCATG | 8350 |
| CCTACATCAT CAGTTCCCTC AAGAAGGAGA TGCCCAATGT TTTCGGGAAA | 8400 |
| GAGAGCAAGA AGAAAGAGCT GGTGAACAAC CTGGGAGAGA TCTACCAGAA | 8450 |
| GATCGAGCGG GAGCACCAGA TCTCCTCCGG CGACTTCCCA AGCCTGCGTA | 8500 |
| AGATGCAGGT ACAGTCACCA GGCCAGCCTG CCCGGGGCTG GGTACCCAGC | 8550 |
| TCTATAGAAC AGGGCCTCTA CAAAAGGAAG CAGCTGGGTT AGTCACCAGT | 8600 |
| TCCCTATCTG AGTCAGAGTT ACCTAGGTCG AGACACTGAC ACGAAAAAGG | 8650 |
| GGAATGTGGT GACTCAGCTT TGGGGTGGGG CATGGCTGTT GGTGAATCTT | 8700 |
| CATAGCCCAG CAGGGATAGT GCAGTTGTGA CCTCACGCAG AGTGAGGAGC | 8750 |
| TCAGGCCTGT GGCACTAGCT CAGTAGCCTG AACTGGTAGG TGGAAGCCCC | 8800 |
| ACTCCCCTGC TTGGATAGTC TAGCTCAGTC TGGAGTCTGG AAGACTGCCC | 8850 |
| CATCTAGGCC TCTCCTTCCT TCTACACTCA CAGGAACTCC TGCAGACCCA | 8900 |
| GGACTTCAGC AAGTTCCAGG CCTTGAAGCC CAAGCTGCTG GATACAGTGG | 8950 |
| ATGATATGCT GGCCAACGAT ATAACTCGGC TGATGGTGAT GGTGCGCCAG | 9000 |
| GAGGAGTCCC TGATGCCCTC ACAGGCTGTG AAGGGTGGTG CTTTTGATGG | 9050 |
| CACCATGAAT GGGCCCTTTG GCATGGCTA CGGCGAGGGG CTGGCGAGG | 9100 |
| GCATTGATGA TGTTGAGTGG GTAGTTGGCA AGGACAAGCC CACCTATGAT | 9150 |

|  |  |
|---|---|
| GAGATCTTCT ACACACTGTC TCCTGTCAAC GGCAAGATCA CAGGTGCTAA | 9200 |
| TGCCAAGAAG GAGATGGTGA AGTCCAAGCT GCCCAACACA GTGCTGGGGA | 9250 |
| AGATCTGGAA GTTGGCAGAT GTGGACAAGG ATGGCCTGCT GGATGACGAG | 9300 |
| GAGTTTGCCC TGGCCAACCA CCTTATCAAG GTGAAGCTAG AGGGCCACGA | 9350 |
| GCTGCCCGCT GACCTTCCTC CACATCTCAT TCCACCCTCC AAACGGAGGC | 9400 |
| ACGAGTGACT TCCATGCCTG AACCCTACAA CCCCCAGGGC TGCTGCCACT | 9450 |
| TTCTACCCAC CAGCTCCTTG TCTGCCCAGG TGGGCTGGGG CCTGGAGGGG | 9500 |
| CAGAAATTGG GGGAGGGAAA GGGTCACCAT TTTTCAAGGT CCATAAAGAC | 9550 |
| TGAGCGGTGT TTCCTCAGCT CTTGAATAGG AAAACCACCA TCTTTCTTTT | 9600 |
| AAAGCTGTTC CGGGGTTCAG CGGGAGGCAT GGGTGATGCT TGGATATGAA | 9650 |
| CAGTGGGATT TTGTGCACAG GAACCATGAT ATTTTTAATA TATAACATTA | 9700 |
| GAGGCAGCCT TCTTTCTTGC CTCTTCTGTC TGACAGCCCC ACACTCATCC | 9750 |
| TCTCCCCTAT CCAAGCCAGG CACCTCTCCA CCCCACCCTG GCACCCCTGT | 9800 |
| GCCCGATGCC CCAGGGCTGT GTAAGCAGGA GGTCCCTGCT CCTTCAGCTT | 9850 |
| GTTTTTAGAC TGGGGCTCCC TCAAGGGCAG CAGGTTGTTT CCTGCTAGCC | 9900 |
| GTGTTCTGTG CTCCAGTCCT CTGCTGTGCT GTGGGTGCA CACCTTACTC | 9950 |
| TGTCCACATC CCCTGACACC CCAGCCAGCA CAGCAGCCCA GGTAGAAGAC | 10000 |
| CCAACCACTG TTATTTGTTG TGGAGGCAGG AGGAGTTGCG AGACAGTCCA | 10050 |
| TGACGTCTAG GAAAATGCAT AAGCTACTTA GTGTTCTGTA GTGACACTTG | 10100 |
| ATACTTGACC AAGACTTTGA GTAACTTACA TCACTCGTTC AAAACTGTGA | 10150 |
| TTTTTGTCTC CTCTTTCCTA TACTCCAGCC TTGGAGCATT TCCACCCCAG | 10200 |
| AGCCAGCATA GAGCTGACAT CCTAGGGCTT GAGTTTGCTT TCTGGCTGAG | 10250 |
| GGGAGGTCAT CCCAGCTTCT GCTCAGAGGG GTCTGAAATG TAGCCCCCCC | 10300 |
| ACCCCCGCCC CAAGGTCAAC CTTTATGGCA GCTTCCTGGA GCCCCTCTCT | 10350 |
| GCCTTGGGAC AGGCAGTAGG CCCTGTGACC TGGGGTGGTC TGGGGCTGGT | 10400 |
| AAGAGGAAGC CTGTGGCTCT GGCCTGGGTG TAGTGTCCAT GCAGCACGAC | 10450 |
| AGGGGAAAAC CCAGCCCCTT CCCTCGCCCT GTCATTTCCT TCCTCTCCTC | 10500 |
| CTCTGCTGAG CCAAGGAGGT CTGGGTGTCC TGAGAGCCCC AGACTGAGCA | 10550 |
| GTAAGAAGCC TGAGCTAGCA AATGACCACT TTAGTCACCC CACTGTAGCC | 10600 |
| TGGGGACCCG GACACATCCT GTGGCCAGTG GTTGGCTGTC AGGGTGGGCT | 10650 |
| TTCCACTGAG CTGGGTAGGG CATTGCAGCC TGCTCCTCTG ACACTGTAGG | 10700 |
| TGGGCTTCAG GGAGCTGCCT GCCAACCCCC AGCACTGTT CTGGGCCCTG | 10750 |
| CTGAGGGTGA GCTCCAGCCT GGCCTGTTAC CTCCCTGCCT CAGCCCTCCA | 10800 |
| CTCCTTGGCT GAGGGTGAGA GAGATGTCAT CCTCAGCTGT AGAGGGAGTG | 10850 |
| GCCGAATGAA GACTGGTTCT CGCATTAAAG GAAGTTTAAT TGTGCCAAAG | 10900 |
| CCTCTCATGC TCCCTTGTCT TTTCCTGGCC AAGGAGGCAC CCCTGGAGCC | 10950 |
| TTGCAAGGGG TCCCCCAAGT TGTCCATAAC CACCCATCTC CTGTGCATTG | 11000 |
| TTGGCGAGAC TATCTGGAAA CTGAACTTGA TGGTGCACAC CCATAGTCTC | 11050 |
| AGCACTTGGG ATGTGGGGGG GAGGACCAAG CTACATGAGA GCCTGTCCCC | 11100 |

-continued

| | |
|---|---|
| AAAAATCTAA ACACCAGTAG AGATTGATAT CAGAATTATG CTGGGCCCAC | 11150 |
| TTCCACATCT GCACATCATC ACCTCCCTCA AGACCGCCAC AGCTGTAGAC | 11200 |
| AGACAGGATG GGCTCCCCTC CCTAGTGTCC TCAGACTGGG TTGTGGGATC | 11250 |
| CTGTAAACAA AGGTCCCAGG GCTCCGAGCT GCTTGGCTCC TCACTTGCCC | 11300 |
| CCAGGCAGGT TTGGAGCCAG CAGAGCCAGC TCTGAAGACG GCAGAGGCTG | 11350 |
| ACAAAAATCC ACAGTTCTGG GTGGGGTTGG TTAGAGCCAG CTGATGTCTC | 11400 |
| CGATAGGGGA CCTGTTTATG ACAAGAGAGG AAAGGATGAC AAATTGGGAG | 11450 |
| TGACATGCCC GGAAGGGTGC AGATGGGAAG TAAGGCGGGG AGAGACAGCT | 11500 |
| CCAGGCAAGG TTGGGACAGA AGCCCGGAAA AACAGGTGTT TATCTTAGAT | 11550 |
| CCAGAGCTGC CTCCAGGGTC TAGCTGCTGT GGCTAAGGCA GGCCTGATAG | 11600 |
| TCCAGGCACC TCAGACTTGA CACCCCTGTG TGGTCTGCGG GGCTTGCCTG | 11650 |
| AACCTCAGCA TGAGAGGGCA ACACAGGCAG CAGTGGTAGC CAAGGAGATC | 11700 |
| AGACTGAAGT CTACCAACTC GGGTCCCATT CCTGAGGAGT GTCATGGAAA | 11750 |
| CCCTTTTTAA AGCAAAGGTG ATTTCTGAGT TGCCCAGCCC ACTTCACCCT | 11800 |
| CAGCTGCCAC TCAGGGTTAA AATGCTCCTG GAATGATTCA AAGCTGTCAT | 11850 |
| TCCACCTGAG ATTTTAGATG CTTGGGTCCC ACAGAGATGC CCTGTGCTTG | 11900 |
| TTCAAGCTGG TAGTGCCAAA GGAAACAGGC CCAGGGAGCT CCCTGGAATG | 11950 |
| CTAGGACCCA CCTTCACTCC ACCCGTGGGA CTCATGGTAT ACTATCTGTT | 12000 |
| CAGCGCCCAT CTCTATGAGA TGATACCCAG ATGGTGCCCA CTGGGTAAGA | 12050 |
| AGTTTAAGGC GGGGCGGTGA TGGCACACGC CTTTAATCCC AGCACTTGGG | 12100 |
| AGGCAGAGGC GGGCGGATTT CTGAGTTCGA GGCCAGCCTG GTCTACAAAG | 12150 |
| TGAGTTCCAG GACAGCCAGG GCTACACAGA GAAACCCTGT CTTGAAAAAC | 12200 |
| CAAAAAAAG AAAGAAAGAA AAAAGGTTT GAGAGCAAGT GAAGGCCTCC | 12250 |
| CCTTCTGCTG CCCCTGGACT CAGGTTTGGG TTTCATGATT CAGACTCCTC | 12300 |
| TGGGCCATGG TGGGAACTGA GGAAGAGATG TCCACTCAGA GGGCTGGCTC | 12350 |
| TTGCCCCGCC ATTCCTTTCT TGTTCTCTAG AAGCCAGAAT ATATCAGGAA | 12400 |
| GCAAATCCTT GCCACCCTGC TCCCAACCCC TGGGATAAGA GGCCTTCAGG | 12450 |
| ACAGTCTGCC ATCCTAGCTC ACAGCACCAC ACAAACCCAA GACCCACAG | 12500 |
| GCCCAGAAGC CCACCTGCAG GCTGCACCTG CCAGCTGTTT AGTGAGCCGA | 12550 |
| GGTTTCCATT GTTAATCTGG TCATAGGATT GTCTGCAGCC AGTGGGCTAA | 12600 |
| TATGACAGTG GGGGAAGAGG ACCAGTGAGA GAAGGGTTCA GTAGTTTAGA | 12650 |
| GCACTGGCTG CCCTTCCAGA GCATCTGGTT TTGACTTCCC AGCACTCACA | 12700 |
| TGGCAGCTGA CAACCATCTA TATAACTTGT TTCAGGGGAA CTGTCTTCTG | 12750 |
| ACTTTCAAGA CTACTCAAAT GTGGTATACA GACATAAATG CTGGCAAAAC | 12800 |
| ACCAATACAC CTCAAATAAT AAAACAGAGG ACAGCCAGCC ATCGTTCCTG | 12850 |
| GCCTCTGCTT TCAAAACTTA AAGCTTCAAA GCTGGGGTGC TGACCAGTAA | 12900 |
| GAAGGCCTGA GTTCAATACT CAGAACCCTA TAAAACCAA TATGGCGGTG | 12950 |
| CATACTCATG ACCCTTGTAC TAGAGGCAGA TACAAGCCGC AGATGTGACC | 13000 |
| GGCCAGCCAA GCCCATGAGC GGTCCTGTCT AAAGTGAGGT GAATAGTATC | 13050 |
| TGAGGAAGGA TCCAGGACTG CATGCACACA TGCACCTATA CACACATATA | 13100 |

| | |
|---|---|
| TCTGCATGCA CACATACACA CAAAGCTTGT ATGTATAGGA CTGGATAAGA | 13150 |
| CAATGGGTTT GATCTCTCAC AGCACTGCAA ACAAACCGTT ATCATCTGTC | 13200 |
| AGCAGTTAGC AATTTTGACC AAAAAGCCCT ATGTTTAAAT CTGTCACTTG | 13250 |
| CTGGAGTCAA GCCTGCCTTT TTCCTTTTAA TCCTGTTCAT TGGGCTCTGA | 13300 |
| GGAGACCATT GCTCAATGGC TTTCTTCTCT AGGCACCTTG GCTAGTCAGG | 13350 |
| GGGGTGAGGT ATGTGGGGAG CATGTACCCC ACCCAACACC CAGAACAAAA | 13400 |
| CAGAAGGACC CACCCTTCCC TGAAGTAGCT CAGACAGGGT GGCGCCTATG | 13450 |
| AGCTGCAGGG GTGTAGGGTA AGGGGGCTAG GGCCTGGCTT CCTGTGCACC | 13500 |
| CGGAGAGGCT GGTAATTGCA AAACCACATG GGCTGCTGCT GAACAGAGCA | 13550 |
| GAGCGTGGGA GCCCCTGTGG TGAGCTGGAG CAGCCAAGGG GAGGATTTGG | 13600 |
| GAAGCAAACC GAGGATGATG AAACCACCAT ATGTCCACCC ATTTGGAGTG | 13650 |
| TTGGACATTT CACAGTTAAT ATCCAGAGTG CAGCAGGCAG GAATATGGTG | 13700 |
| TGGGAGCTGG CACAGGTTTA AATGTGAGGG GTCTCCGCTG ACCCAAAGGA | 13750 |
| ACCTTCAAAC AAGCCCTGAG CAGCAGAGGC AGGGATATTG GGCTCTCTGC | 13800 |
| CTCAGATGGC CCCATGTTAT TCCTAGACAG AAATGTTATA CAAACCAACT | 13850 |
| GGAGCCCCAT GAGGAACCCA TGCCACCAGG TTTCCCTTGT CCCAATCAGG | 13900 |
| TGCCTCTCTC CATTGTCCAT AGAAGGTGTT CAGAGAGAGG GTAAGGAGAC | 13950 |
| TTGCCCGCGG CAGTACACCT GGGCCACAGT AAGCAGACCC ATGGGACCCC | 14000 |
| ACAACCAGCC TCCGGTCCCC AGCTCTCCGG AGTCGAGGAG GACAGTCGCT | 14050 |
| CGTTCTTGGA ATGCTGAACC ACAGATTTTT GCGCTGCTTC TGAAACTGGG | 14100 |
| GCTAGGAGAT TCAGCCGCCC CAAGGGGCAT TTTAGATGAG CAACTGCAAG | 14150 |
| CTTAGACTCA GAAAGCNTGA AATGTGGCCA CAAAAATTAC CGGCACCTTT | 14200 |
| CCCCTGGCCC ATCTTGTATN TGGGTTCCTT TCAGACTCAA AGGGTGTCAG | 14250 |
| AAACACCCAA GCATTCTGCC CCAAGTCCCT TCTCCTTCAG GGTCTGTCCC | 14300 |
| TTCTGGGAAC TTTGTTTCTC TTGAGCCTGA GCTCTGAGGT GACACAATCC | 14350 |
| ATTCTTTATC CAGAAGCTTT TATAGGAGCA TTTACCAAGC CTGTCTAGGG | 14400 |
| AGGGCCTTGC CTTCTTCCAT ATGTCCCACA GCCCACAGTA CCCTTTTGCT | 14450 |
| GCTGGCAATG GGGAATAGGC ACTCAGGGTG CGGACTACAG GAAGAACCTA | 14500 |
| GAACTGTTTG TGTCACTGCC TCCTGGCCTC CCTGTGTCAA CCTGTGAAGG | 14550 |
| AGGTAGATAA TAATATAGCT GTCTGGTAGA GATCAGAGAT CGAGTCGACT | 14600 |
| CCCTTTAGTG AGGGTTAATT GAGCTCGCGG CCGCACTCGA GCACCACCAC | 14650 |
| CACCACCACT GAGATCCGGC TGCTAACAAA GCCCGAAAGG AAGCTGAGTT | 14700 |
| GGCTGTG | 14707 |

(2) INFORMATION FOR SEQ ID NO:4:

(i) SEQUENCE CHARACTERISTICS:
        (A) LENGTH:534
        (B) TYPE:amino acid
        (C) STRANDEDNESS:single
        (D) TOPOLOGY:linear (xi) SEQUENCE DESCRIPTION: SEQ ID NO:4:

Met Phe Ser Trp Val Ser Lys Asp Ala Arg Arg Lys Lys Glu Pro

```
                  5                  10                 15
Glu Leu Phe Gln Thr Val Ala Glu Gly Leu Arg Gln Leu Tyr Ala
                 20                 25                 30
Gln Lys Leu Leu Pro Leu Glu His Tyr Arg Phe His Glu Phe
                 35                 40                 45
His Ser Pro Ala Leu Glu Asp Ala Asp Phe Asp Asn Lys Pro Met
                 50                 55                 60
Val Leu Val Gly Gln Tyr Ser Thr Gly Lys Thr Thr Phe Ile
                 65                 70                 75
Arg His Leu Ile Glu Gln Asp Phe Pro Gly Met Arg Ile Gly Pro
                 80                 85                 90
Glu Pro Thr Thr Asp Ser Phe Ile Ala Val Met His Gly Pro Thr
                 95                100                105
Glu Gly Val Val Pro Gly Asn Ala Leu Val Asp Pro Arg Arg
                110                115                120
Pro Phe Arg Lys Leu Asn Arg Phe Gly Asn Ala Phe Leu Asn Arg
                125                130                135
Phe Met Cys Ala Gln Leu Pro Asn Pro Val Leu Asp Ser Ile Ser
                140                145                150
Ile Ile Asp Thr Pro Gly Ile Leu Ser Gly Glu Lys Gln Arg Ile
                155                160                165
Ser Arg Gly Tyr Asp Phe Ala Ala Val Leu Glu Trp Phe Ala Asp
                170                175                180
Cys Trp Asp Arg Ile Ile Leu Leu Phe Asp Ala His Lys Gln Asp
                185                190                195
Ile Ser His Glu Phe Ser Glu Val Ile Lys Ala Leu Lys Asn His
                200                205                210
Glu Asp Lys Ile Arg Met Val Leu Asn Lys Ala Asp Gln Ile Glu
                215                220                225
Thr Gln Gln Leu Met Arg Val Tyr Gly Ala Leu Met Trp Ser Leu
                230                235                240
Gly Lys Ile Ile Asn Thr Pro Glu Val Val Arg Val Tyr Ile Gly
                245                250                255
Ser Phe Trp Ser His Pro Leu Leu Ile Pro Asp Asn Arg Lys Leu
                260                265                270
Phe Glu Ala Glu Glu Gln Asp Leu Phe Lys Asp Ile Gln Ser Leu
                275                280                285
Pro Arg Asn Ala Ala Leu Arg Lys Leu Asn Asp Leu Ile Lys Arg
                290                295                300
Ala Arg Leu Ala Lys Val His Ala Tyr Ile Ile Ser Ser Leu Lys
                305                310                315
Lys Glu Met Pro Asn Val Phe Gly Lys Glu Ser Lys Lys Glu
                320                325                330
Leu Val Asn Asn Leu Gly Glu Ile Tyr Gln Lys Ile Glu Arg Glu
                335                340                345
His Gln Ile Ser Pro Gly Asp Phe Pro Ser Leu Arg Lys Met Gln
                350                355                360
Glu Leu Leu Gln Thr Gln Asp Phe Ser Lys Phe Gln Ala Leu Lys
                365                370                375
Pro Lys Leu Leu Asp Thr Val Asp Asp Met Leu Ala Asn Asp Ile
                380                385                390
Ala Arg Leu Met Val Met Val Arg Gln Glu Glu Ser Leu Met Pro
                395                400                405
```

Ser Gln Val Val Lys Gly Gly Ala Phe Asp Gly Thr Met Asn Gly
                410                 415                 420

Pro Phe Gly His Gly Tyr Gly Glu Gly Ala Gly Glu Gly Ile Asp
                425                 430                 435

Asp Val Glu Trp Val Val Gly Lys Asp Lys Pro Ser Tyr Asp Glu
                440                 445                 450

Ile Phe Tyr Thr Leu Ser Pro Val Asn Gly Lys Ile Thr Gly Ala
                455                 460                 465

Asn Val Lys Lys Glu Met Val Lys Ser Lys Leu Pro Asn Thr Glu
                470                 475                 480

Leu Gly Lys Ile Trp Lys Leu Ala Asp Val Asp Lys Asp Gly Leu
                485                 490                 495

Leu Asp Asp Glu Glu Phe Ala Leu Ala Asn His Leu Ile Lys Val
                500                 505                 510

Lys Leu Glu Gly His Glu Leu Pro Ala Asp Leu Pro Pro His Leu
                515                 520                 525

Val Pro Pro Ser Lys Arg Arg His Glu
                530

(2) INFORMATION FOR SEQ ID NO:5:

(i) SEQUENCE CHARACTERISTICS:
        (A) LENGTH:534
        (B) TYPE:amino acid
        (C) STRANDEDNESS:single
        (D) TOPOLOGY:linear (xi) SEQUENCE DESCRIPTION: SEQ ID NO:5:

Met Phe Ser Trp Val Ser Lys Asp Ala Arg Arg Lys Lys Glu Pro
                5                   10                  15

Glu Leu Phe Gln Thr Val Ala Glu Gly Leu Arg His Val Tyr Ala
                20                  25                  30

Gln Lys Leu Leu Pro Leu Glu Glu His Tyr Arg Phe His Glu Phe
                35                  40                  45

His Ser Pro Ala Leu Glu Asp Ala Asp Phe Asp Asn Lys Pro Met
                50                  55                  60

Val Leu Leu Val Gly Gln Tyr Ser Thr Gly Lys Thr Thr Phe Ile
                65                  70                  75

Arg His Leu Ile Glu Gln Asp Phe Pro Gly Met Arg Ile Gly Pro
                80                  85                  90

Glu Pro Thr Thr Asp Ser Phe Ile Ala Val Met His Gly Pro Thr
                95                  100                 105

Glu Gly Val Val Pro Gly Asn Ala Leu Val Val Asp Pro Arg Arg
                110                 115                 120

Pro Phe Arg Lys Leu Asn Ala Phe Gly Asn Ala Phe Leu Asn Arg
                125                 130                 135

Phe Met Cys Ala Gln Leu Pro Asn Pro Val Leu Asp Ser Ile Ser
                140                 145                 150

Ile Ile Asp Thr Pro Gly Ile Leu Ser Gly Glu Lys Gln Arg Ile
                155                 160                 165

Ser Arg Gly Tyr Asp Phe Ala Ala Val Leu Glu Trp Phe Ala Glu
                170                 175                 180

Arg Val Asp Arg Ile Ile Leu Leu Phe Asp Ala His Lys Leu Asp
                185                 190                 195

Ile Ser Asp Glu Phe Ser Glu Val Ile Lys Ala Leu Lys Asn His

```
                    200                 205                 210
Glu Asp Lys Ile Arg Val Val Leu Asn Lys Ala Asp Gln Ile Glu
                    215                 220                 225
Thr Gln Gln Leu Met Arg Val Tyr Gly Ala Leu Met Trp Ser Leu
                    230                 235                 240
Gly Lys Ile Ile Asn Thr Pro Glu Val Val Arg Val Tyr Ile Gly
                    245                 250                 255
Ser Phe Trp Ser His Pro Leu Leu Ile Pro Asp Asn Arg Lys Phe
                    260                 265                 270
Phe Glu Ala Glu Glu Gln Asp Phe Phe Lys Asp Ile Gln Phe Leu
                    275                 280                 285
Pro Arg Asn Ala Ala Leu Arg Lys Phe Asn Asp Leu Ile Lys Arg
                    290                 295                 300
Ala Arg Leu Ala Lys Val His Ala Tyr Ile Ile Ser Ser Leu Lys
                    305                 310                 315
Lys Glu Met Pro Asn Val Phe Gly Lys Glu Ser Lys Lys Lys Glu
                    320                 325                 330
Leu Val Asn Asn Leu Gly Glu Ile Tyr Gln Lys Ile Glu Arg Glu
                    335                 340                 345
His Gln Ile Ser Ser Gly Asp Phe Pro Ser Leu Arg Lys Met Gln
                    350                 355                 360
Glu Leu Leu Gln Thr Gln Asp Phe Ser Lys Phe Gln Ala Leu Lys
                    365                 370                 375
Pro Lys Leu Leu Asp Thr Val Asp Asp Met Leu Ala Asn Asp Ile
                    380                 385                 390
Ala Arg Leu Met Val Met Val Arg Gln Glu Glu Ser Leu Met Pro
                    395                 400                 405
Ser Gln Ala Val Lys Gly Gly Ala Phe Asp Gly Thr Met Asn Gly
                    410                 415                 420
Pro Phe Gly His Gly Tyr Gly Glu Gly Ala Gly Glu Gly Ile Asp
                    425                 430                 435
Asp Val Glu Trp Val Val Gly Lys Asp Lys Pro Thr Tyr Asp Glu
                    440                 445                 450
Ile Phe Tyr Thr Leu Ser Pro Val Asn Gly Lys Ile Thr Gly Ala
                    455                 460                 465
Asn Ala Lys Lys Glu Met Val Lys Ser Lys Leu Pro Asn Thr Val
                    470                 475                 480
Leu Gly Lys Ile Trp Lys Leu Ala Asp Val Asp Lys Asp Gly Leu
                    485                 490                 495
Leu Asp Asp Glu Glu Phe Ala Leu Ala Asn His Leu Ile Lys Val
                    500                 505                 510
Lys Leu Glu Gly His Glu Leu Pro Ala Asp Leu Pro Pro His Leu
                    515                 520                 525
Ile Pro Pro Ser Lys Arg Arg His Glu
                    530

(2) INFORMATION FOR SEQ ID NO:6:

(i) SEQUENCE CHARACTERISTICS:
        (A) LENGTH:3635
        (B) TYPE:nucleic acid
        (C) STRANDEDNESS:double
        (D) TOPOLOGY:linear (xi) SEQUENCE DESCRIPTION: SEQ ID NO:6:
```

```
GCCGCGCCGG GGGCGGCGGG ATGCTGCTGC GGATGCGGAG CTGTGTGAGC        50

CGCTGCCTAC CCGGCGCAGC CTGGGCTCCG CAGTAGCGGA GCTCGAGCAT       100

CCTTTAGTCA TCTATCTGGG GAGACCTGGA ACTCAGGCTT CGGCTTCCCG       150

GCAGGTTTGT CTTTAATTTC CAAGGTTGCA GTTCTCTTGA CACAATCCAC       200

AGCATCCTTC TCTCCAACCG GGCTGTGGAT GAACCTGGGA CTGGACTGAA       250

TCCAGCAGCT GGGGCAGCCC GGGCCATGGT GCGTCTGAGC CCCGAGCTCT       300

GGTAAGGCAG TAGTGGCGGC GTTGTTCGAG CTAGGCGGGT GCCACTCCCG       350

GGAGCTTCCT CCCAGCTGTC ACAATGTTCA GTTGGCTGGG TAACGATGAT       400

CGCCGCAAGA AGGACCCTGA GGTCTTCCAG ACGGTGAGCG ATGGACTCAA       450

AAAACTCTAC AAGACCAAGC TGCTGCCTCT GGAAGAGTAT TACCGCTTCC       500

ACGAGTTCCA CTCGCCCGCC CTGGAAGATG CTGATTTCGA CAACAAGCCC       550

ATGGTCCTGT TGGTGGGCCA GTACTCTACC GGCAAGACCA CCTTCATCAG       600

GTACCTGCTG GAACAGGATT TTCCAGGCAT GAGGATTGGG CCTGAGCCGA       650

CCACTGATTC CTTCATAGCA GTGATGCAGG GAGATGTGGA GGGGATCATT       700

CCCGGGAATG CCTTGGTGGT GGATCCAAAG AAACCCTTCA GAAAGCTCAA       750

CGCCTTTGGC AACGCCTTCC TGAACAGGTT TGTGTGTGCC CAGCTGCCCA       800

ACGCCGTGCT TGAAAGTATC AGTGTGATCG ACACACCGGG GATCCTCTCT       850

GGGGAGAAGC AGAGGATCAG CCGAGGGTAT GATTTTGCTG CGGTCCTCGA       900

ATGGTTTGCT GAGCGGGTGG ACCGAATTAT CCTACTCTTC GACGCCCACA       950

AGCTGGACAT CTCCGATGAG TTCTCAGAAG TCATCAAGGC TCTCAAGAAC      1000

CATGAGGACA AGATGCGCGT AGTGTTGAAC AAGGCTGACC AGATCGAGAC      1050

CCAGCAGCTG ATGCGAGTAT ACGGAGCCCT CATGTGGTCC CTGGGGAAGA      1100

TCGTGAACAC CCCCGAGGTG ATCCGGGTCT ACATTGGCTC CTTCTGGTCC      1150

CACCCACTCC TCATTCCCGA CAACCGGAAG CTCTTTGAAG CTGAAGAGCA      1200

AGACTTGTTC AGAGACATTC AGAGTCTACC CCGTAATGCT GCTCTTCGAA      1250

AGCTCAACGA TCTCATCAAG AGAGCCCGGC TGGCCAAGGT CCACGCCTAC      1300

ATCATCAGCT CCTTGAAGAA GGAGATGCCC TCAGTGTTTG GAAGGACAC       1350

CAAAAAGAAA GAACTGGTGA ACAACCTGGC TGAGATCTAT GGCCGGATTG      1400

AGCGAGAACA CCAGATCTCC CCTGGAGACT TCCCCAACCT GAAGAAGATG      1450

CAGGACCAGC TGCAGGCCCA GGACTTCAGC AAATTCCAGC CACTGAAGAG      1500

CAAGCTGCTG GAAGTGGTTG ATGATATGCT GGCTCATGAC ATTGCCCAGC      1550

TCATGGTGCT GGTGCGCCAG GAAGAGACCC AACGGCCTGT CCAGATGGTG      1600

AAGGGCGGAG CATTTGAGGG AACCTTACAA GGCCCCTTCG GCACGGCTA       1650

TGGAGAGGGA GCTGGGGAGG GCATCGATGA TGCCGAGTGG GTGGTGGCGC      1700

GGGACAAGCC TATGTATGAT GAGATCTTCT ACACCTTATC CCCAGTGGAT      1750

GGCAAGATCA CAGGTGCCAA CGCCAAGAAG GAGATGGTGC GCTCCAAGTT      1800

GCCCAACAGC GTGCTGGGCA AGATCTGGAA GCTAGCCGAC ATTGACAAGG      1850

ATGGCATGTT GGATGACGAG GAGTTTGCCC TGGCCAACCA CCTTATCAAA      1900

GTCAAGCTAG AGGGGCATGA GCTGCCCAGT GAGCTACCTG CCCACCTCCT      1950

CCCTCCATAT AAGAGGAAAG TATCAGAATG AGAGAGCCAG GTAACCTCAG      2000
```

| | |
|---|---|
| ACAGACAGTA TCAAAAGAGA GGATAGACAT GTAGACCACA CACACACACA | 2050 |
| CACACACACA CACACACACA CACACACACA ACTTGACAGT CACACTATAA | 2100 |
| ATGAGAAGGG TTCACCTTTG TCTGAGCACC TCTCCAAGTT CCCAGGGTTG | 2150 |
| GTAGAAGGGC AGCTTTCCCT CCTCTGTCTT AGGATATAGG CCTGTGTCCA | 2200 |
| AACATTCCCT CCATCTTCCA TTCCCCCACA GACATGAGGC AGTTAACACA | 2250 |
| GATGGCCCAC CCACTCTACC CCCAGTGCCT CCACATCTAG GCTCCGAGCA | 2300 |
| GATGGAAAAG GCTTTTTCAT GGAATAGAAA ATTTGCTTTA TTTTCTATGC | 2350 |
| TTTTATTTTT TTTCCCTCTG GGGCTTCCTA AGTAGAAATT GACTCAGGGC | 2400 |
| CTGGGAGCTG TGAGGGAAAG GAGAAGCTGA AAGAGGAGGA CCAATCTGAG | 2450 |
| AAACCTCCAT AGGGCACTGC ACCCCACACT TGAAAGACA CTGGCCTATG | 2500 |
| TTCTCTGTGT TTTTCTCAAC CCAAGACTCT CTGTCTTCCT CAGTAAACAT | 2550 |
| GGACCTTGAA TTCTGCCTGC CACTTTGGGT CAAAGACTCA CAAACAGGAA | 2600 |
| AAGAAAAAAG AAAAAATTTG GTAGGAAAGC AACAAGGAAG ATAACCCTGT | 2650 |
| GTTTTTTTTT CAACAGGACA TTGGATTGGT GGTTCATGGG TTTGTCCCCC | 2700 |
| ACCCCCAGCG TGGTATCTCT GGATACTCAG TTTCTTTATA CATACCAAGC | 2750 |
| CATTCCTGTG TGGCAAGAGC AGGGTTAGGC ACTTTCTATG TATTAGTCCC | 2800 |
| TGTGGCCTTC ATGAATGCCC TAGGCAAGTT TGNTTCCCTC CTGTTACTGC | 2850 |
| ATTTTTCAGG TGAAGAGCCA AAGACTCAGA GTAGTTTAGG GTACCTTCCC | 2900 |
| AAACTCCGGG AAGTCCCAAG AAGAGAAGAT TCAAATCCAG AACTTGAGAC | 2950 |
| ACCCCTCTGT CCCAATTCTG TGATGGATGA AAGATCCCAG TGTTGCTACG | 3000 |
| TGGTGACAAA GCACAGGACA GTCTGAACAC ACAGCCCCTC ACACAGCCTT | 3050 |
| CCAAAGCATC CAGGCAAGGG AGGGAGGGAG GTTCACCAGC CTTTGATGGG | 3100 |
| CCAACAATCT GACCATCTGT CACCTTGTAG AAGCAAACTG TGCCTTCTGG | 3150 |
| CCTGCGCCTC GTGTTCACAA CATCACAGAA GACCAGCCAA GCCATCAGGA | 3200 |
| GAGTGGGCTG GACTGCTAGA TGTTGTCTGT GCCTATTCCT GCTCAGCCTC | 3250 |
| CCGTTCATTA GCCTAAAGCA TCCCAGCTCA AATTCAGCCC CAGGCTTTTA | 3300 |
| CAAAGCAGGA CTTCATGCTA ATTCACGAAA GGCCATCTTG AAAGGACTGG | 3350 |
| GACCTTGTTC TCTAGAGTTC CAAGGACTCT GGTGTCCTTG GCAAAATTTC | 3400 |
| CATCATTCTC AGTGCCCTCT ATCTCCTCTG TGGTCTCCCC CTGGCTTGCC | 3450 |
| CTATGCCCAC TGTTGCAGTA GCTCTCTGCT ACACTCCTAC TGTGATGGAA | 3500 |
| AACAAAGCAA GTATAACTTA TTTTGTATCT ATGTTCAGAC TATATCGACT | 3550 |
| GTTCTGTGTA TCTTCAATGT GCTTATAACT GCAGTGTGTT TGTCATTAGG | 3600 |
| ATTCATGTTA ATACAACATA TTTACCCTCG TGCCG | 3635 |

(2) INFORMATION FOR SEQ ID NO:7:

(i) SEQUENCE CHARACTERISTICS:
        (A) LENGTH:2815
        (B) TYPE:nucleic acid
        (C) STRANDEDNESS:double
        (D) TOPOLOGY:linear (xi) SEQUENCE DESCRIPTION: SEQ ID NO:7:

| | |
|---|---|
| CGCCCTGATA GACGGTTTTT CGCCCTTTGA CGTTGGAGTC CACGTTCTTT | 50 |

-continued

| | |
|---|---|
| AAACTGGACA TCTCTGATGA GTTCTCAGAA GTCATCAAAG CCCTCAAGAA | 100 |
| CCACGAGGAC AAGATGCGAG TGGTGCTGAA CAAAGCTGAC CAGATCGAGA | 150 |
| CGCAGCAGCT GATGCGGGTG TACGGGCCC TCATGTGGTC CTTGGGGAAG | 200 |
| ATCGTGAACA CCCCAGAGGT GATCCGGGTC TACATCGGCT CCTTCTGGTC | 250 |
| CCACCCCCTC CTCATCCCTG ACAACCGGAA GCTCTTTGAG GCTGAGGAAC | 300 |
| AGGACCTATT CAGGGACATC CAGAGTCTGC CCCGAAATGC TGCCCTGCGC | 350 |
| AAGCTCAACG ACCTCATCAA AAGGGCCAGG CTGGCCAAGG TCCACGCCTA | 400 |
| CATCATCAGC TCTCTGAAGA AGGAGATGCC CTCGGTGTTC GGGAAGGACA | 450 |
| ACAAGAAGAA GGAGCTGGTC AACAACCTGG CCGAGATCTA TGGCCGGATC | 500 |
| GAGCGGGAGC ACCAGATCTC ACCTGGGAC TTCCCCAATC TGAAGAGGAT | 550 |
| GCAGGACCAG CTGCAGGCCC AGGACTTTAG CAAGTTCCAG CCGCTGAAGA | 600 |
| GCAAGCTGCT GGAGGTAGTG GACGACATGC TGGCCCATGA CATTGCCCAG | 650 |
| CTCATGGTGC TAGTGCGCCA GGAGGAGTCA CAGCGGCCCA TCCAGATGGT | 700 |
| GAAGGGCGGA GCGTTCGAGG GCACCCTGCA CGGCCCCTTT GGGCATGGCT | 750 |
| ATGGGGAGGG GGCTGGAGAA GGTATCGATG ATGCTGAGTG GGTGGTGGCC | 800 |
| AGGGACAAGC CCATGTACGA CGAGATCTTC TACACCCTGT CACCGGTGGA | 850 |
| TGGCAAGATC ACAGGCGCTA ATGCCAAGAA GGAGATGGTG CGCTCCAAGC | 900 |
| TGCCCAACAG TGTGCTGGGC AAGATCTGGA AGCTGGCCGA CATTGACAAG | 950 |
| GATGGCATGC TGGACGACGA CGAGTTTGCA CTGGCCAACC ACCTCATCAA | 1000 |
| AGCAAGTGGG AGGGGCACGA GCTGCCCAAC GAGCTGCCTG CCCACCTCCT | 1050 |
| GCCCCCGTCC AAGAGGAAAG TTGCCGAGTG ATGGGGTGGG GGGACATTCA | 1100 |
| GACGGGCAGT GTTAGAGGAG GAGATGGGAG CGGTGACTAC ACACACACAC | 1150 |
| ACACACACAC ACACACACAC AAACATGCAC ACACACATAT GCATATCTTG | 1200 |
| ACATTGCTCT GTAGGTGAGA GAGGACCATG ACGCCCACGT TTGCAGCTGA | 1250 |
| TACTTGTTTG GGCACACCTC CAAGTTCTCG GGATTAGAAG GACAAGAGCA | 1300 |
| CTCCCAGGCC CCAGAGTCTA AGCCTAAGTC TCTATCGCTC TTCCCCTCTC | 1350 |
| CTCGGCCACT CCCCAGATAC CAGACCTGAG GCAATTCACT TGCCAGCACA | 1400 |
| GATGGCCAAC CCACCTCCAG ATTCCCCAGT GCTTCCACAC CCGGGCTCTG | 1450 |
| AGCAAATGGA AAAGACTTTT CATTTAGTAG ACAATTCACT TCTTTTTCTG | 1500 |
| TGCTTCCCCT ATCTGCTTTG GCTTCCTAAT AAGAAATCCA TTCAAGAGCT | 1550 |
| AGGAGATCTG AGGGCAGGCG GGCAGCTGCA GGGAGGAGAG GTGAGAAAGG | 1600 |
| AAGCGTCTTC TAGAGACATT GGCCCAGGAG CTCTGTTCTT TCCTAATCTA | 1650 |
| AGCCTCTGTC TTCTTCGGCA AACCTTGCTT TGAACTCTGC CAGTATTTCA | 1700 |
| TTTTAAAGAA TCCCAGAGCG GGAGAGAGAA GAGAAAAAAA TTGATAAGAG | 1750 |
| TGAGGAAATT GTCCTGTAGT CTATTGAAAA CCAGTCAAGG TGGTTTTAGT | 1800 |
| TCATAGATTT TGTTAGATGT TCTTTCCACC TGGCCTATGA TGTTTAGATG | 1850 |
| TTCATACTTG ACTCACATTT ACCCAGCCCC TCCTGCGTAC CAGGAGCTGT | 1900 |
| GTTAGGCACT TTATATACAT TATTCTATGT GGCCCTCACT GATGCCCCAG | 1950 |
| GGAAGTATGC ATTAGCCTTC CCATTTTGCA GTTGAGGAGG CTGAGTAGCC | 2000 |

| | |
|---|---:|
| TCAGAAGGGT TTAGGCGACC TTCTGAAACT CACAGAAGTC ACGTGATGGA | 2050 |
| GAGAGGATTC AAAGCCAGGG CCTCAGACCC TCACACACTT GTCTGTGCTA | 2100 |
| TGATGTATGC AGGATCCCAG CATTGATACC AATGACAAA CTATGGAGAA | 2150 |
| CAAGCAAAGT ATGCAGGCCC CCTGCAGCCT CCCAGGACAG GCTGGCAAGG | 2200 |
| GAGGAGGGCC GGCCAGCATT TGGTGGCCCA TCAGTCTGGC CATCTGTCAC | 2250 |
| GTCACAGAAG CAAACCGTGC CTTCTGGCTC TGCGCCCAT ATTCCCAGCA | 2300 |
| TCATAGACAT CCAACAGCAC CAGCAGGAGA GTGGGCTAGC CTGCTGGATG | 2350 |
| CTGTTCGTGC CTGTCCCTGC TCTGCCTCCC ACCCAGTTGC CTGAATCATC | 2400 |
| CCAGCTCAGA TGCAGCCACT GTCTCTTGTC AAGTGGGACC TCATACTATT | 2450 |
| CTCAGAAGGC TAACTTGAGA GGTTTGGGGC CTTGTTCCCC AGAGGGTCCC | 2500 |
| CAGGGACTCT GCAGTGTCCT TGGCAAATCC CCACTGTACT CAATGCCCTA | 2550 |
| CATTCTCTTC TGTGGTCTCT CCCCTGGCTT GCTTCATGGC CACTGAACCA | 2600 |
| ATCACTTTGT ATGCTATGCT CCTACTGTGA TGGAAAACAA AATGAGTATA | 2650 |
| ACTTATTTTA TATCCATATT CAGACTATAT AGAGAATATT CTATGCATCT | 2700 |
| ATGACGTGCT TACTACTGCA GTGCATTTGT CATTAGTCTT CATGTTAATA | 2750 |
| CAGTACATTT ATTCTTTGGA AAAAAAAAG CTTATCGATA CCGTCGACCT | 2800 |
| CGAGGGGGGG CCCGG | 2815 |

(2) INFORMATION FOR SEQ ID NO:8:

(i) SEQUENCE CHARACTERISTICS:
        (A) LENGTH:5764
        (B) TYPE:nucleic acid
        (C) STRANDEDNESS:double
        (D) TOPOLOGY:linear (ix) FEATURE:N is either A T G or C (xi) SEQUENCE DESCRIPTION: SEQ ID NO:8:

| | |
|---|---:|
| GGATCCCTGA TCCCTAACTT TAATAAATAA GATAAATGGA TTGTGGCCAC | 50 |
| CCTTTATTGG GAATAGCAAT GCTCATAATA GAGCCCAGCA ATTCCTGAGC | 100 |
| ATCTCCATCA TTCTACAAGC CAAATACTTC CTAATGGTCA TTTTATAGAT | 150 |
| GGAAAGTGGT AAGGAGCCCT GGGGATCTAA CTCAGTGGAA GAACAATTGG | 200 |
| ATACCATTGC CATGAGGCCC TGTGTTTGAT TCCTATGACT GCAAACACAC | 250 |
| ACACACATGC ACATGCAACA CAGACACATA CACATACACA CACAAAGAGA | 300 |
| GAGAGAGACC ACAGTAATTT TGACTCAAGG TCCAACCAGT CAATGGGAGG | 350 |
| AGCCAGCATG TGAACCCAGA GACAGTTCCA AGACTGTGTG TGTTATCTTA | 400 |
| CATTGACCCT TCACTCTACT TCCATCCCCA AAGCTCCTCT CACTACTGTC | 450 |
| ACTCCACCAC AGGTATGATT TTGCTGCGGT CCTCGAAGTG GTTGCTGAGC | 500 |
| GGTGACCGAA TTATCCTACT CTTCGACGCC ACAAGCTGA CATCTCCGAT | 550 |
| GAGTTCTCAG AAGTCATCAA GGCTCTCAAG AACCATGAGG ACAAGATGCG | 600 |
| CGTAGTGTTG AACAAAGCTG ACCAGATCGA GACCCAGCAG CTGATGCGAG | 650 |
| ATATGGGGCC CTCATGTGGT CCCTGGGGAA GATCGTGAAC ACCCCCGAGG | 700 |
| TGATCCGGGT CTACATTGGC TCCTTCTGGT CCCACCCACT CCTCATTCCC | 750 |
| GACAACCGGA AGCTCTTTGA AGCTGAAGAG CAAGACTTGT TCAGAGACAT | 800 |

-continued

| | |
|---|---|
| TCAGAGTCTA CCCCGTAATG CTGCTCTTCG AAGCTCAACG ATCTCATCAA | 850 |
| GAGAGCCCGG CTGGCCAAGG TAACGTGCCG CCAAGTAAGT ACACCGTGAA | 900 |
| CAGGTTCGAA AGTAGAGCTC AATTGCCAGA ACTGAGGTCT TTCGGTAGGA | 950 |
| GAGTGTGGGA GGTTATGGTT CTGGCTCTGA ATTAGATGGC CAGGTTGGAG | 1000 |
| CTTGGCTCAT GTCACTCAGT GATCTGGAGG CTAGTTGATA GTTCTGTGTT | 1050 |
| GTTTCTACAT TCTCAAAATG AATGGGCTGG TGGAAGAGGA AGAGGAACAG | 1100 |
| AACATGAAAA CCCTCGTCAC CGTGCCAGAC ACCTTAGTGT TCAGAAGCTG | 1150 |
| CCACTGTCGG TGTCTACGAC AGCAGTGCTC TCACCCCCTC CGCTGTGACC | 1200 |
| TTCCCTCTCC ATAGTCTCAC CGTACTAGCA CGTGACTGTG AGACGAAAGA | 1250 |
| AGTAGTTTCA GAGCAGGTCA GAGGAAGGGC TGGAAGGGCC AGTTCAGGCT | 1300 |
| CCTCCTGAGG TTGTCCTCTT CCTCTTTGTC AGGTCCACGC CTACATCATC | 1350 |
| AGCTCCTTGA AGAAGGAGAT GCCCTCAGTG TTTGGAAGGA CACCAAAAGA | 1400 |
| AGAACTGGTG AACAACCTGG CTGAGATCTA TGGCCGGATT GAGCGAGAAC | 1450 |
| ACCAGATCTC CCTGGAGACT TCCCCAACCT GAAGAGGATG CAGGTAATGA | 1500 |
| GGGTCAGGGT CCTACGGTTG GGAGACGGCA TCTTACTAGC TGGCTGCCAG | 1550 |
| AAAATGANAA GGCTCACAGA GCTCCTGGGA GAAGCCAGAG TCATAAGTCA | 1600 |
| CAATCACTCA CAGCAAATGC CATAGCAAAG GTCGGAGAGA AACAGCCCAG | 1650 |
| TTGTCCCCAA AGGCACAGAG CTGTGTTTGA TGACACTGAA GACCTTACCT | 1700 |
| AGTGAAGGCC ACATGTTCAA CATATCCCAG AATTCCCTGG GAACAGCCTG | 1750 |
| TGGCCCACAG CATGTTTTTG GGTATGTTGC AAGCCCTTGA ACCTAAGGCT | 1800 |
| ACCACTTGGG ATTGTGTGTT TGGGGCGGG GGATGTGGTC TTCTCCAAAG | 1850 |
| TCATTCTCAG AGAGAGACTT TTCACCTGCT TTTTGTCAGC TGAGGTCCTT | 1900 |
| AGTATTTTTG CAGCAAAGCA TTCACATAAG CATCACATAG CCCNGGAACC | 1950 |
| CAAGCAAGAA GCCGCCATGC CATTAGAGTA CCTAGATACA TGCAGAGCTT | 2000 |
| TCTGCATAAA CAGGGCCTTC AACGGTTCTT GTACACGAAC TGCTGAGAAC | 2050 |
| CCAGTGAAAT ATCTTTCCTG CAAGGCCCTT AACCTAGAGT CTTGCTCTGC | 2100 |
| TCCCACAGAA TCCTCTTTGC CCAGCCATTG AGAGGAGGCA AGAAGCTTCC | 2150 |
| TGCCAGCAGT TGCCTCTGAA TTGTAGCTGT AAATAGCCTT TAAATCTTCG | 2200 |
| TCAGTGCCCA TCCATGTTTA GTGGCCTTCT TCCCCACATA ATGAGATTGC | 2250 |
| TGTGGCCAGA CCAGGGCAGT GGGCATCTAT GGTCTTCTAG AACAGTTGTT | 2300 |
| CTCAACCTGT GGGTCACGAC CCTTTGCAAT TCACAGAGG TTGCCCAAGG | 2350 |
| CCATTAGAAA CAGTATTTAC CTTATGATTC AATAACAGTA GCAAAATTAT | 2400 |
| AGTTTTGAAT AGAAACAAAA ATAATTTTAT GATGGGGAT CAGCACAACA | 2450 |
| TGAGGAAATG TATTAAAGGT TCATTAGGAG GTTGAGAACA CTGTCTAGAA | 2500 |
| GCAAGGAGAG TTGGATGTTA GGTTTGAGGG TCTTTTGAGA CTGCAAAGAT | 2550 |
| TTTCAAACTA GAGCATCTTT CTTTTTTGAT GTAGGTGGGT GGACATGTGA | 2600 |
| AGGCAAAAGA GACAGCTTTC ATATAGTCTA CATACATGCC TGTGCCTAGG | 2650 |
| TCAGTCTTTT GATATCCAGG AAATTCCTGA GAACTATAAG GTTAGGAACG | 2700 |
| ACCTTTGGCT TTTGTTAGGC TTTAGTTGCC TTGGTTTCCC ACCCCGGTAC | 2750 |
| TCTGGCCCTC TCACTAACTG TGACTAGTGT ATGACTTCCC AACCTCTAAG | 2800 |

-continued

```
AGCTCCAAAG AACAGTAGTT AGGGAGCAAG ACTCCATCCC AGAGGACTAC       2850

TGCCTTCAAG GTTCACCAAT TAACAGCCAA AACTAACTTT GGAAGAAACG       2900

TCTGAGTTCC AGTTTGTAAC AATATTTAAA GAGATGACAA TAAACAAAAC       2950

CAACACTATT TTCTTTGTTC CCCAGCTCCA GCTCTTATTC TGGTTCCTTC       3000

ATAAAAGACC TATCCTTAGC CCATCAGGTC CTTGCTCCCG TCCCCTCACA       3050

CAGCCCGTTG CTTTCACTAG AAAGATAATT GGGGAAGGAT TCTATCGTTA       3100

ATAGGAGGCA CCTTCCGTGA TATGCGCATC TCCTTCCACT GTATTCTACT       3150

TCATCCTTTT CCTTTCTCTT CTCAGGACCA GCTGCAGGCC AGGACTTCAG       3200

CAAATTCCAG CCACTGAAGA GCAAGCTGCT GGAAGTGGTT GATGATATGC       3250

TGGCTCATGA CATTGCCCAG CTCATGGTGC TGGTGCGCCA GGAAGAGACC       3300

CAACGGCCTG TCCAGATGGT GAAGGGCGGA GATTTGAGGG AACCTTACAA       3350

GGCCCCTTCG GCACGGCTAT GGAGAGGNAG CTGGGGAGGG CATCGATGAT       3400

CCGAGTGGGT GGTGGCCGGG GACAAGCCTA TGTATGATGA AGATCTTCTA       3450

CACCTTATCC CCAGTGGATG GCAAGATCAC AGGTGCCAAC GCCAAGAAGG       3500

AGATGGTGCG CTCCAAGTTG CCCAACAGCG TGCTGGGCAG ATCTGGAAGC       3550

TAGAAGGACA TTGACAAGGA TGGCATGTTG GATGATCGAG GAGTTTGCCC       3600

TGGCCAACCA CCTTATCAAA GTCAAGCTAG AGGGGCATGA GCTGCCCAGT       3650

GAGCTACCTG CCCACCTCCT CCCTCCATCT AAGAGGAAAG TATCAGAATG       3700

AGAGAGCCAG GATTCCTCAG AGCAGACAGT ATCAAAAGAG AGATAGACAT       3750

GTAGACCACA CACACACACA CACACACACA CACACACACA CACAACTTGA       3800

CAGTCACACT ATAAATGAGA AGGGTTCACC TTTGTCTGAG CACCTCTCCA       3850

ACTTCCCAGG GTTGGTAGAA GGGCAGCTTT CCCTCCTGTG TCTTAGGATA       3900

TAGGCCTGTG TCCAAACATT CCCTCCATCT TCCATTCCCC GCAGACATGA       3950

GGCTAGTTAA CACAGATGGC CCTGCCCACT CTCACCCAGT GCCTCCAGAT       4000

CTAGGCTTCC GGATCGGATA GATGGAAAAG GGCTTTTTCA TGGAATAGAA       4050

AATTTGCTTT ATTTTCTATG CTTTTATTTT TTTTCCTCTG GGCTTCCTA        4100

AGTAGAAATT GACTCAGGGC CTGGGAGCTG TGAGGGAAAG GAGAAGCTGA       4150

AAGAGGGAGG GCCACCAATC TGAGAAACCT CCATAGGGCA CTGCACCCCG       4200

ACACTTGAAA AGAGCACTGG GCCTATGTTC TCTGTGTTTT CGAATTCTGC       4250

CTGCCACCTT GGGTCAAAGA CTCACAAACA GGAAAAGAAA AAAGAAAANT       4300

TTGGTAGGAA AGCACAAGGA AGATACCCTG TGGTCTTCTT CAACAGGACA       4350

TTGGATTGGT GGTTCATGGG TTTGTCCCCA CCCCCAGCGT GGTATCTCTG       4400

GATACTCAGT TTCTTTATAC ATACCAAGCC ATTCCTGTGT GGCAAGAGCA       4450

GGGTTAGGCA CTTTCTATGT ATTAGTCCTG TGGCCTTCAT GAATGCCCCT       4500

AGGACAGTTT GCTTCCCTCC TGTTACTGCA TTTTCAGGTG AAGAGCCAAA       4550

AGACTCGAG TAGTTTAGGG TACCTTCCCA AACTCCGGGA AGTCCAAGA         4600

AGAGAAGATT CAAANTNCCA GAACGTTAGA CACCCCTCTG TCCCAGTTCT       4650

GTGATGGATG AAAGATCCCA GTGTTGCTAG CTGGTGACAA AGCACAAGGC       4700

AGTCTGAACA CACAGCCCCC TCACACAGCC TTCCAAAGCA TCCAGGCAAG       4750
```

-continued

```
GGAGGGAGGG AGGTTCACCA GCCTTTGATG GGCCAACAAT CTGACCATCT      4800

GTCACCTTGT AGAAGCAAAC TGTGCTTCTG GCCTGCGCTC GTGTTCACAA      4850

CATACAGAAG ACAGCATCAG GAGAGTGGCT GGACTGCTAG ATGTTGTCTG      4900

TGCCTATTCC TGCTCAGCCT CCCGTTCATT AGCCTAAAGC ATCCCAGCTC      4950

AAATTCAGCC CCAGGCTTTT ACAAAGCAGG ACTTCATGCT AATTCACAGA      5000

AGGCCATCTT GAAAGGACTG GGACCTCGTT CTCTAGAGTT CAAGACTCTG      5050

GTGTCTTGCA AAATTTCCAT CATTCTCAGT GCCCTCTATC TCCTCTGTGG      5100

TCTGGGGGTG GCTTGCCCTA TGGCCACTGT TGCAGTAGCT CTCTGCTACA      5150

CTCCTACTGT ATGAACTCGT ACACCTGATG TGATGGAAAA TCAAAGNAGG      5200

GTATAACTTA TTTTGTATCT ATGTTCAGAC TATGATCGAC TGTTCTGTGT      5250

ATCTTCAAGT GTCTTATACT GCAGTGTGGT TTGTCATTAG ATTCATGTTA      5300

ATACAACATA TTTACCCTTT GGTACTCTTT TGGTGACTGA GCATCATTGC      5350

ATAGCACTAG ATTCTAACAT GGCATGCCTA GTTACATGGC AACTTTGGAA      5400

GACAGTGGCT CGATCTACTC GAAAGGTCAT GAACGCACCG ACCTTCTACT      5450

GGACTGGTGA TCTTATCTAG CTTACATGAA GCTACAATGG CCACTGTTTG      5500

CTGCTCTTCT GGAGTGGAGA TGTTCACTTC ATCAAACTTA GATTTCTCTT      5550

GAGTCGATAG TAAAGGAAGA CTAAGACAGA GAGGTCTGAA TTCAAGAAAT      5600

GGCAGACAAA GTAACCACGG TAAGAGACCG ACTCCTATAC CTTAATGTTG      5650

ACGTAACGAT GGTAACTAAT ACAAGATAGT AGACCTAAGT CGATTTACGC      5700

TTGAATAAGG AAAGGGAGAT GTGTGTCCAT CGATGCCANA CAGCATGAAT      5750

GATCGATCCA GACA                                            5764
```

(2) INFORMATION FOR SEQ ID NO:9:

(i) SEQUENCE CHARACTERISTICS:
        (A) LENGTH:317
        (B) TYPE:amino acid
        (C) STRANDEDNESS:single
        (D) TOPOLOGY:linear (xi) SEQUENCE DESCRIPTION: SEQ ID NO:9:

```
Lys Leu Asp Ile Ser Asp Glu Phe Ser Glu Val Ile Lys Ala Leu
              5                  10                  15

Lys Asn His Glu Asp Lys Met Arg Val Val Leu Asn Lys Ala Asp
             20                  25                  30

Gln Ile Glu Thr Gln Gln Leu Met Arg Val Tyr Gly Ala Leu Met
             35                  40                  45

Trp Ser Leu Gly Lys Ile Val Asn Thr Pro Glu Val Ile Arg Val
             50                  55                  60

Tyr Ile Gly Ser Phe Trp Ser His Pro Leu Leu Ile Pro Asp Asn
             65                  70                  75

Arg Lys Leu Phe Glu Ala Glu Glu Gln Asp Leu Phe Arg Asp Ile
             80                  85                  90

Gln Ser Leu Pro Arg Asn Ala Ala Leu Arg Lys Leu Asn Asp Leu
             95                 100                 105

Ile Lys Arg Ala Arg Leu Ala Lys Val His Ala Tyr Ile Ile Ser
            110                 115                 120

Ser Leu Lys Lys Glu Met Pro Ser Val Phe Gly Lys Asp Asn Lys
            125                 130                 135
```

```
Lys Lys Glu Leu Val Asn Asn Leu Ala Glu Ile Tyr Gly Arg Ile
            140                 145                 150

Glu Arg Glu His Gln Ile Ser Pro Gly Asp Phe Pro Asn Leu Lys
            155                 160                 165

Arg Met Gln Asp Gln Leu Gln Ala Gln Asp Phe Ser Lys Phe Gln
            170                 175                 180

Pro Leu Lys Ser Lys Leu Leu Glu Val Val Asp Met Leu Ala
            185                 190                 195

His Asp Ile Ala Gln Leu Met Val Leu Val Arg Gln Glu Glu Ser
            200                 205                 210

Gln Arg Pro Ile Gln Met Val Lys Gly Gly Ala Phe Glu Gly Thr
            215                 220                 225

Leu His Gly Pro Phe Gly His Gly Tyr Gly Glu Gly Ala Gly Glu
            230                 235                 240

Gly Ile Asp Asp Ala Glu Trp Val Val Ala Arg Asp Lys Pro Met
            245                 250                 255

Tyr Asp Glu Ile Phe Tyr Thr Leu Ser Pro Val Asp Gly Lys Ile
            260                 265                 270

Thr Gly Ala Asn Ala Lys Lys Glu Met Val Arg Ser Lys Leu Pro
            275                 280                 285

Asn Ser Val Leu Gly Lys Ile Trp Lys Leu Ala Asp Ile Asp Lys
            290                 295                 300

Asp Gly Met Leu Asp Asp Glu Phe Ala Leu Ala Asn His Leu
            305                 310                 315

Ile Lys (2) INFORMATION FOR SEQ ID NO:10:

(i) SEQUENCE CHARACTERISTICS:
        (A) LENGTH:535
        (B) TYPE:amino acid
        (C) STRANDEDNESS:single
        (D) TOPOLOGY:linear (xi) SEQUENCE DESCRIPTION: SEQ ID NO:10:

Met Phe Ser Trp Leu Gly Asn Asp Asp Arg Arg Lys Lys Asp Pro
             5                  10                  15

Glu Val Phe Gln Thr Val Ser Asp Gly Leu Lys Lys Leu Tyr Lys
            20                  25                  30

Thr Lys Leu Leu Pro Leu Glu Glu Tyr Tyr Arg Phe His Glu Phe
            35                  40                  45

His Ser Pro Ala Leu Glu Asp Ala Asp Phe Asp Asn Lys Pro Met
            50                  55                  60

Val Leu Leu Val Gly Gln Tyr Ser Thr Gly Lys Thr Thr Phe Ile
            65                  70                  75

Arg Tyr Leu Leu Glu Gln Asp Phe Pro Gly Met Arg Ile Gly Pro
            80                  85                  90

Glu Pro Thr Thr Asp Ser Phe Ile Ala Val Met Gln Gly Asp Val
            95                  100                 105

Glu Gly Ile Ile Pro Gly Asn Ala Leu Val Val Asp Pro Lys Lys
            110                 115                 120

Pro Phe Arg Lys Leu Asn Ala Phe Gly Asn Ala Phe Leu Asn Arg
            125                 130                 135

Phe Val Cys Ala Gln Leu Pro Asn Ala Val Leu Glu Ser Ile Ser
            140                 145                 150
```

```
Val Ile Asp Thr Pro Gly Ile Leu Ser Gly Glu Lys Gln Arg Ile
            155                 160                 165

Ser Arg Gly Tyr Asp Phe Ala Ala Val Leu Glu Trp Phe Ala Glu
            170                 175                 180

Arg Val Asp Arg Ile Ile Leu Leu Phe Asp Ala His Lys Leu Asp
            185                 190                 195

Ile Ser Asp Glu Phe Ser Glu Val Ile Lys Ala Leu Lys Asn His
            200                 205                 210

Glu Asp Lys Met Arg Val Val Leu Asn Lys Ala Asp Gln Ile Glu
            215                 220                 225

Thr Gln Gln Leu Met Arg Val Tyr Gly Ala Leu Met Trp Ser Leu
            230                 235                 240

Gly Lys Ile Val Asn Thr Pro Glu Val Ile Arg Val Tyr Ile Gly
            245                 250                 255

Ser Phe Trp Ser His Pro Leu Leu Ile Pro Asp Asn Arg Lys Leu
            260                 265                 270

Phe Glu Ala Glu Glu Gln Asp Leu Phe Arg Asp Ile Gln Ser Leu
            275                 280                 285

Pro Arg Asn Ala Ala Leu Arg Lys Leu Asn Asp Leu Ile Lys Arg
            290                 295                 300

Ala Arg Leu Ala Lys Val His Ala Tyr Ile Ile Ser Ser Leu Lys
            305                 310                 315

Lys Glu Met Pro Ser Val Phe Gly Lys Asp Thr Lys Lys Glu
            320                 325                 330

Leu Val Asn Asn Leu Ala Glu Ile Tyr Gly Arg Ile Glu Arg Glu
            335                 340                 345

His Gln Ile Ser Pro Gly Asp Phe Pro Asn Leu Lys Lys Met Gln
            350                 355                 360

Asp Gln Leu Gln Ala Gln Asp Phe Ser Lys Phe Gln Pro Leu Lys
            365                 370                 375

Ser Lys Leu Leu Glu Val Val Asp Asp Met Leu Ala His Asp Ile
            380                 385                 390

Ala Gln Leu Met Val Leu Val Arg Gln Glu Glu Thr Gln Arg Pro
            395                 400                 405

Val Gln Met Val Lys Gly Gly Ala Phe Glu Gly Thr Leu Gln Gly
            410                 415                 420

Pro Phe Gly His Gly Tyr Gly Glu Gly Ala Gly Glu Gly Ile Asp
            425                 430                 435

Asp Ala Glu Trp Val Val Ala Arg Asp Lys Pro Met Tyr Asp Glu
            440                 445                 450

Ile Phe Tyr Thr Leu Ser Pro Val Asp Gly Lys Ile Thr Gly Ala
            455                 460                 465

Asn Ala Lys Lys Glu Met Val Arg Ser Lys Leu Pro Asn Ser Val
            470                 475                 480

Leu Gly Lys Ile Trp Lys Leu Ala Asp Ile Asp Lys Asp Gly Met
            485                 490                 495

Leu Asp Asp Glu Glu Phe Ala Leu Ala Asn His Leu Ile Lys Val
            500                 505                 510

Lys Leu Glu Gly His Glu Leu Pro Ser Glu Leu Pro Ala His Leu
            515                 520                 525

Leu Pro Pro Tyr Lys Arg Lys Val Ser Glu
            530                 535
```

(2) INFORMATION FOR SEQ ID NO:11:

(i) SEQUENCE CHARACTERISTICS:
        (A) LENGTH:3
        (B) TYPE:amino acid
        (C) STRANDEDNESS:single
        (D) TOPOLOGY:linear (xi) SEQUENCE DESCRIPTION: SEQ ID NO:11:

Asn Pro Phe
        3

(2) INFORMATION FOR SEQ ID NO:12:

(i) SEQUENCE CHARACTERISTICS:
        (A) LENGTH:3
        (B) TYPE:amino acid
        (C) STRANDEDNESS:single
        (D) TOPOLOGY:linear (xi) SEQUENCE DESCRIPTION: SEQ ID NO:12:

Asp Pro Phe
        3

(2) INFORMATION FOR SEQ ID NO:13:

(i) SEQUENCE CHARACTERISTICS:
        (A) LENGTH:432
        (B) TYPE:nucleic acid
        (C) STRANDEDNESS:double
        (D) TOPOLOGY:linear (xi) SEQUENCE DESCRIPTION: SEQ ID NO:13:

```
CGTGTCCGGC AGTATGTTCA GCTGGGTCAG CAAGGATGCC CGCCGCAAGA            50

AGGAGCCGGA GCTCTTCCAG ACGGTGGCTG AGGGGCTGCG GCAGCTGTAC           100

GCGCAGAAGC TGCTACCCCT GGAGGAGCAC TACCGCTTCC ACGAGTTCCA           150

CTCGCCCGCG CTGGAGGACG CTGACTTCGA CAACAAGCCT ATGGTGCTCC           200

TCGTGGGGCA GTACAGCACG GGCAAGACCA CCTTCATCCG ACACCTGATC           250

GAGCAGGACT TCCCGGGGAT GCGCATCGGG CCCGAGCCCA CCACCGACTC           300

CTTCATCGCC GTCATGCACG GCCCCACTGA GGGCGTGGTG CCGGGCAACG           350

CGCTCGTGGT GGACCCGCGG CGCCCCTTCC GCAAGCTCAA CGCGTTTGGC           400

AACGCTTTCC TCAACAGGTT CATGTGGCCC CA                              432
```

(2) INFORMATION FOR SEQ ID NO:14:

(i) SEQUENCE CHARACTERISTICS:
        (A) LENGTH:535
        (B) TYPE:amino acid
        (C) STRANDEDNESS:single
        (D) TOPOLOGY:linear (xi) SEQUENCE DESCRIPTION: SEQ ID NO:14:

```
Met Phe Ser Tyr Leu Gly Gly Asp Ser Ser Lys Lys Lys Asn Lys
                5                  10                  15

Glu Val Leu Glu Trp Val Ser Glu Gly Leu Arg Lys Ile Tyr Lys
                20                 25                  30

Gln Lys Leu Leu Pro Leu Glu Glu Phe His Lys Phe His Asp Phe
                35                 40                  45

His Ser Pro Ala Leu Asp Asp Pro Asp Phe Asp Xaa Lys Pro Met
                50                 55                  60
```

```
Ile Leu Leu Val Gly Ala Ile Phe Arg Pro Gly Lys Thr Thr Phe
                65                  70                  75

Ile Arg Tyr Leu Leu Glu Ser Asp Phe Pro Gly Ile Arg Ile Gly
                80                  85                  90

Pro Glu Pro Thr Thr Asp Arg Phe Ile Ala Val Met His Gly Asp
                95                 100                 105

Glu Glu Gly Ser Ile Pro Gly Asn Ala Leu Val Val Asp Ala Lys
               110                 115                 120

Lys Gln Phe Arg Ala Leu Ser Gly Phe Gly Asn Ala Phe Leu Asn
               125                 130                 135

Arg Phe Gln Cys Ser Thr Leu Pro Asn Gln Val Leu Glu Ser Val
               140                 145                 150

Thr Ile Val Asp Thr Pro Gly Ile Leu Ser Gly Glu Lys Gln Arg
               155                 160                 165

Ile Asp Arg Gly Tyr Asp Phe Thr Gly Val Leu Glu Trp Phe Ala
               170                 175                 180

Glu Arg Val Asp Arg Ile Ile Leu Leu Phe Asp Ala His Lys Leu
               185                 190                 195

Asp Ile Ser Asp Glu Phe Lys Arg Cys Ile Xaa Ala Leu Ala Gly
               200                 205                 210

Asn Glu Asp Lys Ile Arg Ile Xaa Leu Asn Lys Ser Asp Met Gly
               215                 220                 225

Asp His Gln Gln Xaa Met Arg Val Tyr Gly Ala Leu Met Trp Ser
               230                 235                 240

Leu Gly Lys Val Phe Xaa Thr Pro Glu Val Ser Arg Val Tyr Leu
               245                 250                 255

Gly Ser Phe Trp Asp His Pro Leu His Tyr Asp Leu Xaa Arg Arg
               260                 265                 270

Leu Phe Gln Asp Glu Gln His Asp Leu Phe Gln Asp Leu Gln Ala
               275                 280                 285

Leu Pro Arg Asn Ala Ala Leu Arg Lys Leu Asn Asp Leu Ile Lys
               290                 295                 300

Arg Ala Arg Leu Ala Lys Val His Ala Tyr Ile Ile Ala Glu Leu
               305                 310                 315

Arg Lys Gln Met Pro Ser Met Ile Gly Lys Asp Lys Lys Lys
               320                 325                 330

Asp Leu Ile Gln Asn Leu Asp Lys Ile Tyr Glu Gln Leu Gln Arg
               335                 340                 345

Glu His Asn Ile Ser Pro Gly Asp Phe Pro Asp Val Asn Lys Met
               350                 355                 360

Arg Glu Lys Leu Gln Thr Gln Asp Phe Ser Lys Phe Asn Pro Leu
               365                 370                 375

Lys Pro Lys Leu Leu Glu Val Val Asp Gly Met Leu Ala Thr Asp
               380                 385                 390

Ile Ala Arg Leu Met Ala GLn Ile Pro Lys Glu Glu Ala Ala Ala
               395                 400                 405

Pro Ala Gly Ser Asn Gly Ser Ala Asp Pro Thr Val Arg Gly Gly
               410                 415                 420

Ala Phe Ser Gln Thr Thr Glu Ala Glu Thr Pro Phe Gly Phe Gly
               425                 430                 435

Arg Gly Glu Gly Phe Asp Lys Gly Ala Asp Glu Ala Glu Trp Val
               440                 445                 450
```

```
Val Ser Arg Glu Arg Thr Thr Ala Asp Ser Thr Phe Glu Ser Leu
                455                 460                 465

Gly Pro Val Asn Gly Tyr Leu Ser Gly Arg Ala Ala Lys Glu His
                470                 475                 480

Met Val Lys Ser Lys Leu Pro Asn Ser Val Leu Gly Lys Val Trp
                485                 490                 495

Lys Leu Ala Asp Ile Asp Lys Asp Gly Gln Leu Asp Ala Asp Glu
                500                 505                 510

Phe Ala Leu Ala Asn Tyr Leu Ile Asn Leu Lys Leu Glu Gly His
                515                 520                 525

Glu Ile Pro Ser Glu Leu Pro Lys His Leu
                530                 535

(2) INFORMATION FOR SEQ ID NO:15:

(i) SEQUENCE CHARACTERISTICS:
        (A) LENGTH:496
        (B) TYPE:amino acid
        (C) STRANDEDNESS:single
        (D) TOPOLOGY:linear (xi) SEQUENCE DESCRIPTION: SEQ ID NO:15:

Met Phe Ser Phe Leu Lys Arg Glu Lys Asn Thr Gln Glu Val Val
                  5                  10                  15

Glu Asn Val Ile Gly Glu Leu Lys Lys Ile Tyr Arg Ser Lys Leu
                 20                  25                  30

Leu Pro Leu Glu Glu His Tyr Gln Phe His Asp Phe His Ser Pro
                 35                  40                  45

Lys Leu Glu Asp Pro Asp Phe Asp Ala Asn Pro Val Ile Leu Leu
                 50                  55                  60

Val Gly Leu Tyr Ser Thr Gly Lys Thr Thr Phe Ile Arg Tyr Leu
                 65                  70                  75

Leu Glu Arg Asp Phe Pro Gly Ile Arg Ile Gly Pro Glu Pro Thr
                 80                  85                  90

Thr Asp Arg Phe Ile Ala Val Met Tyr Asp Asp Lys Glu Gly Val
                 95                 100                 105

Ile Pro Gly Asn Ala Leu Val Val Asp Pro Asn Lys Gln Phe Arg
                110                 115                 120

Pro Leu Ser Lys Tyr Gly Asn Ala Phe Leu Asn Arg Phe Gln Cys
                125                 130                 135

Ser Ser Val Ala Ser Pro Val Leu Asn Ala Ile Ser Asn Val Asp
                140                 145                 150

Thr Pro Gly Ile Leu Ser Gly Glu Lys Gln Arg Ile Asp Arg Gly
                155                 160                 165

Tyr Asp Phe Thr Gly Val Leu Glu Trp Phe Ala Glu Arg Val Asp
                170                 175                 180

Arg Ile Ile Leu Leu Phe Asp Ala His Lys Leu Asp Ile Ser Asp
                185                 190                 195

Glu Phe Arg Arg Ser Ile Glu Ala Leu Lys Gly His Asp Asp Lys
                200                 205                 210

Ile Arg Ile Ile Leu Asn Lys Ala Asp Met Ile Asp His Gln Gln
                215                 220                 225

Leu Met Arg Val Tyr Gly Ala Leu Met Trp Ser Leu Gly Lys Val
                230                 235                 240

Leu Gln Asp Leu Leu His Leu Leu Asp Val Gly Glu Val Ala Gly
                245                 250                 255
```

```
Arg Asn Gly Val Leu Ala Leu Asp Ala Ile Val Tyr Leu Ala Glu
            260                 265                 270
Val Leu Asn Gln Val Leu Leu Ala Val Leu Ala Glu His Arg
        275                 280                 285
Gly His Val Leu Ala Gln Leu Gly Asn Asp Glu Gly Met His Leu
            290                 295                 300
Gly Gln Ala Arg Pro Leu Asp Gln Ile Val Gln Leu Ala Gln Gly
            305                 310                 315
Gly Val Thr Arg Gln Gly Leu Gln His Gln Asp Phe Thr Lys Phe
            320                 325                 330
His Ser Leu Lys Pro His Leu Leu Asp Ile Val Asp Asn Met Leu
            335                 340                 345
Ala Lys Asp Ile Ala Arg Leu Met Glu Met Ile Pro Gln Glu Glu
            350                 355                 360
Met Thr Met Val Ala Asp Pro Ile Val Lys Gly Gly Ala Phe Glu
            365                 370                 375
Gly Val Ile Asp Asp His Val Ser Pro Phe Gly Tyr Met Lys Gly
            380                 385                 390
Glu Gly Ile Asp Ala Gly Tyr Gly Glu His Glu Trp Ile Cys Asn
            395                 400                 405
Lys Asp Lys Pro Arg Thr Asp Gly Ile Phe Asn Gly Leu Gly Pro
            410                 415                 420
Val Asp Gly Lys Ile Ser Gly Ala Thr Ala Lys Gln Glu Leu Ile
            425                 430                 435
Lys Ser Lys Leu Pro Asn Ser Val Leu Ser Lys Ile Trp Lys Leu
            440                 445                 450
Ser Asp Val Asp Gly Asp Gly Phe Leu Asp Ser Asp Glu Phe Ala
            455                 460                 465
Leu Ala Leu His Leu Ile Asn Val Lys Leu Glu Gly Cys Glu Leu
            470                 475                 480
Pro Thr Val Leu Pro Glu His Leu Val Pro Pro Ser Lys Arg Tyr
            485                 490                 495
Asp (2) INFORMATION FOR SEQ ID NO:16:

(i) SEQUENCE CHARACTERISTICS:
        (A) LENGTH:15
        (B) TYPE:amino acid
        (C) STRANDEDNESS:single
        (D) TOPOLOGY:linear (xi) SEQUENCE DESCRIPTION: SEQ ID NO:16:

Gly Xaa Xaa Xaa Xaa Gly Lys Thr Xaa Xaa Xaa Xaa Xaa Xaa Val
                5                  10                  15

(2) INFORMATION FOR SEQ ID NO:17:

(i) SEQUENCE CHARACTERISTICS:
        (A) LENGTH:17
        (B) TYPE:nucleic acid
        (C) STRANDEDNESS:single
        (D) TOPOLOGY:linear (xi) SEQUENCE DESCRIPTION: SEQ ID NO:17:

CATGAATTCC TGCTTTG                                          17
```

(2) INFORMATION FOR SEQ ID NO:18:

(i) SEQUENCE CHARACTERISTICS:
        (A) LENGTH:18
        (B) TYPE:nucleic acid
        (C) STRANDEDNESS:single
        (D) TOPOLOGY:linear (xi) SEQUENCE DESCRIPTION: SEQ ID NO:18:

GACTCAGAGT AGTTTAGG                                          18

(2) INFORMATION FOR SEQ ID NO:19:

(i) SEQUENCE CHARACTERISTICS:
        (A) LENGTH:17
        (B) TYPE:nucleic acid
        (C) STRANDEDNESS:single
        (D) TOPOLOGY:linear (xi) SEQUENCE DESCRIPTION: SEQ ID NO:19:

CTCCTCCCTC CATCTAA                                          17

(2) INFORMATION FOR SEQ ID NO:20:

(i) SEQUENCE CHARACTERISTICS:
        (A) LENGTH:18
        (B) TYPE:nucleic acid
        (C) STRANDEDNESS:single
        (D) TOPOLOGY:linear (xi) SEQUENCE DESCRIPTION: SEQ ID NO:20:

CTCAGACAAA GGTGTTCC                                         18

(2) INFORMATION FOR SEQ ID NO:21:

(i) SEQUENCE CHARACTERISTICS:
        (A) LENGTH:17
        (B) TYPE:nucleic acid
        (C) STRANDEDNESS:single
        (D) TOPOLOGY:linear (xi) SEQUENCE DESCRIPTION: SEQ ID NO:21:

CTCCTCCCTC CATCTAA                                          17

(2) INFORMATION FOR SEQ ID NO:22:

(i) SEQUENCE CHARACTERISTICS:
        (A) LENGTH:18
        (B) TYPE:nucleic acid
        (C) STRANDEDNESS:single
        (D) TOPOLOGY:linear (xi) SEQUENCE DESCRIPTION: SEQ ID NO:22:

CTCAGACAAA GGTGTTCC                                         18

(2) INFORMATION FOR SEQ ID NO:23:

(i) SEQUENCE CHARACTERISTICS:
        (A) LENGTH:37
        (B) TYPE:nucleic acid
        (C) STRANDEDNESS:single
        (D) TOPOLOGY:linear (xi) SEQUENCE DESCRIPTION: SEQ ID NO:23:

GGCCACGCGT CGACTAGTAC TTTTTTTTTT TTTTTTT                  37

(2) INFORMATION FOR SEQ ID NO:24:

(i) SEQUENCE CHARACTERISTICS:
            (A) LENGTH:21
            (B) TYPE:nucleic acid
            (C) STRANDEDNESS:single
            (D) TOPOLOGY:linear (xi) SEQUENCE DESCRIPTION: SEQ ID NO:24:

GGCATTGATG ATGTTGAGTG G                                        21

(2) INFORMATION FOR SEQ ID NO:25:

(i) SEQUENCE CHARACTERISTICS:
            (A) LENGTH:19
            (B) TYPE:nucleic acid
            (C) STRANDEDNESS:single
            (D) TOPOLOGY:linear (xi) SEQUENCE DESCRIPTION: SEQ ID NO:25:

CGAGGAGTTT GCCCTGGCG                                           19

(2) INFORMATION FOR SEQ ID NO:26:

(i) SEQUENCE CHARACTERISTICS:
            (A) LENGTH:17
            (B) TYPE:nucleic acid
            (C) STRANDEDNESS:single
            (D) TOPOLOGY:linear (xi) SEQUENCE DESCRIPTION: SEQ ID NO:26:

GCTGACCCTG CTCTGCC                                             17

(2) INFORMATION FOR SEQ ID NO:27:

(i) SEQUENCE CHARACTERISTICS:
            (A) LENGTH:18
            (B) TYPE:nucleic acid
            (C) STRANDEDNESS:single
            (D) TOPOLOGY:linear (xi) SEQUENCE DESCRIPTION: SEQ ID NO:27:

ACAAATGCAC TGCAGTAG                                            18